US009913921B2

(12) United States Patent
Robillard et al.

(10) Patent No.: US 9,913,921 B2
(45) Date of Patent: Mar. 13, 2018

(54) PRETARGETING KIT FOR IMAGING OR THERAPY COMPRISING A TRANS-CYCLOOCTENE DIENOPHILE AND A DIENE

(75) Inventors: Marc Stefan Robillard, Eindhoven (NL); Johan Lub, Valkenswaard (NL); Raffaella Rossin, Eindhoven (NL); Sandra Martina Van Ben Bosch, Weert (NL); Ronny Mathieu Versteegen, Hegelsom (NL)

(73) Assignee: TAGWORKS PHARMACEUTICALS B.V., Eindhoven (NL)

( * ) Notice: Subject to any disclaimer, the term of this patent is extended or adjusted under 35 U.S.C. 154(b) by 0 days.

(21) Appl. No.: 14/115,455

(22) PCT Filed: May 7, 2012

(86) PCT No.: PCT/IB2012/052260
§ 371 (c)(1),
(2), (4) Date: Nov. 4, 2013

(87) PCT Pub. No.: WO2012/153254
PCT Pub. Date: Nov. 15, 2012

(65) Prior Publication Data
US 2014/0093450 A1 Apr. 3, 2014

(30) Foreign Application Priority Data
May 9, 2011 (EP) .................................... 11165267

(51) Int. Cl.
| A61K 51/10 | (2006.01) |
| A61K 51/04 | (2006.01) |
| B82Y 5/00 | (2011.01) |
| C07D 207/46 | (2006.01) |
| C07D 235/02 | (2006.01) |
| C07D 245/02 | (2006.01) |
| C07D 249/16 | (2006.01) |
| A61K 47/68 | (2017.01) |
| A61K 49/10 | (2006.01) |

(52) U.S. Cl.
CPC ...... *A61K 51/1093* (2013.01); *A61K 47/6897* (2017.08); *A61K 51/041* (2013.01); *A61K 51/0495* (2013.01); *A61K 51/0497* (2013.01); *B82Y 5/00* (2013.01); *C07D 207/46* (2013.01); *C07D 235/02* (2013.01); *C07D 245/02* (2013.01); *C07D 249/16* (2013.01); *A61K 49/106* (2013.01)

(58) Field of Classification Search
None
See application file for complete search history.

(56) References Cited

U.S. PATENT DOCUMENTS 3,143,578 A 8/1964 O'Connor et al.
2003/0220507 A1* 11/2003 MacMillan et al. ....... 548/302.1

2009/0023916 A1 1/2009 Fox
2012/0039803 A1 2/2012 Robillard
2013/0266512 A1* 10/2013 Fox et al. .................... 424/1.89

FOREIGN PATENT DOCUMENTS

| WO | WO2010051530 | 5/2010 |
| WO | WO2010119382 | * 10/2010 |
| WO | WO2010119389 | 10/2010 |
| WO | WO2011095336 | 8/2011 |
| WO | WO2012049624 | 4/2012 |

OTHER PUBLICATIONS

Blackman et al. (J. Am. Chem. Soc. 2008, 130, 13518-13519).*
Rossin et al. (Angew. Chem. Int. Ed. 2010, 49, 3375-3378).*
Fringuelli et al. (Organic Prep. Proc. Int. 1990, 22, 131-165).*
J. Dommerholt et al., "Readily Accessible Bicyclononynes for Bioorthogonal Labeling and Three-Dimensional Imaging of Living Cells", Agewandte Chemie International Edition, vol. 49, No. 49, Sep. 20, 2012, pp. 9422-9423.
G.J. Garcia et al., "Reverse-Electron-Demand Diels-Alder Dienophile [pi]-Face Selectivity Via Conformation Dependent Transmission of [pi]-[sigma]-[pi] Electronic Interactions", Tetrahedron Letters, Elsevier, Amsterdam, NL, vol. 32, No. 28, Jul. 8, 1991, pp. 3293-3296.
E.J. Keliher et al., "High-Yielding, Two-Steo Labeling Strategy for F-PARP1 Inhibitors", Chemmedchem Mar. 7, 2011, John Wiley and Sons Ltd GBR, vol. 6, No. 3, Mar. 7, 2011, p. 425.
R. Selvaraj et al., "Tetrazine-Trans-Cyclooctene Ligation for the Rapid Construction of Integrin targeted PET Tracer base on a Cyclic RGD Peptide", Bioorganize & Medicinal Chemistry Letters Sep. 1, 2011, vol. 21, No. 17, 2011, pp. 5011-5014.
M.T. Taylor et al., "Design and Synthesis of Highly Reactive Dienophiles for the Tetrazine-trans-Cyclooctene Ligation", Journal of the American Chemical Society, vol. 133, No. 25, Jun. 29, 2001, pp. 9646-9649.
U.S. Appl. No. 61/367,174, filed Jul. 23, 2010, Tetrazine-trans-cyclooctene ligation as the basis of PET/SPECT probes and radiotherapies, Joseph M. Fox et al.
Goldenberg et al "Antibody Pretargeting Advances Cancer Radioimmuodetection and Radioimmunotherapy" Journal of Clinical Oncology, vol. 24, No. 5 Feb. 10, 2006 p. 823-834.
Boerman et al "Pretargeted Radioimmunotherapy of Cancer." Journal of Nuclear Medicine, vol. 44, No. 3, Mar. 2003 p. 400-413.
Goldenberg et al "Radioimmunotheraphy: Is Avidin-Biotin Pretargeting the Preferred Choice." European Journal of Nuclear Med and Molecular Imaging, Jun. 2003.

(Continued)

*Primary Examiner* — Michael G Hartley
*Assistant Examiner* — Melissa J Perreira
(74) *Attorney, Agent, or Firm* — Lucas & Mercanti, LLP

(57) ABSTRACT

Described is a pretargeting method, and related kits, for targeted medical imaging and/or therapeutics, wherein use is made of abiotic reactive chemical groups that exhibit bioorthogonal reactivity towards each other. The invention involves the use of [4+2] inverse electron demand (retro) Diels-Alder chemistry in providing the coupling between a Pre-targeting Probe and an Effector Probe. To this end one of these probes comprises an electron-deficient tetrazine or other suitable diene, and the other an E-cyclooctene which has a flattened structure as a result of the position of at least two exocyclic bonds.

4 Claims, 16 Drawing Sheets

(56) References Cited

OTHER PUBLICATIONS

Rossin et al "In Vivo Chemistry for Pretargeted Tumor Imaging in Live Mice" Angew. Chem. Int. Ed (2010) vol. 49, p. 3375-3378.
Thalhammer et al "Reaktivitat Einfacher Offenkettiger Und Cyclischer Dienophile Bei Diels-Alder-Reaktionen Mit Inversem Elektrnenbedarf" Tetrahedron Lett 1990, 31, 6851 (German only available).
Leong et al "Structure and Conformation of Cyclopentene, Cycloheptene and Trans-Cyclooctene" Journal of Molecular Structure, 445 (1998) p. 149-160.
King et al "Frontier Molecular Orbital Correlations for Predicting Rate Constants Between Alkenes and the Tropospheric Oxidants . . . " Phys. Chem. Chem Phys, p. 2231-2238 Jan. 1999.
Boger "Diels-Alder Reactions of Heterocyclic Azadienes: Scope and Application" Chem. Rev. 1986, p. 781-793.

\* cited by examiner

PRETARGETING KIT FOR IMAGING OR THERAPY COMPRISING A TRANS-CYCLOOCTENE DIENOPHILE AND A DIENE

CROSS-REFERENCE TO PRIOR APPLICATIONS

This application is the U.S. National Phase application under 35 U.S.C. § 371 of International Application Serial No. PCT/IB2012/052260, filed on May 7, 2012, which claims the benefit of European Application Serial No. 11165267.3, filed on May 9, 2011. These applications are hereby incorporated by reference herein.

FIELD OF THE INVENTION

The invention relates to a pretargeting method, for targeted medical imaging and/or therapeutics, wherein use is made of abiotic reactive chemical groups that exhibit bio-orthogonal reactivity towards each other. The invention also relates to a pretargeting kit comprising at least one Pre-targeting Probe and at least one Effector Probe, wherein the Pre-targeting Probe comprises a primary targeting moiety and a first Bio-orthogonal Reactive Group, and wherein the Effector Probe comprises an Effector Moiety, such as a label or a pharmaceutically active compound, and a second Bio-orthogonal Reactive Group. The invention also relates to pre-targeting agents used in the above-mentioned method and kit. The invention particularly pertains to nuclear imaging and radiotherapy.

BACKGROUND OF THE INVENTION

In many areas of medical diagnosis and therapy, it is desired to selectively deliver an agent, such as a therapeutic agent (a drug) or a diagnostic (e.g. imaging) agent, to a specific site, or a confined region, in the body of a subject such as a patient.

Active targeting of an organ or a tissue is achieved by the direct or indirect conjugation of the desired active moieties (e.g. a contrast enhancing agent or a cytotoxic compound) to a targeting construct, which binds to cell surfaces or promotes cellular uptake at or near the target site of interest. The targeting moieties used to target such agents are typically constructs that have affinity for cell surface targets (e.g., membrane receptors), structural proteins (e.g., amyloid plaques), or intracellular targets (e.g., RNA, DNA, enzymes, cell signaling pathways). These moieties can be antibodies (fragments), proteins, aptamers, oligopeptides, oligonucleotides, oligosaccharides, as well as peptides, peptoids and organic drug compounds known to accumulate at a particular disease or malfunction. Alternatively, a contrast/therapeutic agent may target a metabolic pathway, which is upregulated during a disease (like infection or cancer) such as DNA, protein, and membrane synthesis and carbohydrate uptake. In diseased tissues, abovementioned markers can discriminate diseased cells from healthy tissue and offer unique possibilities for early detection, specific diagnosis and (targeted) therapy.

An important criterion for successful molecular imaging/therapy agents in general and nuclear imaging/therapy agents in particular is that they exhibit a high target uptake while showing a rapid clearance (through renal and/or hepatobiliary systems) from non-target tissue and from the blood. However, this is often problematic: for example, imaging studies in humans have shown that the maximum concentration of a radio labeled antibody at the tumor site is attainable within 24 h but several more days are required before the concentration of the labeled antibody in circulation decreases to levels low enough for successful imaging to take place.

These problems (especially for nuclear imaging and therapy) with slow or insufficient accumulation in target tissue and slow clearance from non-target areas have lead to the application of pre-targeting approaches.

Pretargeting refers to a step in a targeting method, wherein a primary target (e.g. a cell surface) is provided with a Pre-targeting Probe. The latter comprises a secondary target, which will eventually be targeted by a further probe (the Effector Probe) equipped with a secondary targeting moiety.

Thus, in pre-targeting, a Pre-targeting Probe is bound to a primary target. The Pre-targeting Probe also carries secondary targets, which facilitate specific conjugation to a diagnostic (imaging) and/or therapeutic agent, the Effector Probe. After the construct forming the Pre-targeting Probe has localized at the target site (taking time, e.g. 24 h), a clearing agent can be used to remove excess from the blood, if natural clearance is not sufficient. In a second incubation step (preferably taking a shorter time, e.g., 1-6 hours), the Effector Probe binds to the (pre)bound Pre-targeting Probe via its secondary targeting moiety. The secondary target (present on the Pre-targeting Probe) and the secondary targeting moiety (present on the Effector Probe) should bind rapidly, with high specificity and high affinity and should be stable within the body.

The general concept of pre-targeting is outlined for imaging in FIG. 1. Herein the Effector Probe is an imaging probe comprising a detectable label for an imaging modality. The Effector Probe binds to the (pre)-bound Pre-targeting Probe via its secondary targeting groups.

Common examples for secondary target/secondary targeting moiety pairs are biotin/streptavidin or antibody/antigen systems. To be effective, the Effector Probe must be rapidly excreted from the body (e.g., through the kidneys) to provide the desired high tumor accumulation with relatively low non-target accumulation. Therefore, these probes are usually small.

In nuclear imaging and radiotherapy the concept of pre-targeting is of further advantage, as the time consuming pre-targeting step can be carried out without using radionuclides, while the secondary targeting step using a radionuclide can be carried out faster. The latter allows the use of shorter lived radionuclides with the advantage of minimizing the radiation dose to the patient and, for instance, the usage of PET agents instead of SPECT agents. Using a pre-targeting approach in MRI in combination with multidentate ligand systems (streptavidin, dendrimers) can afford signal amplification at target sites. Furthermore, in general, this approach facilitates the usage of a universal contrast agent.

The entities that carry out highly selective interactions in biology in general (like antibody-antigen), and in pre-targeting in particular (biotin-streptavidin, antibody/haptens, antisense oligonucleotides), are very large. As a result, pre-targeting with peptides and small organic moieties as primary targeting groups, as well as metabolic imaging and intracellular target imaging, have remained out of reach as the size of the secondary targets makes the use of small primary groups pointless.

Moreover, the current pretargeting systems are hampered by factors associated with their biological nature. Biotin is an endogenous molecule and its conjugates can be cleaved by the serum enzyme biotinidase. When antisense pretargeting is used, the oligonucleotides can be subject to attack by RNAse and DNAse. Proteins and peptides are also subject to natural decomposition pathways. These interactions can be further impaired by their non-covalent and dynamic nature and limited on-target residence time. Also, endogenous biotin competes with biotin conjugates for streptavidin binding. Finally, streptavidin is highly immunogenic.

A recent development is to avoid the drawbacks associated with pretargeting solely on the basis of natural/biological targeting constructs (i.e., biotin/streptavidin, antibody/hapten, antisense oligonucleotides).

A reference in this respect is WO 2010/051530, wherein pretargeting is discussed on the basis of the reactivity between certain dienes, such as tetrazines and dienophiles such as a trans-cyclooctenol (TCO).

Although on the basis of such systems a relatively fast reaction can be obtained, this does not come near the reactivity of the above-mentioned biotin-streptavidin system. Hence, avoiding the drawbacks of the latter, goes at cost of the primary requirement of the reaction, viz. speed. It is thus desired to provide a system that is not based on biomolecules as discussed above, and yet has a desirably fast reaction rate.

SUMMARY OF THE INVENTION

In order to better address the foregoing desires, the invention, in one aspect, provides a kit for targeted medical imaging and/or therapeutics, comprising at least one Pre-targeting Probe and at least one Effector Probe, wherein the Pre-targeting Probe comprises a Primary Targeting Moiety and a first Bio-orthogonal Reactive Group, and wherein the Effector Probe comprises an Effector Moiety, such as a label or a pharmaceutically active compound, and a second Bio-orthogonal Reactive Group, wherein either of the first and second Bio-orthogonal Reactive Groups is a dienophile and the other of the first and second Bio-orthogonal Reactive Groups is a diene, wherein the dienophile is a trans-cyclooctene moiety comprising at least two exocyclic bonds fixed in the same plane, and comprising at least one linkage, optionally via a spacer, to the Pre-targeting Probe or the Effector Probe.

In another aspect, the invention provides a pre-targeting method, as well as pre-targeting agents used therein, and targeted medical imaging or therapy wherein this kit is used.

In a still further aspect, the invention is a compound comprising an eight-membered non-aromatic cyclic monoalkenylene moiety (preferably a cyclooctene moiety, and more preferably a trans-cyclooctene moiety), said moiety comprising at least two exocyclic bonds fixed in the same plane, for use in a pre-targeting method in an animal or a human being.

In yet another aspect, the invention resides in the use of a compound comprising a trans-cyclooctene moiety, said moiety comprising at least two exocyclic bonds fixed in substantially the same plane, as a dienophile reactant in a pre-targeting method based on the retro Diels-Alder reaction.

(11-oxo-11-(6-(6-(pyridin-2-yl)-1,2,4,5-tetrazin-3-yl) pyridin-3-ylamino)undecylamino)ethyl)-1,4,7,10-tetraazacyclododecane-1,4,7-triyl)triacetic acid (48), described in Example 11.

Figure 18:
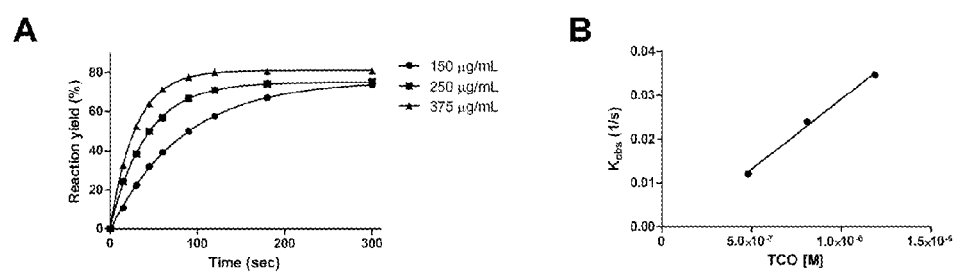

FIGS. 18a and 18b depict the time-dependent reaction yields between $^{177}$Lu-DOTA-tetrazine 8 (26.6 nM) and CC49-TCO(12) (3 different mAb concentrations) and plots of $K_{obs}$ vs. TCO 12 concentration, described in Example 15.

Figure 19:
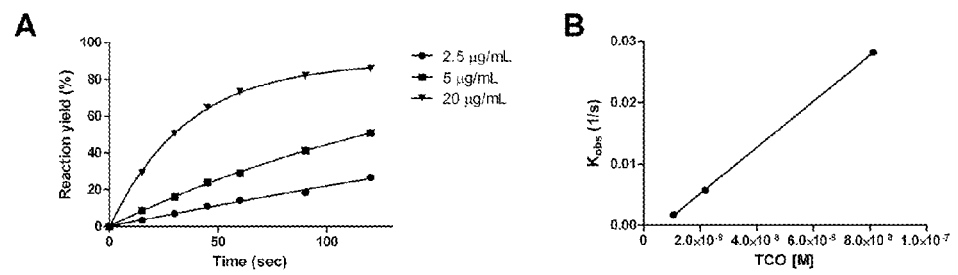

FIGS. 19a and 19b depict the time-dependent reaction yields between $^{177}$Lu-DOTAtetrazine 8 (1.73 nM) and CC49-TCO(26) (3 different mAb concentrations) and plots of $K_{obs}$ vs. TCO 26 concentration, described in Example 15.

Figure 20:
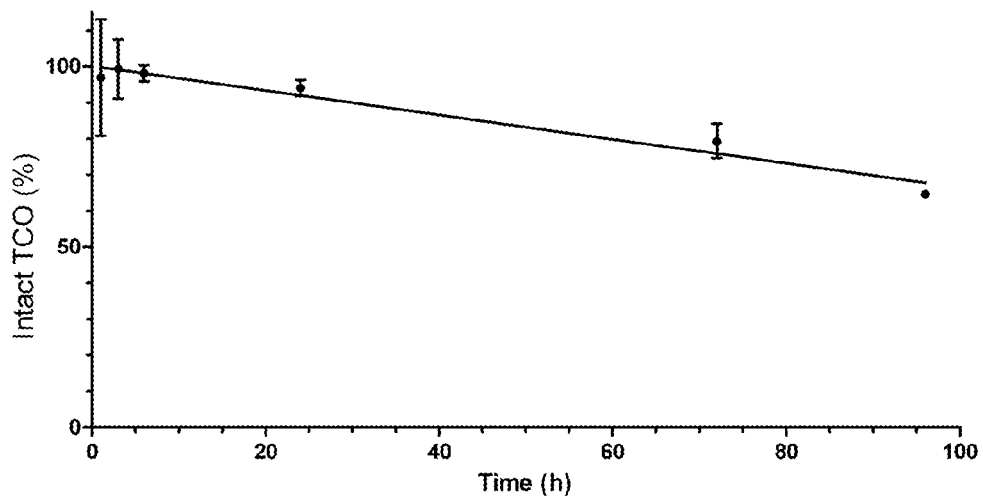

FIG. 20 depicts the in vivo stability of TCO 12 conjugated to CC49, described in Example 16. Bars represent the mean and error bars represent one standard deviation (n=3).

Figure 21:
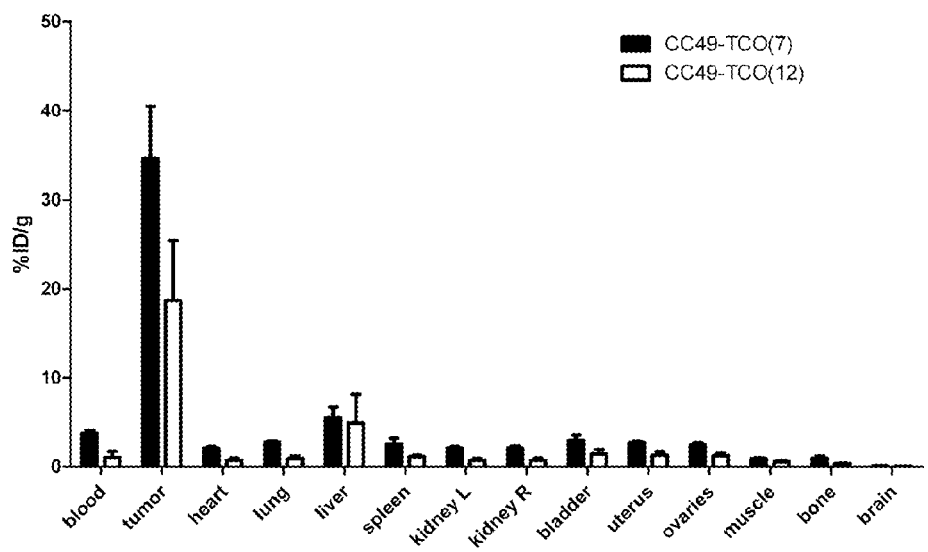

FIG. 21 depicts the biodistribution of $^{125}$I-CC49-TCO(7) and $^{125}$I-CC49-TCO (12) in tumor bearing mice 29 h post-mAb injection, described in Example 17. Data presented as % ID/g, error bars=one standard deviation (n=4).

Figure 22:
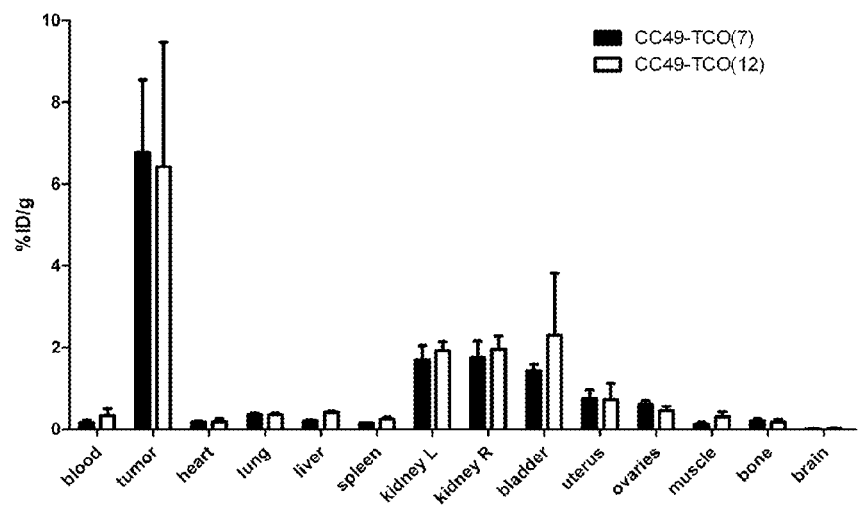

FIG. 22 depicts the biodistribution of $^{177}$Lu-tetrazine 8 (3 h post-injection) in mice pre-treated CC49-TCO(7) and CC49-TCO(12), described in Example 17. Data presented as % ID/g, error bars=one standard deviation (n=4).

Figure 23:
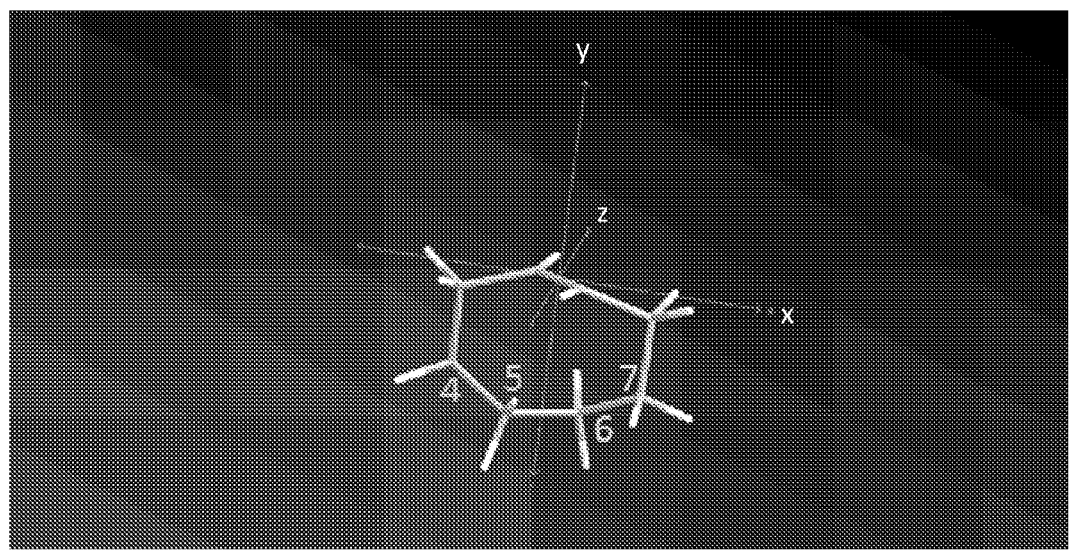

FIG. 23 depicts a three-dimensional structure representation via modelling software (the letters x, y, and z represent the x-axis, y-axis, and z-axis, respectively), described in Example 18.

DETAILED DESCRIPTION OF THE INVENTION

In a general sense, the invention is based on the recognition that in the system using a trans-cyclooctene moiety as the dienophile, a substantial increase in reaction rate can be obtained if the eight-membered ring moiety is forced into a flattened structure.

According to the invention, this flattened structure is judiciously achieved by providing the trans-cyclooctene moiety with at least two exocyclic bonds fixed in substantially the same plane.

Hereinafter the eight-membered ring moiety will be defined as a trans-cyclooctene moiety, for the sake of legibility, or abbreviated as "TCO" moiety. It will be understood that the essence resides in the possibility of the eight-membered ring to act as a dienophile. The skilled person is familiar with the fact that the dienophile activity is not necessarily dependent on the presence of all carbon atoms in the ring, since also heterocyclic monoalkenylene eight-membered rings are known to possess dienophile activity.

Thus, in general, the invention is not limited to strictly trans-cyclooctene. The person skilled in organic chemistry will be aware that other eight-membered ring-based dienophiles exist, which comprise the same endocyclic double bond as the trans-cyclooctene, but which may have one or more heteroatoms elsewhere in the ring. I.e., the invention generally pertains to eight-membered non-aromatic cyclic alkenylene moieties, preferably a cyclooctene moiety, and more preferably a trans-cyclooctene moiety, comprising at least two exocyclic bonds fixed in the same plane.

Other than is the case with e.g. medicinally active substances, where the in vivo action is often changed with minor structural changes, the present invention first and foremost requires the right chemical reactivity. Thus, the possible structures extend to those of which the skilled person is familiar with their reactivity as a dienophile.

The person skilled in organic chemistry will understand that the term "fixed in substantially the same plane" refers to bonding theory according to which bonds are normally considered to be fixed in the same plane. Typical examples of such fixations in the same plane include double bonds and strained fused rings. E.g., the at least two exocyclic bonds can be the two bonds of a double bond to an oxygen (i.e. C=O). The at least two exocyclic bonds can also be single bonds on two adjacent carbon atoms, provided that these bonds together are part of a fused ring (i.e. fused to the TCO ring) that assumes a substantially flat structure, therewith fixing said two single bonds in substantially one and the same plane. Examples of the latter include strained rings such as cyclopropyl and cyclobutyl.

In yet another example, combining the foregoing possibilities, the fused ring is an aromatic ring. In that case the TCO carbon atoms to which the at least two bonds are attached both are sp2 carbon atoms, and said bonds are part of a fused ring. It will be understood that said bonds take part in the hybridization of the aromatic fused ring.

Without wishing to be bound by theory, the present inventors believe, based on this finding, that the presence of at least two exocyclic bonds in the same plane will result in an at least partial flattening of the TCO ring, and that this flattening in turn provides a key to addressing the need for higher reactivities in pre-targeting on the basis of the retro-Diels-Alder reaction. The partial flattening of the TCO ring is the intrinsic result of the presence of two exocyclic bonds fixed in the same plane, and refers at any rate to the part opposite the endocyclic double bond, i.e. carbon atoms 5 and 6. This holds irrespective of whether the two exocyclic bonds are positioned at carbon atoms 5 and 6 adjacent thereto (4,5), or at carbon atoms 3 and 4.

It should be noted that, depending on the choice of nomenclature, the TCO dienophile may also be denoted E-cyclooctene. With reference to the conventional nomenclature, it will be understood that, as a result of substitution on the cyclooctene ring, depending on the location and molecular weight of the substituent, the same cyclooctene isomer may formally become denoted as a Z-isomer. In the present invention, any substituted variants of the invention, whether or not formally "E" or "Z," or "cis" or "trans" isomers, will be considered derivatives of unsubstituted trans-cyclooctene, or unsubstituted E-cyclooctene. The terms "trans-cyclooctene" (TCO) as well as E-cyclooctene are used interchangeably and are maintained for all dienophiles according to the present invention, also in the event that substituents would formally require the opposite nomenclature. I.e., the invention relates to cyclooctene in which carbon atoms 1 and 6 as numbered below are in the E (entgegen) or trans position.

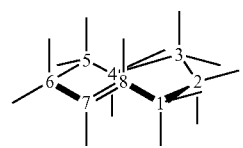

In a broad sense, the invention therefore extends to any substituted TCO moiety that satisfies the aforementioned requirement, provided that it does not contain substituents that would interfere with the TCO ring in its reactivity as a dienophile.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

It is furthermore to be noticed that the term "comprising", used in the description and in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In several chemical formulae reference is made to "alkyl" and "aryl." In this respect "alkyl", each independently, indicates an aliphatic, straight, branched or cyclic alkyl group of up to ten carbon atoms, possibly including 1-3 heteroatoms such as O, N, or S, preferably of 1-6 carbon atoms and "aryl," each independently, indicates an aromatic or heteroaromatic group of up to ten carbon atoms, possibly including 1-3 heteroatoms such as N or S. In several formulae, groups or substituents are indicated with reference to letters such as "A", "B", "X", "Y", and various numbered "R" groups. The definitions of these letters are to be read with reference to each formula, i.e. in different formulae, these letters, each independently, can have different meanings unless indicated otherwise.

Retro Diels-Alder Reaction

The Retro Diels-Alder coupling chemistry generally involves a pair of reactants that couple to form an unstable intermediate, which intermediate eliminates a small molecule (depending on the starting compounds this may be e.g. $N_2$, $CO_2$, RCN, as the sole by-product through a retro Diels-Alder reaction to form a stable product. The paired reactants comprise, as one reactant (i.e. one Bio-orthogonal Reactive Group), a suitable diene, such as a derivative of tetrazine, e.g. an electron-deficient tetrazine and, as the other reactant (i.e. the other Bio-orthogonal Reactive Group), a strained cyclooctene according to formula (1).

Figure 1:
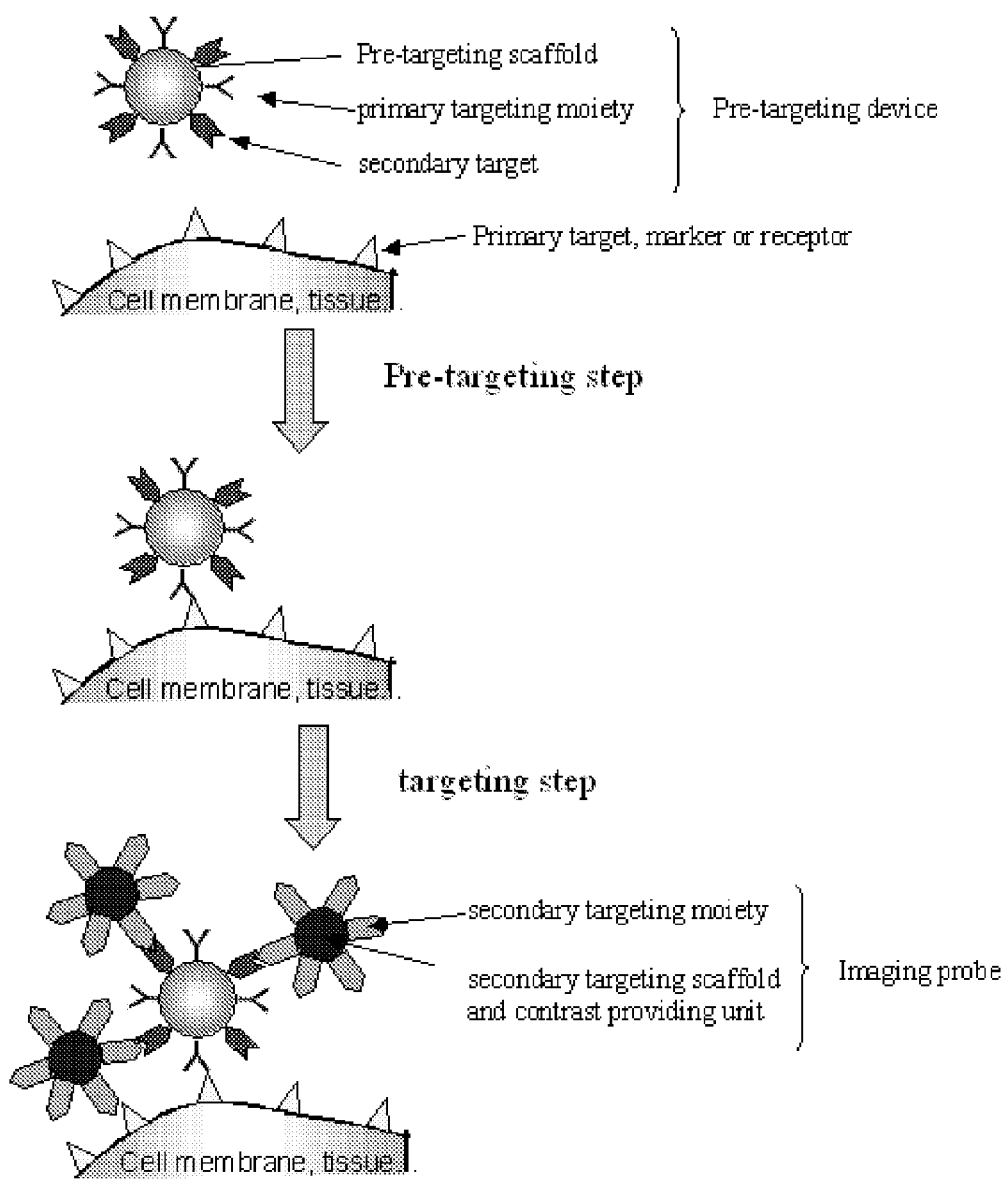
FIG. 1 depicts a general scheme of a pretargeting concept, as discussed above.
Figure 2:
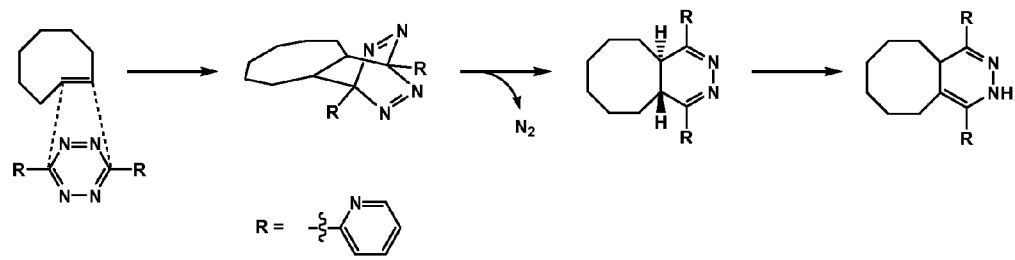
FIG. 2 provides the reaction scheme for a [4+2] Diels-Alder reaction between (3,6)-di-(2-pyridyl)-s-tetrazine and a trans-cyclooctene dienophile, followed by a retro Diels Alder reaction in which the product and dinitrogen is formed. Because the trans cyclooctene derivative does not contain electron withdrawing groups as in the classical Diels Alder reaction, this type of Diels Alder reaction is distinguished from the classical one, and frequently referred to as an "inverse electron demand Diels Alder reaction". In the following text the sequence of both reaction steps, i.e. the initial Diels-Alder cyclo-addition (typically an inverse electron demand Diels Alder cyclo-addition) and the subsequent retro Diels Alder reaction will be referred to in shorthand as "retro Diels Alder reaction" or "retro-DA".

The exceptionally fast reaction of, e.g., electron-deficient (substituted) tetrazines with the flattened TCO moiety of the invention results in a ligation intermediate that rearranges to a stable dihydropyridazine by eliminating $N_2$ as the sole by-product in a [4+2] Retro Diels-Alder cycloaddition. This is shown in FIG. 2.

The two reactive species are abiotic and do not undergo a fast metabolism in vivo. They are bio-orthogonal, e.g. they selectively react with each other in physiologic media. An advantage hereof is that both the diene and the cyclooctene are essentially unreactive toward biomolecules inside or on the surfaces of cells and all other regions like serum etc. Thus, the compounds and the method of the invention can be used in a living cell, tissue or organism. Moreover, the reactive groups are relatively small and can be introduced in biological samples or living organisms without significantly altering the size of biomolecules therein. Using the [4+2] retro Diels-Alder reaction it is possible to bind primary targeting moieties which are large in size, e.g. antibodies, with labels or other molecules using small reaction partners, e.g. tetrazine or cyclooctene. Even more advantageously, primary targeting moieties can be bound which are relatively small, e.g. peptides, with labels or other molecules using (matched) relatively small reaction partners, e.g. tetrazine and cyclooctene. The size and properties of the Pre-targeting Probe and Effector Probe are not greatly affected by the secondary target and secondary targeting moiety, allowing (pre)targeting schemes to be used for small targeting moieties. Because of this, other tissues can be targeted, i.e. the destination of the probes is not limited to the vascular system and interstitial space, as is the case for current pretargeting with antibody-streptavidin.

References on the Inverse electron demand Diels Alder reaction, and the behavior of the pair of reactive species include: Thalhammer, F; Wallfahrer, U; Sauer, J, Tetrahedron Letters, 1990, 31 (47), 6851-6854; Wijnen, J W; Zavarise, S; Engberts, JBFN, Journal Of Organic Chemistry, 1996, 61, 2001-2005; Blackman, M L; Royzen, M; Fox, J M, Journal Of The American Chemical Society, 2008, 130 (41), 13518-19), R. Rossin, P. Renart Verkerk, Sandra M. van den Bosch, R. C. M. Vulders, 1. Verel, J. Lub, M. S. Robillard, Angew Chem Int Ed 2010, 49, 3375, N. K. Devaraj, R. Upadhyay, J. B. Haun, S. A. Hilderbrand, R. Weissleder, Angew Chem Int Ed 2009, 48, 7013, and Devaraj et al., Angew. Chem. Int. Ed., 2009, 48, 1-5.

It will be understood that, in a broad sense, according to the invention the aforementioned coupling chemistry can be applied to basically any pair of molecules, groups, or moieties that are capable of being used in pretargeting. I.e. one of such a pair will comprise a primary targeting moiety, that is capable of binding to a primary target, and further comprises at least one secondary target. The other one will be a secondary targeting moiety suitable for use in binding to said secondary target, and further comprises a moiety suitable for exerting therapeutic action (typically a pharmaceutically active compound), or for being addressed by an imaging technique (i.e. a label), or both.

Figure 3A:
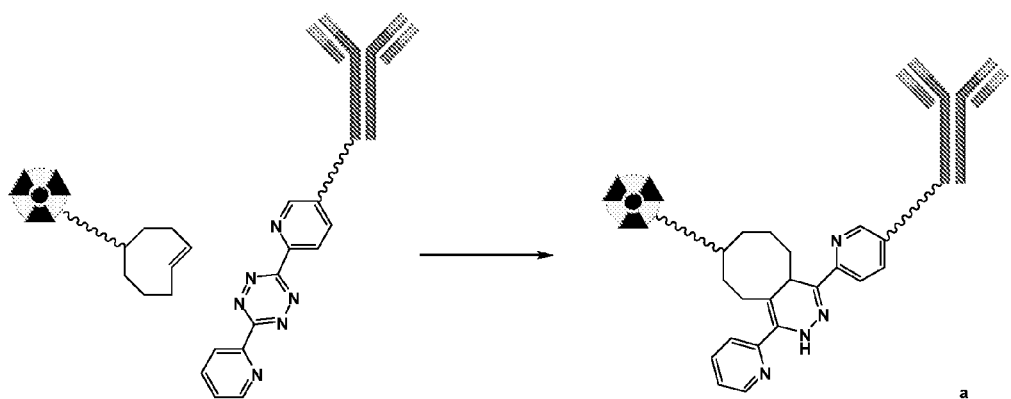
FIG. 3 (a and b) depicts general schemes for pre-targeting using retro Diels-Alder chemistry.
Figure 3B:
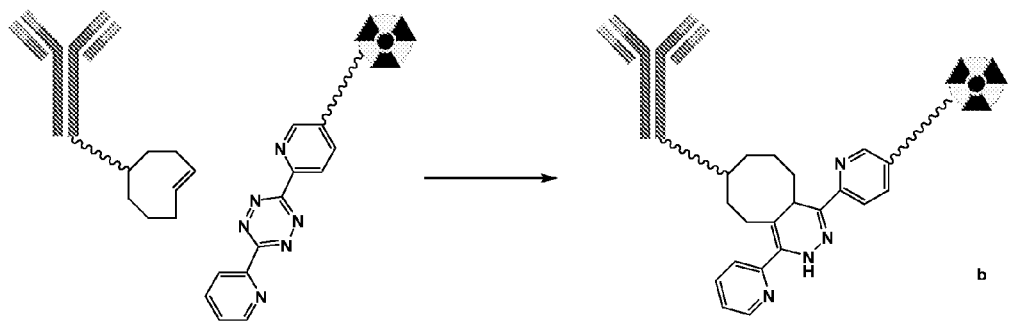
Figure 4:
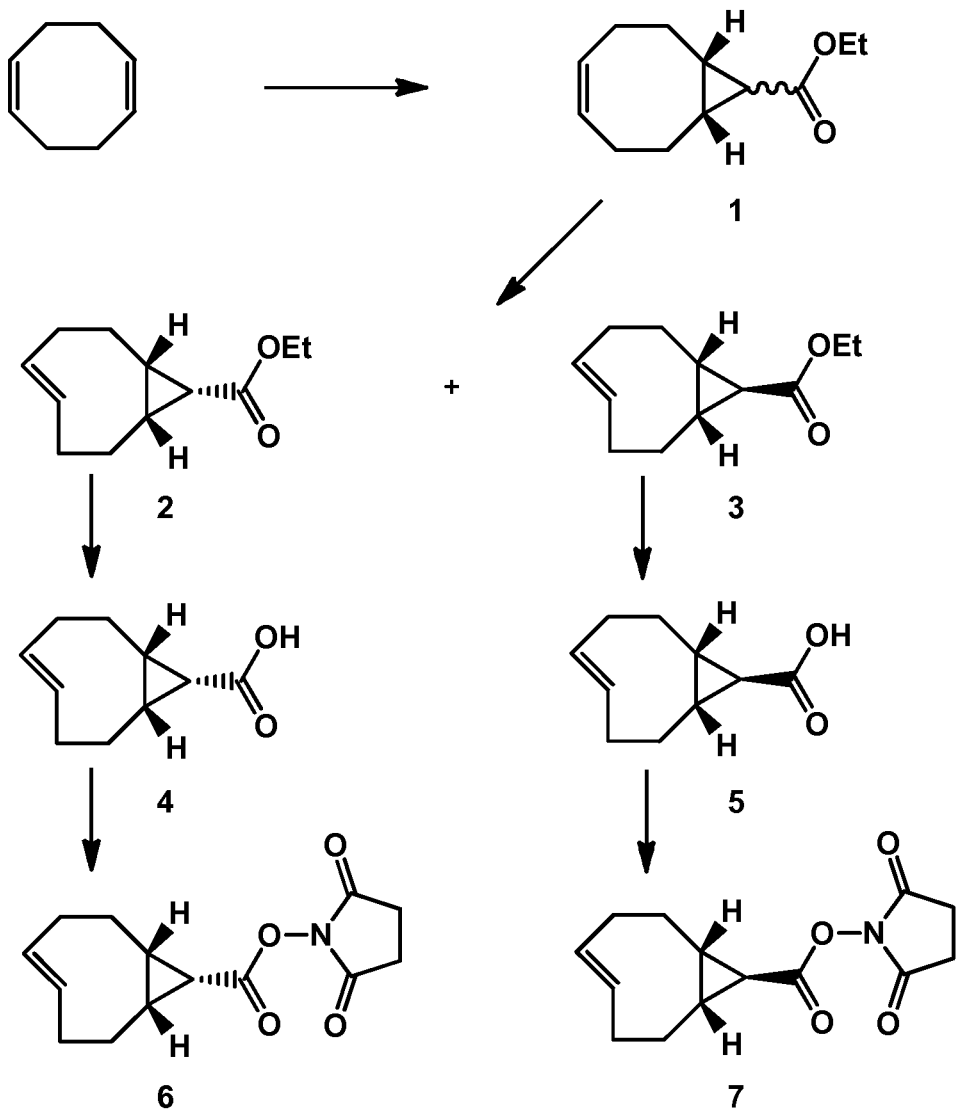
FIG. 4 and FIG. 5 depict the reaction schemes and chemical structures of the compounds referred to in the examples.

Thus, according to the invention, either of the Pre-targeting Probe and the Effector Probe is functionalized with a flattened cyclooctene as defined above, and the other is functionalized with a tetrazine, or other suitable diene. This is illustrated in FIG. 3. The scheme on top (FIG. 3a) indicates a Pre-targeting Probe comprising di-pyridyl tetrazine linked, via a linker moiety (optionally comprising a flexible spacer) to an antibody as the primary targeting moiety, and an Effector Probe comprising cyclooctene (as the secondary targeting moiety) attached, via a linker (a flexible spacer), to a detectable label. The scheme below (FIG. 3b) shows exactly the opposite, viz. a Pre-targeting Probe comprising the cyclooctene and an Effector Probe comprising the tetrazine.

Dienophiles

A fundamental achievement of the present invention, is that a dienophile is selected, viz. a flattened TCO moiety as defined above, that allows achieving increased reaction rates for the bio-orthogonal coupling reaction up to hundred (100) times or more. Or, put otherwise, a reaction time that is only 1% of the time originally required. Or, put still otherwise, the concentration of one reactant can be 100 times lower.

The dienophile, in a broad sense, is an eight-membered non-aromatic cyclic alkenylene moiety (preferably a cyclooctene moiety, and more preferably a trans-cyclooctene moiety), comprising at least two exocyclic bonds fixed in the same plane. This will hereinafter be referred to generally as "Flattened TCO".

Preferably, the flattened TCO satisfies the following formula:

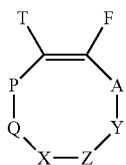

Herein A and P are $CR^a{}_2$; each $R^a$ independently is H or a substituent, preferably H or a substituent selected from the group consisting of alkyl, and aryl, more preferably $C_{1-6}$ alkyl or phenyl).

In an interesting embodiment, Y,Z,X,Q each independently are selected from the group consisting of $CR^a{}_2$, $C=CR^a{}_2$, C=O, C=S, $C=NR^b$, S, SO, $SO_2$, O, $NR^b$, and $SiR^c{}_2$, with at least one and at most four of Y, Z, X, and Q being selected from the group consisting of $C=CR^a{}_2$, C=O, C=S, and $C=NR^b$ and with the proviso that no adjacent pairs of atoms are present selected from the group consisting of O—O, O—$NR^b$, S—$NR^b$, O—S, O—S(O), O—S(O)$_2$, and S—S, and such that Si is only adjacent to $CR^a{}_2$ or O.

In another interesting embodiment, one of the bonds PQ, QX, XZ, ZY, YA is part of a fused ring or consists of $CR^a=CR^a$, provided that PQ and YA are not part of an aromatic 5- or 6-membered ring, of a conjugated 7-membered ring, or of $CR^a=CR^a$; the remaining groups (A,Y,Z,X,Q,P) being independently from each other $CR^a{}_2$, $C=CR^a{}_2$, C=O, C=S, $C=NR^b$, S, SO, $SO_2$, O, $NR^b$, $SiR^c{}_2$, such that P, A are $CR^a{}_2$, with at most 2 groups being $C=CR^a{}_2$, C=O, C=S, $C=NR^b$, and no adjacent pairs of atoms are present selected from the group consisting of O—O, O—$NR^b$, S—NR, O—S, O—S(O), O—S(O)$_2$, and S—S, and such that Si, if present, is adjacent to $CR^a{}_2$ or O, and the $CR^a=CR^a$ bond, if present, is adjacent to $CR^a{}_2$ or $C=CR^a{}_2$ groups;

In yet another interesting embodiment, two of the bonds PQ, QX, XZ, ZY, YA are part of a fused ring or consist of $CR^a=CR^a$, provided that PQ and YA are not part of an aromatic 5- or 6-membered ring, of a conjugated 7-membered ring or of $CR^a=CR^a$; the remaining groups (A,Y,Z,X,Q,P) being independently from each other $CR^a{}_2$, S, SO, $SO_2$, O, $NR^b$, $SiR^c{}_2$, such that P, A are $CR^a{}_2$, with the proviso that no adjacent pairs of atoms are present selected from the group consisting of O—O, O—$NR^b$, S—NR, O—S, O—S(O), O—S(O)$_2$, and S—S, and such that Si, if present, is adjacent to $CR^a{}_2$ or O, and the $CR^a=CR^a$ bond, if present, is adjacent to $CR^a{}_2$ or $C=CR^a{}_2$ groups.

T, F each independently denote H, or a substituent selected from the group consisting of alkyl, F, Cl, Br, or I.

In some embodiments fused rings are present, which are selected from fused 3-membered rings, fused 4-membered rings, fused bicyclic 7-membered rings, fused aromatic 5-membered rings, fused aromatic 6-membered rings, and fused planar conjugated 7-membered rings as defined below:
Fused 3-membered rings are:

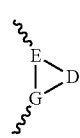

Therein E, G are part of the above mentioned 8-membered ring and can be fused to PQ, QP, QX, XQ, XZ, ZX, ZY, YZ, YA, AY, such that P, A are C or $CR^a$ E-G is $CR^a$—$CR^a$, and D is $CR^a{}_2$, C=O, C=S, $C=NR^b$, $NR^b$, O, S E-G is $CR^a$—N, and D is $CR^a{}_2$, C=O, C=S, $C=NR^b$, $NR^b$, O, S Fused 4-membered rings are:

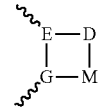

E-G is part of the above mentioned 8-membered ring and can be fused to PQ, QP, QX, XQ, XZ, ZX, ZY, YZ, YA, AY, such that P, A are C or $CR^a$ E,G are $CR^a$ or N, and D,M independently from each other are $CR^a{}_2$, C=O, C=S, $C=NR^b$, $C=CR^a{}_2$, S, SO, $SO_2$, O, $NR^b$ but no adjacent O—O or S—S groups.

E-D is $C=CR^a$ and G is N, $CR^a$, and M is $CR^a{}_2$, S, SO, $SO_2$, O, $NR^b$ E-D is C=N and G is N, $CR^a$, and M is $CR^a{}_2$, S, SO, $SO_2$, O D-M is $CR^a=CR^a$ and E, G independently from each other are $CR^a$, N D-M is $CR^a=N$ and E is $CR^a$, N, and G is $CR^a$ E is C, G is $CR^a$ or N, and D, M are $CR^a{}_2$, S, SO, $SO_2$, O, $NR^b$, or max 1 of C=O, C=S, $C=NR^b$, $C=CR^a{}_2$, but no adjacent O—O or S—S groups E,G are C and D,M independently from each other are $CR^a{}_2$, S, SO, $SO_2$, O, $NR^b$ but no adjacent O—O, or S—S groups.

Fused bicyclic 7-membered rings are:

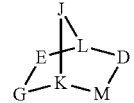

E-G is part of the above mentioned 8-membered ring and can be fused to PQ, QP, QX, XQ, XZ, ZX, ZY, YZ, YA, AY, such that P, A are C or $CR^a$ E,G are C, $CR^a$ or N; K, L are $CR^a$; D,M form a $CR^a=CR^a$ or $CR^a=N$, or D,M independently from each other are $CR^a{}_2$, C=O, C=S, $C=NR^b$, $C=CR^a{}_2$, S, SO, $SO_2$, O, $NR^b$ but no adjacent O—O, S—S, N—S groups; J is $CR^a{}_2$, C=O, C=S, $C=NR^b$, $C=CR^a{}_2$, S, SO, $SO_2$, O, $NR^b$; max 2 N groups E,G are C, $CR^a$; K is N and L is $CR^a$; D,M form a $CR^a=CR^a$ bond or D,M independently from each other are $CR^a{}_2$, C=O, C=S, $C=NR^b$, $C=CR^a{}_2$, $NR^b$ but no adjacent O—O, S—S, N—S groups; J is $CR^a{}_2$, C=O, C=S, $C=NR^b$, $C=CR^a{}_2$, S, SO, $SO_2$, O, $NR^b$; max 2 N groups E,G are C, $CR^a$; K and L are N; D,M, J independently from each other are $CR^a{}_2$, C=O, C=S, $C=NR^b$, $C=CR^a{}_2$ groups Fused aromatic 5-membered rings are

E, G are part of the above mentioned 8-membered ring and can be fused to PQ, QP, QX, XQ, XZ, ZX, ZY, YZ, YA, AY E,G is C. One of the groups L, K, or M are O, NR$^b$, S and the remaining two groups are independently from each other CR$^a$ or N.

E is C and G is N. L, K, M are independently from each other CR$^a$ or N.

Fused aromatic 6-membered rings are:

E, G are part of the above mentioned 8-membered ring and can be fused to PQ, QP, QX, XQ, XZ, ZX, ZY, YZ, YA, AY E,G is C. L, K, D, M are independently from each other CR$^a$ or N Fused planar conjugated 7-membered rings are

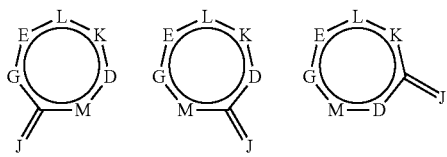

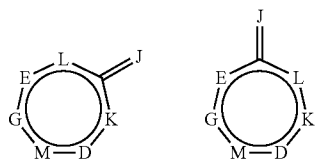

E, G are part of the above mentioned 8-membered ring and can be fused to PQ, QP, QX, XQ, XZ, ZX, ZY, YZ, YA, AY E,G is C; L, K, D, M are CR$^a$; J is S, O, CR$^a_2$, NR$^b$.

In all of the above embodiments, one of A, P, Q, Y, X, and Z, or the substituents or fused rings of which they are part, is bound, optionally via a spacer, to the Pre-targeting Probe or the Effector Probe.

Each R$^a$ as above-indicated can independently be H, alkyl, O-alkyl, O-aryl, S-aryl, S-alkyl, S(O)-aryl, S(O)-alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl, OCS-aryl, SCS-alkyl, SCS-aryl, F, Cl, Br, I, N$_3$, SO$_2$H, SO$_3$H, SO$_4$H, PO$_4$H, OH, SH, NO$_2$, NO, CN, OCN, SCN, NCO, NCS, CF$_3$, NR'R" with R' and R" each independently being H, alkyl or aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl, CR'NR" with R' and R" each independently being H, alkyl or aryl.

Each R$^b$ as above indicated is selected from the group consisting of H, alkyl, aryl, O-aryl, O-alkyl, OH, C(=O)NR'R" with R' and R" each independently being H, aryl or alkyl, R'CO-alkyl with R' being H, alkyl, and aryl; Each R$^c$ as above indicated is selected from the group consisting of H, alkyl, aryl, O-alkyl, O-aryl, OH;

wherein two or more R$^{a,b,c}$ moieties together may form a ring;

In a preferred embodiment, the trans-cyclooctene moiety satisfies formula (1):

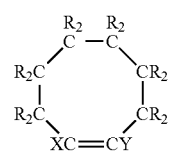

(1)

wherein, in addition to the presence of at least two exocyclic bonds fixed in the same plane, each R independently denotes H, or, in at most six instances, a substituent selected from the group consisting of alkyl, O-alkyl, S— Aryl, alkyl, O-aryl, O-alkyl, S-aryl, S-alkyl, S(O)-aryl, S(O)-alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl, OCS-aryl, SCS-alkyl, SCS-aryl, F, Cl, Br, I, SO$_2$, SO$_3$, SO$_4$, OH, SH, NO$_2$, CN, NR'R" with R' and R" each independently being H or alkyl, aryl, C(=O)O-alkyl, C(=O)O-aryl, C(=S)O-alkyl, C(=S)O-aryl, C(=O)S-alkyl, C(=O)S-aryl, C(=S) S-alkyl, C(=S)S-aryl, C(=O)NR'R" with R' and R" each independently being H, aryl or alkyl, R'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl; wherein two R moieties together may form a ring;

with at least one R comprised in a linker moiety, optionally via a spacer, to the Pre-targeting Probe or the Effector Probe, and wherein X and Y each independently denote H, or a substituent selected from the group consisting of alkyl, F, Cl, Br, and I.

In the foregoing dienophiles, it is preferred that the at least two exocyclic bonds fixed in the same plane are selected from the group consisting of (a) the single bonds of a fused cyclopropyl ring, (b) the single bonds of a fused cyclobutyl ring, (c) the hybridized bonds of a fused aromatic ring, (d) an exocyclic double bond to an oxygen, and (e) an exocyclic double bond to a carbon.

In a further preferred embodiment, the dienophile is a compound selected from the following structures:

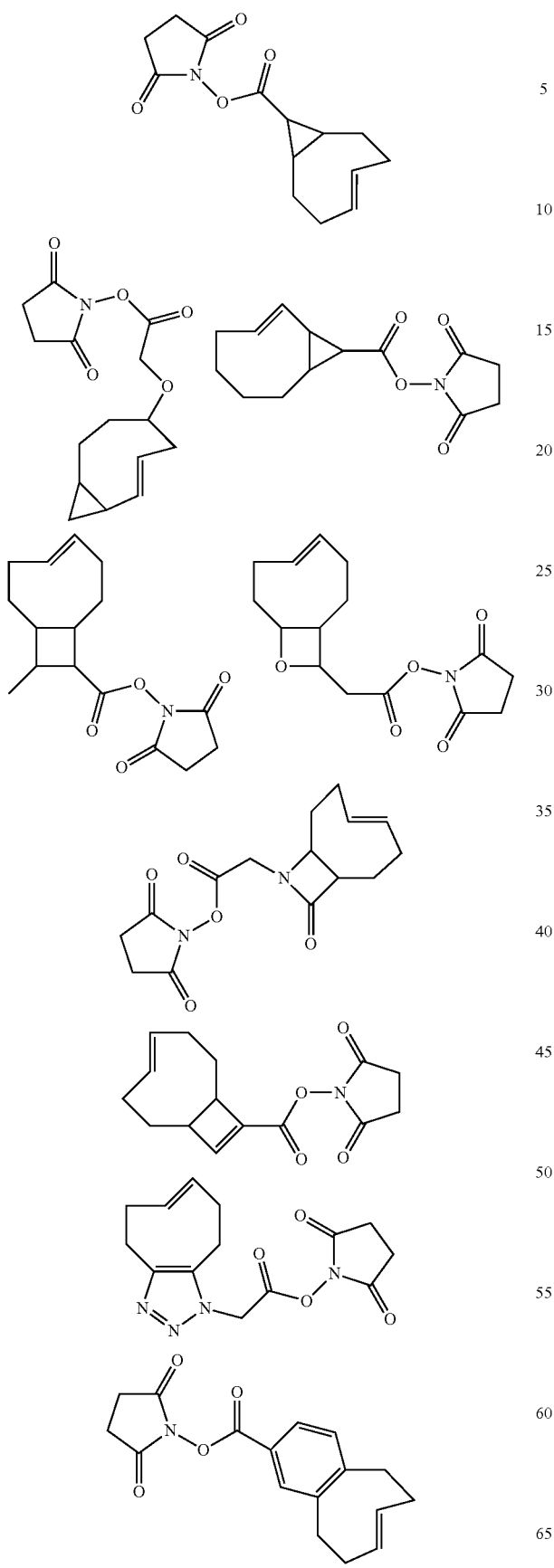
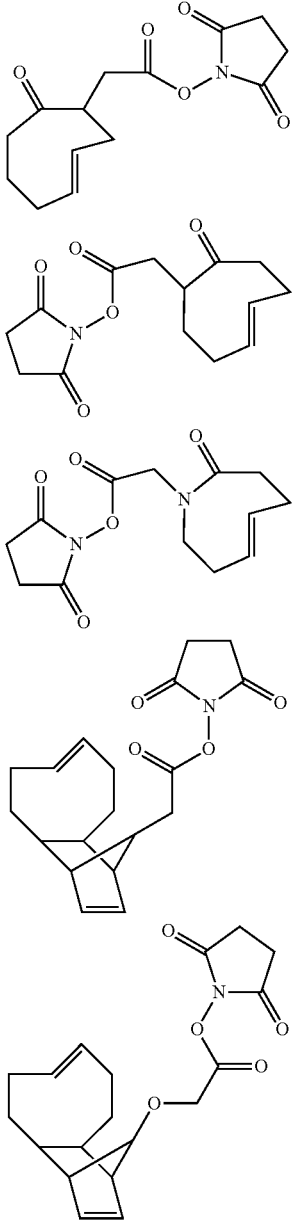

It is noted that the foregoing structures are generally selected, apart from their judicious flattened dienophile structure, on the basis of structural moieties (in ring and in substituents) that are synthetically accessible to the skilled organic chemist.

In another interesting embodiment, the dienophile is a compound selected from the following structures:

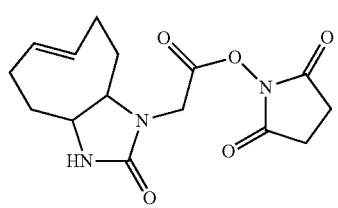

-continued

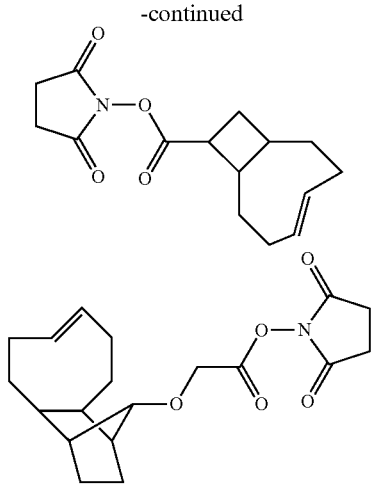

The above dienophiles are depicted here in the forms of esters of N-hydroxy succinimide (NHS-esters). NHS-esters are commonly used for protein modification, and here serve as a tool for coupling the TCO to a Targeting Moiety or an Effector Moiety.

For illustration purposes the TCO structures can also be depicted without specific reference to NHS. Taking into account the description of the invention, wherein the TCO moiety is comprised in a Pre-Targeting Probe or an Effector Probe, for the aforementioned compounds this can be illustrated as follows:

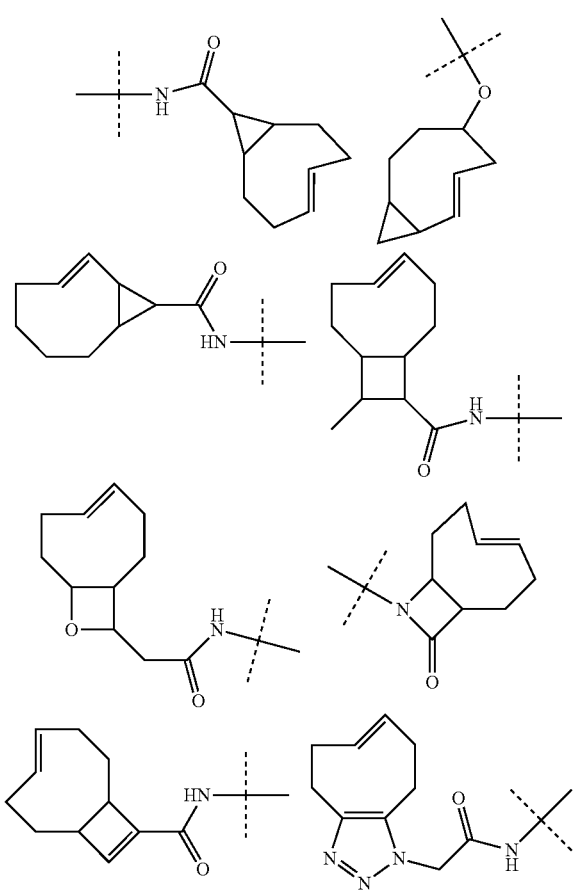

-continued

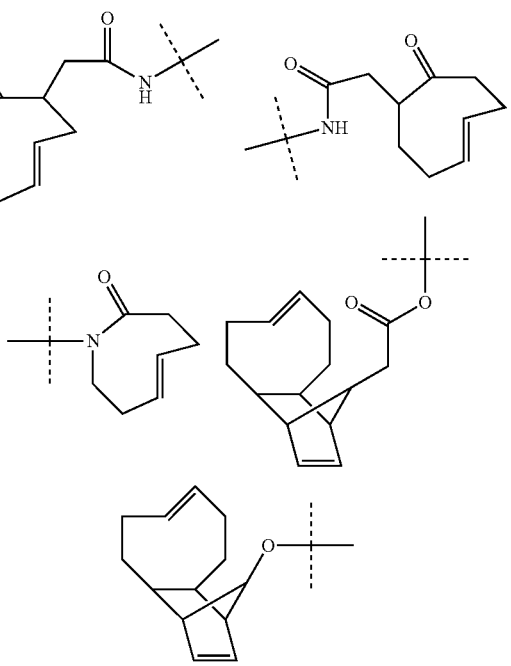

- - - =(rest of) attached Primary Targeting Moiety or Effector Moiety, optionally attached via a linker The dienophiles for use in the invention can be synthesized by the skilled person, on the basis of known synthesis routes to cyclo-octenes and corresponding hetero atom(s)-containing rings. The substitutions required to obtain two exocyclic bonds fixed in the same plane can be carried out by techniques known to the skilled organic chemist. Suitable starting compounds include the following precursors, indicated below with literature references:

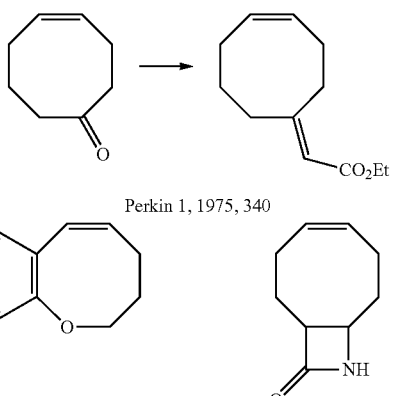

Perkin 1, 1975, 340

J. Org. Chem. 1974, 39, 3038    Chem. Pharm. Bull. 2001, 49, 1178

-continued

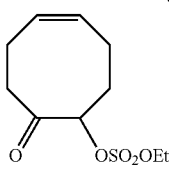 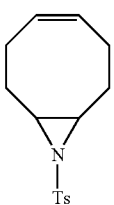

J. Org. Chem. 1999, 64, 7121    J. Org. Chem. 2006, 71 1653

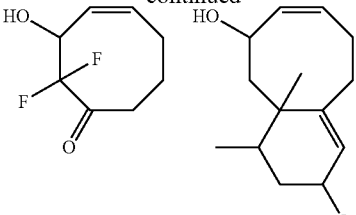

J. Am. Chem. Soc. 1977, 99, 834    J. Am. Chem. Soc. 1979, 101, 5283

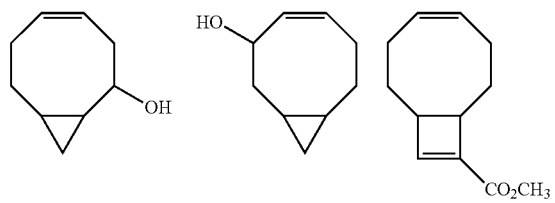

Tetrahedron Asymmetry 2001, 12, 643    J. Prakt. Chem. 1988, 330, 683

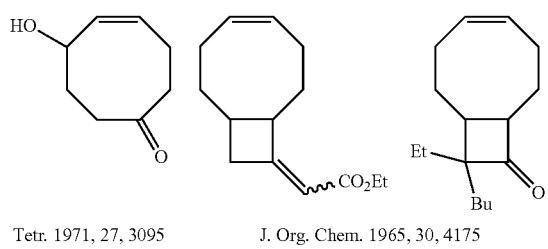

Tetr. 1971, 27, 3095    J. Org. Chem. 1965, 30, 4175

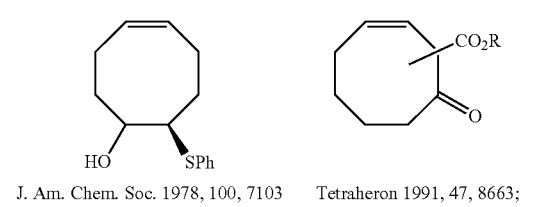

J. Am. Chem. Soc. 1978, 100, 7103    Tetraheron 1991, 47, 8663; J. Org. Chem. 1998, 63, 7945

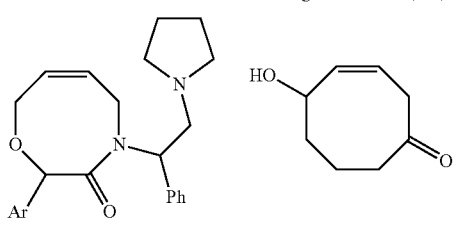

US patent 2004/209857    Tetrahedron 1997, 53, 1855

-continued

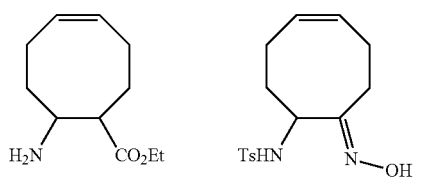

J. Org. Chem. 2007, 72, 1575; Org. Biomol. Chem. 2005, 3, 2701    J. Org. Chem. 1991, 56, 3988

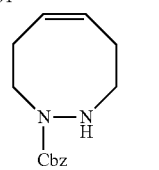

Tet. Let. 2004, 45, 3757

The skilled person further is aware of the wealth of cyclooctene derivatives that can be synthesized via the ring closing metathesis reaction using Grubbs catalysts.

As mentioned above, the TCO possibly includes one or more heteroatoms in the ring. This is as such sufficiently accessible to the skilled person. Reference is made, e.g., to the presence of a thioether in TCO: Cere et al. *Journal of Organic Chemistry* 1980, 45, 261. Also, e.g., an —O—SiR$_2$—O moiety in TCO: Prevost et al. *Journal of the American Chemical Society* 2009, 131, 14182

Dienes

The person skilled in the art is aware of the wealth of dienes that are reactive in the Retro Diels-Alder reaction. Preferred dienes are given below, with reference to formulae (2)-(5).

(2)

wherein $R^1$ is selected from the group consisting of alkyl, aryl, $CF_3$, $CF_2$—R', C(=O)R', C(=S)R', C(=O)O—R', C(=O)S—R', C(=S)O—R', C(=S)S—R', C(=O)NR'R'', C(=S)NR'R'', NR'C(=O)R'', NR'C(=S)R'', NR'C(=O)OR'', NR'C(=S)OR'', NR'C(=O)SR'', NR'C(=S)SR'', NR'C(=O)NR''R''', NR'C(=S)N'R''R''' with R', R'', and R'' each independently being H, aryl or alkyl; A and B each independently are selected from the group consisting of alkyl-substituted carbon, aryl substituted carbon, nitrogen, $N^+O^-$, $N^+R$ with R being alkyl, with the proviso that A and B are not both carbon; X is selected from the group consisting of O, N-alkyl, and C=O, and Y is CR with R being selected from the group consisting of H, alkyl, aryl, C(=O)OR', C(=O)SR', C(=S)OR', C(=S)SR', C(=O)NR'R'' with R' and R'' each independently being H, aryl or alkyl.

A diene particularly suitable as a reaction partner for cyclooctene is:

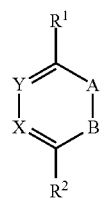

(3)

wherein $R^1$ and $R^2$ each independently are selected from the group consisting of H, alkyl, aryl, $CF_3$, $CF_2$—R', $NO_2$, OR', SR', C(=O)R', C(=S)R', OC(=O)R'', SC(=O)R'', OC(=S)R'', SC(=S)R''', S(=O)R', S(=O)$_2$R''', C(=O) O—R', C(=O)S—R', C(=S)O—R', C(=S)S—R', C(=O)NR'R'', C(=S)NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR'R'', NR'C(=S)N'R'R'' with R' and R'' each independently being H, aryl or alkyl, and R' independently being aryl or alkyl A is selected from the group consisting of N-alkyl, N-aryl, C=O, and CN-alkyl; B is O; X is selected from the group consisting of N, CH, C-alkyl, C-aryl, CC(=O)R', CC(=S)R', CS(=O)R', CS(=O)$_2$R''', CC(=O)O—R', CC(=O)S—R', CC(=S)O—R', CC(=S)S—R', CC(=O)NR'R'', CC(=S)NR'R'', R' and R'' each independently being H, aryl or alkyl and R' independently being aryl or alkyl; Y is selected from the group consisting of CH, C-alkyl, C-aryl, N, and N$^+$O$^-$.

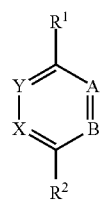

(4)

Another diene particularly suitable as a reaction partner for cyclooctene is: wherein $R^1$ and $R^2$ each independently are selected from the group consisting of H, alkyl, aryl, $CF_3$, $CF_2$—R', $NO_2$, OR', SR', C(=O)R', C(=S)R', OC(=O)R''', SC(=O)R''', OC(=S)R'', SC(=S)R'', S(=O)R', S(=O)$_2$R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR'R'', NR'C(=S)N'R'R'' with R' and R'' each independently being H, aryl or alkyl, and R' independently being aryl or alkyl; A is selected from the group consisting of N, C-alkyl, C-aryl, and N$^+$O$^-$; B is N; X is selected from the group consisting of N, CH, C-alkyl, C-aryl, CC(=O)R', CC(=S)R', CS(=O)R', CS(=O)$_2$R''', CC(=O)O—R', CC(=O)S—R', CC(=S)O—R', CC(=S)S—R', CC(=O)NR'R'', CC(=S)NR'R'', R' and R'' each independently being H, aryl or alkyl and R''' independently being aryl or alkyl; Y is selected from the group consisting of CH, C-alkyl, C-aryl, N, and N$^+$O$^-$.

Particularly useful tetrazine derivatives are electron-deficient tetrazines, i.e. tetrazines substituted with groups or moieties that do not generally hold as electron-donating, and preferably carrying electron-withdrawing substituents.

These electron-deficient tetrazines generally satisfy the following structural formula:

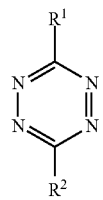

(5)

Herein $R^1$ and $R^2$ each independently denote a substituent selected from the group consisting of 2-pyridyl, 3, pyridyl, 4-pyridyl, 2,6-pyrimidyl, 3,5-pyrimidyl, 2,4-pyrimidyl, or phenyl, optionally substituted with one or more electron-withdrawing groups such as $NO_2$, F, Cl, $CF_3$, CN, COOH, COOR, $CONH_2$, CONHR, $CONR_2$, CHO, COR, $SO_2R$, $SO_2OR$, NO, Ar, wherein R is $C_1$-$C_6$ alkyl and Ar stands for an aromatic group, particularly phenyl, pyridyl, or naphthyl.

In the compounds according to each of the formulae (2)-(5), the $R^1$ and $R^2$ groups (including those on X or Y), can further be provided with suitable linker or spacer moieties as discussed below. Analogously, and independently thereof, also the dienophile of formula (1) as defined above can further be provided with suitable linker or spacer moieties as discussed below.

It will be understood that the diene, in all embodiments, will comprise at least one linkage, optionally via a spacer, to the Pre-targeting Probe or the Effector Probe.

According to one embodiment, the invention is used for targeted imaging.

According to this embodiment, imaging of a specific primary target is achieved by specific binding of the primary targeting moiety of the Pre-targeting Probe and detection of this binding using detectable labels comprised in the Effector Probe.

The dienes for use in the invention can be synthesized by the skilled person, on the basis of synthesis routes known to the skilled organic chemist.

Primary Target

A "primary target" as used in the present invention relates to a target to be detected in a diagnostic and/or imaging method, and/or to be modulated, bound, or otherwise addressed by a pharmaceutically active compound, or other therapeutic modality.

The primary target can be selected from any suitable targets within the human or animal body or on a pathogen or parasite, e.g. a group comprising cells such as cell membranes and cell walls, receptors such as cell membrane receptors, intracellular structures such as Golgi bodies or mitochondria, enzymes, receptors, DNA, RNA, viruses or viral particles, antibodies, proteins, carbohydrates, monosaccharides, polysaccharides, cytokines, hormones, steroids, somatostatin receptor, monoamine oxidase, muscarinic receptors, myocardial sympatic nerve system, leukotriene receptors, e.g. on leukocytes, urokinase plasminogen activator receptor (uPAR), folate receptor, apoptosis marker, (anti-) angiogenesis marker, gastrin receptor, dopaminergic system, serotonergic system, GABAergic system, adrenergic system, cholinergic system, opoid receptors, GPIIb/IIIa receptor and other thrombus related receptors, fibrin, calcitonin receptor, tuftsin receptor, integrin receptor, VEGF/EGF receptors, EGF, matrix metalloproteinase (MMP), P/E/L-selectin receptor, LDL receptor, P-glycoprotein, neurotensin receptors, neuropeptide receptors, substance P receptors, NK receptor, CCK receptors, sigma receptors, interleukin receptors, herpes simplex virus tyrosine kinase, human tyrosine kinase.

According to a particular embodiment of the present invention, the primary target is a protein such as a receptor. Alternatively, the primary target may be a metabolic pathway, which is upregulated during a disease, e.g. infection or cancer, such as DNA synthesis, protein synthesis, membrane synthesis and carbohydrate uptake. In diseased tissues, above-mentioned markers can differ from healthy tissue and offer unique possibilities for early detection, specific diagnosis and therapy, especially targeted therapy.

Pre-Targeting Probe

A Pre-targeting Probe comprises a moiety that is capable of binding to the primary target of interest.

Targeting moieties are typically constructs that have affinity for cell surface targets (e.g., membrane receptors), structural proteins (e.g., amyloid plaques), or intracellular targets (e.g., RNA, DNA, enzymes, cell signaling pathways). These moieties can be antibodies (fragments), proteins, aptamers, oligopeptides, oligonucleotides, oligosaccharides, as well as peptides, peptoids and organic drug compounds known to accumulate at a particular disease or malfunction.

Particular embodiments of suitable primary targeting moieties for use in the kits of the present invention are described herein and include receptor binding peptides and antibodies. A particular embodiment of the present invention relates to the use of small targeting moieties, such as peptides, so as to obtain a cell-permeable targeting probe.

A "primary targeting moiety" as used in the present invention relates to the part of the targeting probe which binds to a primary target. Particular examples of primary targeting moieties are peptides or proteins which bind to a receptor. Other examples of primary targeting moieties are antibodies or fragments thereof, which bind to a cellular compound. Antibodies can be raised to non-proteinaceous compounds as well as to proteins or peptides. Other primary targeting moieties can be made up of aptamers, oligopeptides, oligonucleotides, oligosaccharides, as well as peptoids and organic drug compounds. A primary targeting moiety preferably binds with high specificity, with a high affinity, optionally even covalently, and the bond with the primary target is preferably stable within the body.

In order to allow specific targeting of the above-listed primary targets, the primary targeting moiety of the targeting probe can comprise compounds including but not limited to antibodies, antibody fragments, e.g. Fab2, Fab, scFV, diabodies, polymers (tumor targeting by virtue of EPR effect), proteins, peptides, e.g. octreotide and derivatives, VIP, MSH, LHRH, chemotactic peptides, bombesin, elastin, peptide mimetics, carbohydrates, monosaccharides, polysaccharides, viruses, whole cells, phage, drugs, chemotherapeutic agents, receptor agonists and antagonists, cytokines, hormones, steroids. Examples of organic compounds envisaged within the context of the present invention are, or are derived from, estrogens, e.g. estradiol, androgens, progestins, corticosteroids, paclitaxel, etoposide, doxorubricin, methotrexate, folic acid, and cholesterol.

According to a particular embodiment of the present invention, the primary target is a receptor and suitable primary targeting moieties include but are not limited to, the ligand of such a receptor or a part thereof, which still binds to the receptor, e.g. a receptor binding peptide in the case of receptor binding protein ligands.

Other examples of primary targeting moieties of protein nature include interferons, e.g. alpha, beta, and gamma interferon, interleukins, and protein growth factor, such as tumor growth factor, e.g. alpha, beta tumor growth factor, platelet-derived growth factor (PDGF), uPAR targeting protein, apolipoprotein, LDL, annexin V, endostatin, and angiostatin.

Alternative examples of primary targeting moieties include DNA, RNA, PNA and LNA which are e.g. complementary to the primary target.

According to a particular embodiment of the invention, small lipophilic primary targeting moieties are used which can bind to an intracellular primary target.

According to a further particular embodiment of the invention, the primary target and primary targeting moiety are selected so as to result in the specific or increased targeting of a tissue or disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme. This can be achieved by selecting primary targets with tissue-, cell- or disease-specific expression. For example, membrane folic acid receptors mediate intracellular accumulation of folate and its analogs, such as methotrexate. Expression is limited in normal tissues, but receptors are overexpressed in various tumor cell types.

According to one embodiment, the Pre-targeting Probe and the Effector Probe can be multimeric compounds, comprising a plurality of primary and/or secondary targets and/or targeting moieties. These multimeric compounds can be polymers, dendrimers, liposomes, polymer particles, or other polymeric constructs. Of particular interest for amplifying the signal of detection are targeting probes with more than one secondary target, which allow the binding of several Effector Probes.

The Pre-targeting Probe further comprises the above-mentioned first Bio-orthogonal Reactive group. This group serves as a "secondary target", i.e. as the part of the targeting probe that provides the first reaction partner for the retro Diels-Alder coupling chemistry.

Said secondary target can be either partner of the coupling reaction, as described above. I.e. in one embodiment it is an electron-deficient tetrazine. In another embodiment it is a flattened TCO as described above in accordance with the present invention.

In the Pre-targeting Probe, the primary targeting moiety and the first Bio-orthogonal Reactive Group can be directly linked to each other. They can also be bound to each other via a linker, and furthermore they can both be linked to a primary targeting scaffold, e.g. a biopolymer such as a polypeptide. I.e. in the most simple sense, the Linker Moiety is a bond. Suitable Linker Moieties further include, but are not limited to polyethylene glycol (PEG) chains varying from 2 to 200, particularly 3 to 113 and preferably 5-50 repeating units. By adjusting the PEG chain length, one can influence the circulation time of the probes in the physiological system. This is of particular relevance for the Pre-targeting Probe (as the initial targeting step of linking the primary targeting moiety to the primary target may involve a relatively slow process, requiring a relatively lengthy circulation time). Linker moieties optionally include biopolymer fragments, such as oligo- or polypeptides or polylactides.

It will be understood that the invention encompasses any conceivable manner in which the diene and the dienophile are attached to either of the pre-targeting or effector probes.

Methods of affecting conjugation to these probes, e.g. through reactive amino acids such as lysine or cysteine, are known to the skilled person.

Effector Probe

An Effector Probe comprises an Effector Moiety that is capable of providing the desired diagnostic, imaging, and/or therapeutic effect. The Effector Probe further comprises a secondary targeting moiety.

The secondary targeting moiety relates to the part of the Effector Probe that forms the reaction partner for the available secondary target, i.e. the Bio-orthogonal Reactive Group (or groups) comprised in the Pre-targeting Probe. It will be understood that, to the extent that the secondary target is a Flattened TCO of formula (1) as defined above, the secondary targeting moiety will be a diene such as a tetrazine, and vice versa.

The Effector Moiety can, e.g., be a detectable label. A "detectable label" as used herein relates to the part of the Effector Probe which allows detection of the probe, e.g. when present in a cell, tissue or organism. One type of detectable label envisaged within the context of the present invention is a contrast providing agent. Different types of detectable labels are envisaged within the context of the present invention and are described hereinbelow.

Thus, according to a particular embodiment of the present invention, the pretargeting kits and methods of the present invention are used in imaging, especially medical imaging. In order to identify the primary target, use is made, as the Effector Probe, of an imaging probe comprising one or more detectable labels. Particular examples of detectable labels of the imaging probe are contrast-providing moieties used in traditional imaging systems such as MRI-imageable constructs, spin labels, optical labels, ultrasound-responsive constructs, X-ray-responsive moieties, radionuclides, (bio) luminescent and FRET-type dyes. Exemplary detectable labels envisaged within the context of the present invention include, and are not necessarily limited to, fluorescent molecules, e.g. autofluorescent molecules, molecules that fluoresce upon contact with a reagent, etc., radioactive labels; biotin, e.g., to be detected through binding of biotin by avidin; fluorescent tags, imaging constructs for MRI comprising paramagnetic metal, imaging reagents, e.g., those described in U.S. Pat. Nos. 4,741,900 and 5,326,856) and the like. The radionuclide used for imaging can be, for example, an isotope selected from the group consisting of $^{3}$H, $^{11}$C, $^{13}$N, $^{15}$O, $^{18}$F, $^{19}$F, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{75}$Br, $^{76}$Br, $^{77}$Br, $^{80}$Br, $^{82}$Br, $^{82}$Rb, $^{86}$Y, $^{88}$Y, $^{89}$Sr, $^{89}$Zr, $^{97}$Ru, $^{99}$Tc, $^{110}$In, $^{111}$In, $^{113}$In, $^{114}$In, $^{117}$Sn, $^{120}$I, $^{122}$Xe, $^{123}$I, $^{124}$I, $^{125}$I, $^{166}$Ho, $^{167}$Tm, $^{169}$Yb, $^{193}$Pt, $^{195}$Pt, $^{201}$Tl, and $^{203}$Pb.

Other elements and isotopes, such as being used for therapy may also be applied for imaging in certain applications.

The MRI-imageable moiety can be, for example, a paramagnetic ion or a superparamagnetic particle. The paramagnetic ion can be an element selected from the group consisting of Gd, Fe, Mn, Cr, Co, Ni, Cu, Pr, Nd, Yb, Tb, Dy, Ho, Er, Sm, Eu, Ti, Pa, La, Sc, V, Mo, Ru, Ce, Dy, Tl. The ultrasound responsive moiety can comprise a microbubble, the shell of which consisting of a phospholipid, and/or (biodegradable) polymer, and/or human serum albumin. The microbubble can be filled with fluorinated gasses or liquids.

The X-ray-responsive moieties include but are not limited to iodine, barium, barium sulfate, gastrografin or can comprise a vesicle, liposome or polymer capsule filled with iodine compounds and/or barium sulfate.

Moreover, detectable labels envisaged within the context of the present invention also include peptides or polypeptides that can be detected by antibody binding, e.g., by binding of a detectable labeled antibody or by detection of bound antibody through a sandwich-type assay. In one embodiment the detectable labels are small size organic PET and SPECT labels, such as $^{18}$F, $^{11}$C or $^{123}$I. Due to their small size, organic PET or SPECT labels are ideally suited for monitoring intracellular events as they do not greatly affect the properties of the targeting device in general and its membrane transport in particular. An imaging probe comprising a PET label and either of the retro Diels-Alder active moieties as a secondary targeting moiety is lipophilic and able to passively diffuse in and out of cells until it finds its binding partner. Moreover, both components do not preclude crossing of the blood brain barrier and thus allow imaging of regions in the brain.

When the Effector Probe is intended to comprise a detectable label based on a metal, such as a lanthanide (e.g. Gd) for MRI contrast enhancement, such is preferably provided in the form of a chelate. In such a case the Effector Probe preferably comprises a structural moiety capable of forming a coordination complex with such a metal. A good example hereof are macrocyclic lanthanide(III) chelates derived from 1,4,7,10-tetraazacyclododecane-1,4,7,10-tetraacetic acid (H$_4$dota), and 1,4,7,10-tetraazacyclododecane-α,α',α,"α'"-tetramethyl-1,4,7,10-tetraacetic acid (H$_4$dotma).

The Effector Moiety can also be a therapeutic moiety such as a pharmaceutically active compound. Examples of pharmaceutically active compounds are provided herein. A therapeutic probe can optionally also comprise a detectable label.

Thus, according to another embodiment, the pretargeting kits and methods of the invention are used for targeted therapy. This is achieved by making use of an Effector Probe comprising a secondary targeting moiety and one or more pharmaceutically active agents (i.e. a drug, toxin or a radioactive isotope for radiation therapy). Suitable drugs for use in the context of targeted drug delivery are known in the art. Optionally, the therapeutic probe can also comprise a detectable label, such as one or more imaging agents. A radionuclide used for therapy can be, for example, an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{111}$In, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, and $^{225}$Ac.

Alternatively the drug in the therapeutic probe is selected from sensitizers for photodynamic therapy.

Alternatively the therapeutic probe comprises a recognition moiety that binds to therapeutic entities in vivo, such as T cells, natural killer cells, or other endogenous constructs such as proteins.

In the Effector Probe, the secondary targeting moiety, i.e. the second Bio-orthogonal Reactive Group and the effector moiety can be directly linked to each other. They can also be bound to each other via a linker, and furthermore they can both be linked to a secondary targeting scaffold. The linker can, independently, be selected from the same moieties, e.g. poly ethylene glycols, as discussed above. The secondary targeting scaffold can be e.g. a biopolymer such as a polypeptide.

The invention also relates to a pre-targeting method, using the retro Diels-Alder reaction. Herein a Pre-targeting Probe comprising a primary targeting moiety (e.g., an antibody, and antibody fragment, or a receptor binding peptide), functionalized with a suitable diene, preferably a compound according to any one of the formulae (2)-(5) mentioned above, or with a cyclooctene according to formula (1) above, respectively, is injected into a subject. After binding to the target (e.g. a primary or metastatic tumor lesion, an atherosclerotic plaque, an infracted area, an inflammation or infection site, etc.) and clearance from the circulation and from non-target tissues (e.g. blood, liver, spleen, kidney, etc.) an Effector Probe comprising a secondary targeting moiety, e.g. carrying an E-cyclooctene or tetrazine derivative, respectively (i.e. the reactive counterpart of the Bioorthogonal Reactive Group present in the Pre-targeting Probe), and a drug or an imageable label, is injected. The Effector Probe binds to the primary targeting moiety and provides high contrast or selectively treats the disease site.

The invention also relates to the targeting of a general metabolic pathway, which is upregulated during a disease (like infection or cancer) such as DNA, protein, and membrane synthesis and carbohydrate uptake. Suitable probes comprise diene or dienophile labeled amino acids, sugars, nucleic acids and choline, analogous to the metabolic tracers currently used in the art, [$^{11}$C]-methionine, [$^{18}$F]-fluorodeoxyglucose (FDG), deoxy-[$^{18}$F]-fluorothymidine (FLT) and [$^{11}$C]-choline. Cells with a high metabolism or proliferation have a higher uptake of these building blocks. In this method, e.g. tetrazine- or E-cyclooctene derivatives enter these or other pathways and accumulate in and/or on cells. After sufficient build-up and clearance of free probe a detectably labeled or drug-carrying (cell permeable) tetrazine probe or E-cyclooctene probe (or probes carrying other dienes/dienophiles according to the invention) is sent in to bind the accumulated E-cyclooctene, respectively tetrazine metabolite. As an advantage over normal FDG (fluorine 18 fluorodeoxyglucose)-type imaging, ample time is available to allow high build up of the targeting moiety before radioactivity is sent in, thus increasing the target to non-target ratio. Alternatively, a metabolic pathway and/or metabolite that is specific for a disease can be targeted.

The invention also relates to the pre-targeting of intracellular targets. Due to their small size, organic PET labels ($^{18}$F, $^{11}$C) are ideally suited for monitoring intracellular events as they do not greatly affect the properties of the targeting device in general and its membrane transport in particular (contrary to the large and polar radiometal-chelate construct conjugates). Although the substituted tetrazine moiety and the E-cyclooctene used in the invention are not necessarily small, they are relatively nonpolar and can be used for intracellular imaging of proteins, mRNA, signaling pathways etc. The secondary (e.g. PET labeled) substituted tetrazine moiety or E-cyclooctene probe (i.e. the Effector Probe) is capable of passively diffusing in and out of cells until it finds its binding partner or is subject to an active uptake mechanism. These properties also allow the use of retro Diels-Alder reaction for pre-targeting in the brain, as both components do not preclude crossing of the blood brain barrier.

The invention also pertains to pretargeted signal amplification and/or polyvalency installation. At least one primary targeting device is conjugated to a dendrimer, polymer, liposome, or nanoparticle containing multiple tetrazine moieties. After receptor binding, a (one or more) cyclooctene conjugated to one or more contrast moieties for nuclear imaging (e.g., a radiometal chelate, a radiohalogen, etc.) or MRI (e.g., Gd chelates) is injected. The subsequent retro Diels-Alder reaction results in a high concentration of MRI contrast agent at the target tissue. Furthermore, the polyvalency at the target site will increase the reaction kinetics with the Flattened TCO effector conjugate, affording an efficient target accumulation of for example MRI contrast agents. Naturally, the Flattened TCO can also be used in the targeting device conjugate and the tetrazine (or other diene of the invention) conjugated to the effector.

Conjugation Route and Kits

The invention further pertains to the use of the retro Diels-Alder reaction as a route for the conjugation of imaging agents and drugs to targeting constructs such as peptides. The effector can contain organic PET or SPECT nuclide labeled prosthetic groups, metal complexes for PET/SPECT/MRI and microbubbles for ultrasound imaging, fluorophores for optical imaging, but also α and β$^-$ emitters for radiotherapy and, in general, a cytotoxic anticancer agent. The imaging/therapy agents can be functionalized with a pendant tetrazine or other suitable diene moiety and the targeting group with a flattened TCO derivative, or vice versa.

The present route is especially advantageous for agents for nuclear imaging and radiotherapy: in view of the decay of the radionuclide it is beneficial to conduct the most time-consuming step (the actual targeting in the body of a subject) as a pre-targeting step. The selection, according to the invention, of Flattened TCO, to attain the above-described very rapid retro Diels-Alder chemistry for the secondary targeting, allows for using a broad range of radionuclides, including shorter lived ones than with existing methods. Flattened TCO functionalized Effector Probes and suitable dienes, e.g., tetrazine carrying Pre-targeting Probes can be coupled at extremely low concentrations in vivo without the need for sustained blood circulation of the effector moiety (such as the radionuclide). It will be understood that this equally holds for Flattened TCO carrying Pre-targeting Probes combined with diene, particularly tetrazine, functionalized Effector Probes. Moreover, the reactive groups are advantageously stable, and thus present a longer lived reactivity, without being too easily prone to side reactions.

It will be understood that the foregoing provides advantages such as minimizing the radiation dose to the patient. Also, it leads to allowing the usage of PET i.e. Positron Emission Tomography agents instead of SPECT i.e. Single Photon Emission Computerized Tomography agents. Furthermore, the increased reactivity allows applications at lower concentrations in vivo.

The present invention is particularly suitable for use in multimodal imaging, optionally using different imaging agents to visualize the same target. Alternatively the imaging probe comprises at least 2 different labels to enable multimodal imaging.

The application of the improved [4+2] retro Diels-Alder chemistry of the invention in molecular imaging opens up pre-targeting to all types and sizes of targeting constructs. This allows intracellular and metabolic imaging to profit from the high target accumulation and low background, attainable through pre-targeting build-up. Likewise, pretargeted signal amplification schemes, e.g. polytetrazine and/or polyalkene dendrimers or liposomes, become available for smaller and more diverse targeting devices.

As the reaction partners are abiotic and bio-orthogonal, pre-targeting using the [4+2] retro Diels-Alder reaction using Flattened TCO as the dienophile as described above, is not hampered by endogenous competition and metabolism/decomposition, and affords a stable covalent bond. Choosing a target metabolic pathway, and the corresponding tetrazine-metabolite derivative by virtue of its high flux in, for example, tumor cells compared to normal cells, affords the installation of a high density of artificial tetrazine receptors or other chemical handles in cells or on the surfaces of target cells, circumventing the use of endogenous cell surface receptors which can sometimes be at low levels.

Further particular embodiments of the present invention relate to kits comprising a metabolic precursor and an imaging probe, more particularly an imaging probe comprising a detectable label, which is a contrast agent used in traditional imaging systems. Such a detectable label can be but is not limited to a label selected from the group consisting of MRI-imageable constructs, spin labels, optical labels, ultrasound-responsive agents, X-ray-responsive agents, radionuclides, and FRET-type dyes. In a particular embodiment of the present invention, use is made of reporter probes. Such a reporter probe can be the substrate of an enzyme, more particularly an enzyme which is not endogenous to the cell, but has been introduced by way of gene therapy or infection with a foreign agent. Non-endogenous as referring to a gene in a cell or tissue herein is used to indicate that the gene is not naturally present and/or expressed in that cell or tissue. Alternatively, such a reporter probe is a molecule which is introduced into the cell by way of a receptor or a pump, which can be endogenous or introduced into the cell by way of gene therapy or infection with a foreign agent. Alternatively, the reporter probe is a molecule which reacts to certain (changing) conditions within a cell or tissue environment.

The invention also includes agents for use in the kits described above. One such agent is a pretargeting agent comprising a primary targeting moiety and a bio-orthogonal reactive group, wherein the bio-orthogonal reactive group is a reaction partner for a [4+2] retro Diels-Alder reaction. Particular reaction partners are described hereinbefore, i.e. generally either an electron-deficient tetrazine or other suitable diene as discussed above, or a flattened cyclooctene in accordance with the invention. The invention also relates to the use of these agents in targeted medical imaging or targeted therapy, and to said agents for use in such a method. Particularly, the invention relates to these use of these agents in a pretargeting method, and to these agents for use in such a method. Another such agent is an imaging probe comprising a detectable label and a bio-orthogonal reactive group, wherein the bio-orthogonal reactive group is a reaction partner for a [4+2] retro Diels-Alder reaction.

The invention also relates to an imaging probe comprising a detectable label and a bio-orthogonal reactive group, wherein the bio-orthogonal reactive group is a reaction partner for a [4+2] retro Diels-Alder reaction. The invention further relates to a therapeutic probe comprising a pharmaceutically active compound and a bio-orthogonal reactive group, wherein the bio-orthogonal reactive group is a reaction partner for a [4+2] retro Diels-Alder reaction.

Part of the invention is also a pretargeting method comprising administering a pretargeting agent as described above to a subject and allowing the agent to circulate in the subject's system for a period of time effective to achieve binding of the primary targeting moiety to a primary target, followed by clearing non-bound agent from the body, optionally by means of a clearing agent. A typical time period for this is 12 to 96 hours, particularly around 48 hours.

Further, the invention provides an imaging method comprising conducting a pretargeting method as described above, followed by the administration of an imaging probe also according to the invention, wherein the bio-orthogonal reactive groups in the pretargeting agent and in the imaging probe together form the reactive partners for the [4+2] retro Diels-Alder reaction. Similarly, the invention provides a method of targeted medical treatment in a subject, comprising conducting a pretargeting method as described above, followed by the administration of a therapeutic probe also according to the invention, wherein the bio-orthogonal reactive groups in the pretargeting agent and in the imaging probe together form the reactive partners for the [4+2] retro Diels-Alder reaction.

The invention also pertains to the aforementioned pretargeting agents for use in an imaging or therapeutic method as described above.

In summary, on the basis of retro Diels-Alder chemistry, bio-orthogonal pretargeted molecular imaging and therapy serves to bring great advantages to patients. On one side, it serves to afford the acquisition of superior images of target tissues such as cancer and cardiovascular lesions. On the other hand, the intrinsic side effects deriving from the administration of radioactive compounds and, in general, potentially toxic drugs can be greatly diminished while increasing the effective dose that reaches a diseased tissue. Furthermore, it will greatly expand the collection of traceable molecular events that underlie disease. In particular, this technology can give access to target tissues far from blood vessels and will facilitate imaging of the information-rich intracellular environment.

The invention will be illustrated with reference to the following, non-limiting Examples and the accompanying non-limiting Figures.

EXAMPLES

Materials:

All reagents and solvents were obtained from commercial sources (Sigma-Aldrich, Acros, Biosolve, ABCR, Invitrogen, and Merck for reagents, Biosolve, Merck and Cambridge Isotope Laboratories for normal and deuterated solvents) and used without further purification unless stated otherwise. [$^{177}$Lu]Lutetium chloride solutions were purchased from PerkinElmer. Water was distilled and deionized (18 MΩcm) by means of a milli-Q water filtration system (Millipore). The labeling buffers were treated with Chelex-100 resin (BioRad) overnight, then filtered through 0.22 μm and stored at 4° C. Gelcode blue protein staining solution was purchased from Pierce Protein Research (Thermo Fisher Scientific). Amicon Ultra-4 centrifugal filter units (50 kDa MW cut-off) were purchased from Millipore. Tablets to prepare phosphate buffered saline (PBS) pH 7.4 were acquired from Calbiochem (Merck).

Methods:

NMR spectra were recorded in $CDCl_3$, using a Bruker DPX300 spectrometer. $^{13}C$ NMR multiplicities (q=quaternary, t=tertiary, s=secondary and p=primary) were distinguished using a DEPT pulse sequence. $^1H$ chemical shifts were determined with the aid of 2D-CH correlation spectra.

Preparative column chromatography was performed on a Combiflash Companion apparatus (Teledyne Isco) using SiliCycle silica columns. Preparative HPLC was performed using an Agilent 1200 apparatus, equipped with a Zorbax C18 column (21.2×150 mm, 5 μm particles) applying a gradient of water and MeCN containing 0.1% TFA. Analytical radio-HPLC was carried out on an Agilent 1100 system equipped with a Gabi radioactive detector (Raytest). The samples were loaded on a Zorbax Eclipse XDB-C18 column (4.6×150 mm, 5 μm particles), which was eluted at 1 mL/min with a linear gradient of MeCN in water containing 0.1% TFA (2 min at 10% MeCN followed by an increase to 45% MeCN in 11 min). The UV wavelength was preset at 254 nm. Size exclusion (SEC) HPLC was carried out on an Agilent 1200 system equipped with a Gabi radioactive detector. The samples were loaded on a Superdex-200 10/300 GL column (GE Healthcare Life Sciences) and eluted with 10 mM phosphate buffer, pH 7.4, at 0.5 mL/min. The UV wavelength was preset at 260 and 280 nm.

Figure 5:
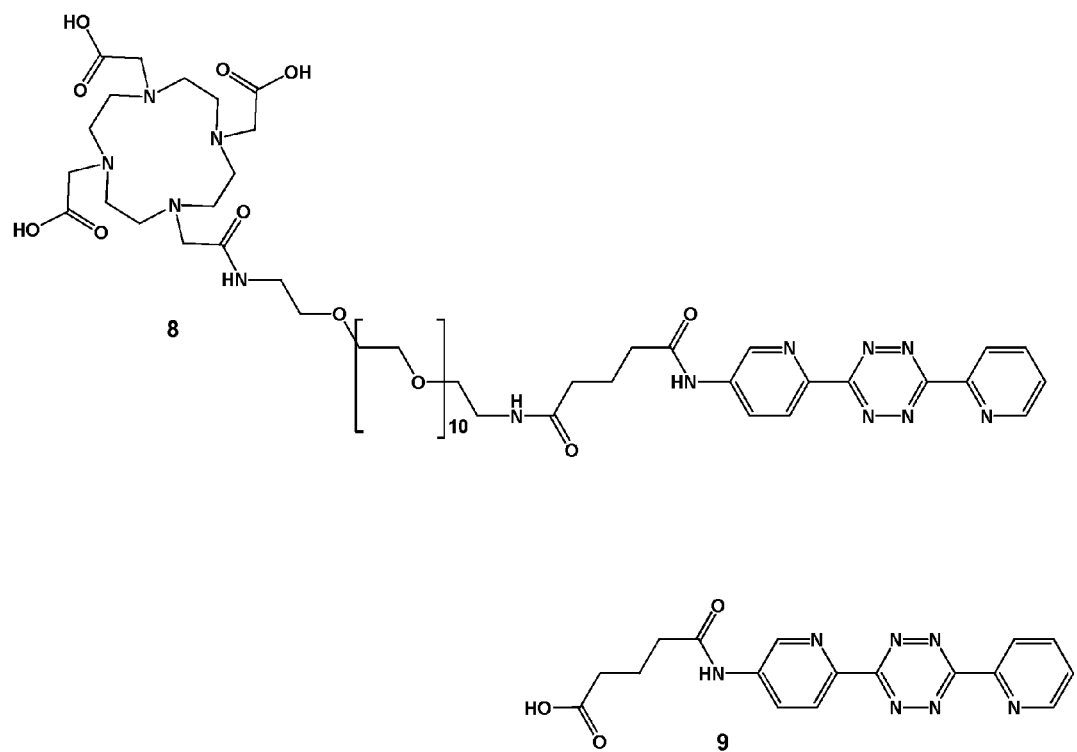

Synthesis and radio labeling of DOTA-tetrazine 8 (FIG. 5) were performed as described in Rossin et al., Angew Chem Int Ed 2010, 49, 3375-8. The $^{177}$Lu-labeling yields were determined by radio-TLC, using ITLC-SG strips (Varian) eluted with 200 mM EDTA in 0.9% aq. NaCl and imaged on a phosphor imager (FLA-7000, Fujifilm). In these conditions, free $^{177}$Lu migrates with $R_f$=0.9, while $^{177}$Lu-DOTA-tetrazine remains at the origin.

SDS-PAGE was performed on a Phastgel system using 7.5% PAGE homogeneous gels (GE Healthcare Life Sciences). Gel radiographies were imaged on a phosphor imager analyzed with the AIDA software (Advanced Image Data Analyzer). The protein MW standard solution (Precision Plus dual color standard) was purchased from BioRad. Upon electrophoresis, the gels were stained for 2 h with gelcode blue, destained overnight in water and then digitized with a conventional flat bed scanner.

The concentration of CC49 solutions were determined with a NanoDrop 1000 spectrophotometer (Thermo Fisher Scientific) from the absorbance at 322 nm and 280 nm, respectively.

Example 1

Synthesis of (E-endo)-2,5-dioxopyrrolidin-1-yl bicyclo[6.1.0]non-4-ene-9-carboxylate (6) and (E-exo)-2,5-dioxopyrrolidin-1-yl bicyclo[6.1.0]non-4-ene-9-carboxylate (7)

Compound 1 was synthesized following Dommerholt et al. *Angew. Chem. Int. Ed.* 2010, 49, 9422-9425

(Z)-ethyl bicyclo[6.1.0]non-4-ene-9-carboxylate (1)

To a solution of 1,5-cyclooctadiene (18.5 mL, 150 mmol) and rhodium(II)acetate dimer (cat. amount) in $CH_2Cl_2$ (10 mL) was added slowly a solution of 15% ethyl diazoacetate (2.0 mL, 18.8 mmol) in $CH_2Cl_2$ (20 mL) over a period of 3.5 h while cooling in an icebath. After addition the reaction mixture was warmed to RT. After 1.5 h the reaction was complete according to NMR analysis and the mixture was filtered over a silicagel plug and washed with $CH_2Cl_2$. The filtrate was concentrated until all $CH_2Cl_2$ was removed and then diluted with heptane. The solution was eluted over a filter with silicagel with heptane (500 mL) and with MTBE (400 mL). The MTBE fraction contained the product, which was further purified by column chromatography ($SiO_2$, heptane/EtOAc gradient 0% to 4%). The compound 1 (2.50 g, 12.9 mmol, 68% yield) was obtained as a colorless oil as a mixture of endo/exo isomers.

(E-endo)-Ethyl bicyclo[6.1.0]non-4-ene-9-carboxylate (2)

To a reactor, filled with a heptane/$Et_2O$ mixture (1:1, approx. 650 mL), was added a solution of 1 (2.50 g, 12.9 mmol) and methyl benzoate (1.6 mL, 12.7 mmol) in heptane/$Et_2O$. The reaction mixture was irradiated with a tungsten lamp and at the same time pumped through a column containing 10% w/w $AgNO_3$ impregnated silicagel (22 g). After 16 h of irradiation an almost full conversion was obtained and the column was washed with MTBE (500 mL). The column was washed with a 10% MeOH/MTBE mixture, which was concentrated, treated with ammonia and extracted with $CH_2Cl_2$ to afford an amount of the E isomers (651 mg). The column material was further treated with ammonia and extracted with $CH_2Cl_2$ to afford more of the E isomers (498 mg).

The combined mixtures of E isomers were purified by column chromatography ($SiO_2$, heptane/EtOAc 3%) to afford product 2 (319 mg, 1.6 mmol, 13% yield) as a colorless oil and its isomer 3.

(E-exo)-Ethyl bicyclo[6.1.0]non-4-ene-9-carboxylate (3)

This compound was obtained in 23% yield (568 mg, 2.9 mmol) as a colorless oil after chromatographic separation in the previous experiment.

(E-endo)-Bicyclo[6.1.0]non-4-ene-9-carboxylic acid (4)

To a solution of 2 (319 mg, 1.64 mmol) in methanol (3.0 mL) was added a solution of lithium hydroxide monohydrate (275 mg, 6.6 mmol) in water (1.5 mL). The mixture was heated to 45° C. for 2 h and then stirred at 30° C. overnight. The reaction was further heated to 45° C. for 6 h until a complete conversion was observed by TLC analysis. The mixture was concentrated, diluted with water and MTBE and was then neutralized with an aqueous citric acid solution. After extraction with MTBE (3×), drying with $Na_2SO_4$ and evaporation of the solvent, compound 4 (269 mg, 1.62 mmol, 99% yield) was obtained as a white solid.

(E-exo)-Bicyclo[6.1.0]non-4-ene-9-carboxylic acid (5)

To a solution of 3 (568 mg, 2.92 mmol) in methanol (6.0 mL) was added a solution of lithium hydroxide monohydrate (487 mg, 11.61 mmol) in water (2.0 mL). The mixture was heated to 45° C. for 2 h and then stirred at 30° C. for 16 h until a complete conversion was observed by TLC analysis. The mixture was concentrated, diluted with water and MTBE and was then neutralized with an aqueous citric acid solution. After extraction with MTBE (3×), drying with $Na_2SO_4$ and evaporation of the solvent, compound 5 (440 mg, 2.65 mmol, 91% yield) was obtained as a yellowish crystalline solid.

(E-endo)-2,5-Dioxopyrrolidin-1-yl bicyclo[6.1.0]non-4-ene-9-carboxylate (6)

A solution of 4 (269 mg, 1.62 mmol) and N-hydroxysuccinimide (224 mg, 1.95 mmol) in THF (10 mL) was cooled in an ice-bath and a solution of DCC (335 mg, 1.62 mmol) in THF (2 mL) was added. The ice-bath was removed and the mixture was stirred 16 h at RT. The white suspension was diluted with MTBE, filtered over a glass filter and washed with MTBE. The filtrate was concentrated in vacuo. Purification by column chromatography ($SiO_2$, heptane/EtOAc gradient 10%-40%) afforded 6 (290 mg, 1.10 mmol, 68% yield) as a white crystalline solid. $^1$H NMR (300 MHz, $CDCl_3$): δ=5.77 (m, 1H), 5.25 (m, 1H), 2.82 (s, 4H), 2.41 (m, 1H), 2.34 (m, 1H), 2.11 (m, 1H), 2.09 (t, 1H, J=8.4 Hz), 2.04 (m, 1H), 1.98 (m, 1H), 1.95 (m, 1H), 1.6-1.2 (m, 4H);

$^{13}$C NMR (75 MHz, CDCl$_3$): δ=169.6 (q), 166.9 (q), 137.5 (t), 132.5 (t), 33.2 (s), 32.9 (s), 25.6 (t), 26.7 (s), 26.8 (s), 25.8 (t), 25.7 (s), 18.0 (t).

(E-exo)-2,5-Dioxopyrrolidin-1-yl bicyclo[6.1.0]non-4-ene-9-carboxylate (7)

A solution of 5 (440 mg, 2.65 mmol) and N-hydroxysuccinimide (366 mg, 3.18 mmol) in THF (17 mL) was cooled in an ice-bath and a solution of DCC (546 mg, 2.65 mmol) in THF (2 mL) was added. The ice-bath was removed and the mixture was stirred 16 h at RT. The white suspension was diluted with MTBE, filtered over a glass filter and washed with MTBE. The filtrate was concentrated in vacuo. Purification by column chromatography (SiO$_2$, heptane/EtOAc gradient 10%-60%) afforded 7 (553 mg, 2.10 mmol, 79% yield) as a white crystalline solid. $^1$H NMR (300 MHz, CDCl$_3$): δ=5.88 (m, 1H), 5.20 (m, 1H), 2.82 (s, 4H), 2.5-2.3 (m, 4H), 2.00 (m, 2H), 1.49 (m, 1H), 1.40 (m, 1H), 1.23 (t, 1H, J=5.7 Hz), 0.92 (m, 1H), 0.70 (m, 1H); $^{13}$C NMR (75 MHz, CDCl$_3$): δ=169.8 (q), 169.4 (q), 137.9 (t), 132.0 (t), 38.0 (s), 33.1 (s), 31.9 (s), 29.2 (t), 28.2 (t), 26.9 (s), 25.5 (s), 23.9 (t).

Example 2

Antibody Modification with endo- and exo-E-2,5-dioxopyrrolidin-1-yl bicyclo[6.1.0]non-4-ene-9-carboxylate (6 and 7)

Figure 6:
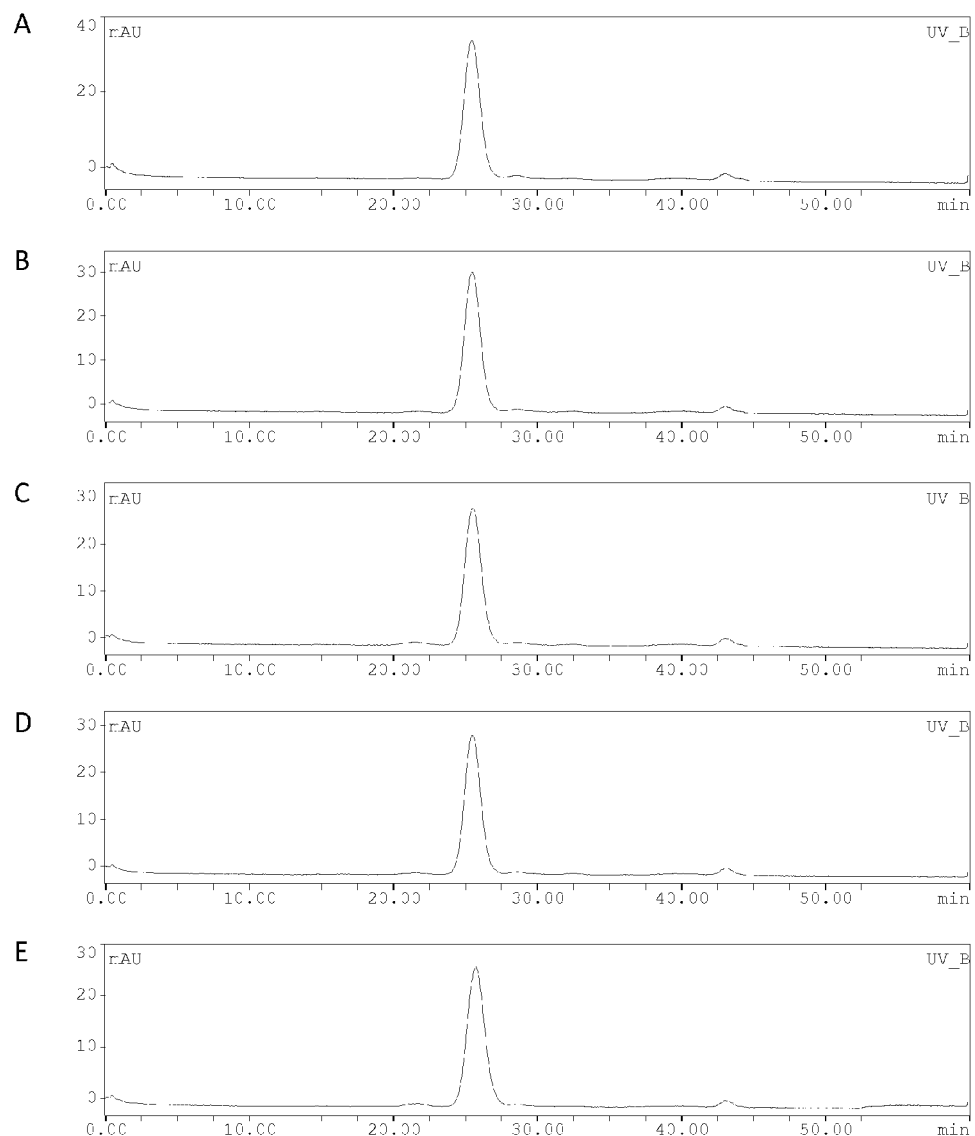
FIG. 6 depicts the SEC-HPLC chromatograms of (A) native CC49, CC49 modified with (B) 0.4 or (C) 5.2 equivalents endo-TCO moieties (6) and CC49 modified with (D) 0.7 or (E) 8.9 equivalents exo-TCO moieties (7) per molecule (UV profiles at 260 nm).
Figure 7:
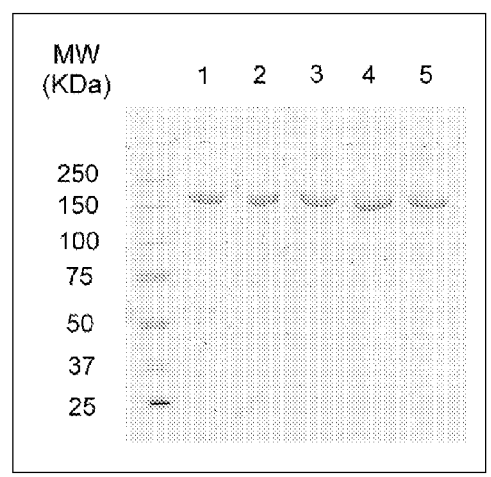
FIG. 7 depicts the SDS-PAGE analysis of CC49-TCO constructs. Lanes 1 to five contain native CC49, CC49 modified with 0.4 and 5.2 endo-TCO moieties 6 and CC49 functionalized with 0.7 and 8.9 exo-TCO moieties 7, respectively (full length gel, MW standards on the left).
Figure 8:
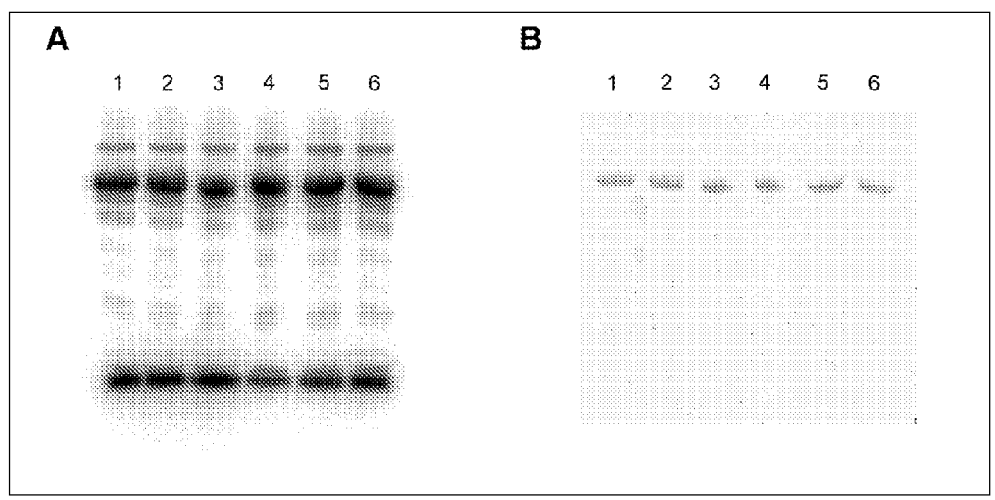
FIG. 8 depicts the SDS-PAGE analysis of the reaction mixtures for TCO quantification with $^{177}$Lu-DOTA-tetrazine titration described in Example 2 (A: gel radiography; B: protein stain). Lanes 1 to 3 contain mixtures of CC49-TCO-6 and $^{177}$Lu-DOTA tetrazine (10, 12, and 14 eq. with respect to the mAb); lanes 4-6 contain mixtures of CC49-TCO-7 and $^{177}$Lu-DOTA-tetrazine (10, 12, and 14 eq. with respect to the mAb).

A solution of CC49 (5 mg/mL, 250 μL) in PBS was modified with 1 or 10 molar eq. of TCO—NHS (6 or 7, 10 mg/mL solution in DMSO) in a total volume of 500 μL PBS. The pH was adjusted to 9 with 1 M sodium carbonate buffer. The reactions were carried out under agitation for 30 min at RT in the dark. Subsequently, the TCO-modified mAbs were extensively washed with PBS using Amicon Ultra-15 centrifugal devices. At the end of the conjugation procedure the purity and integrity of the CC49-TCO conjugates were assessed by SEC-HPLC and SDS-PAGE analysis (FIGS. 6 and 7). The conjugation yields were determined with tetrazine titrations. The TCO-modified mAbs (25 μL) were reacted with a known excess of carrier-added $^{177}$Lu-DOTA-tetrazine in PBS (50 μL). After 10 min incubation at 37° C., the reaction mix was added with non-reducing sample buffer, boiled for 10 min and analyzed by SDS-PAGE. After gel electrophoresis, the radioactivity distribution in each lane was assessed with phosphor imager. The reaction yields between $^{177}$Lu-DOTA-tetrazine and the CC49-TCO constructs was estimated from the intensity of the radioactive mAb band with respect to the total radioactivity in the lane (FIG. 8). When 1 eq. TCO—NHS 6 and 7 were used, the conjugation procedure afforded 0.4 and 0.7 TCO per mAb molecule, respectively. When 10 eq. TCO—NHS 6 and 7 were used, the conjugation procedure afforded 5.2 and 8.4 TCO per mAb molecule, respectively.

Example 3

Measurements of Reaction Kinetics Between Tetrazine and mAb-Conjugated endo- and exo-E-2,5-dioxopyrrolidin-1-yl bicyclo[6.1.0]non-4-ene carboxylate (6 and 7)

Figure 9:
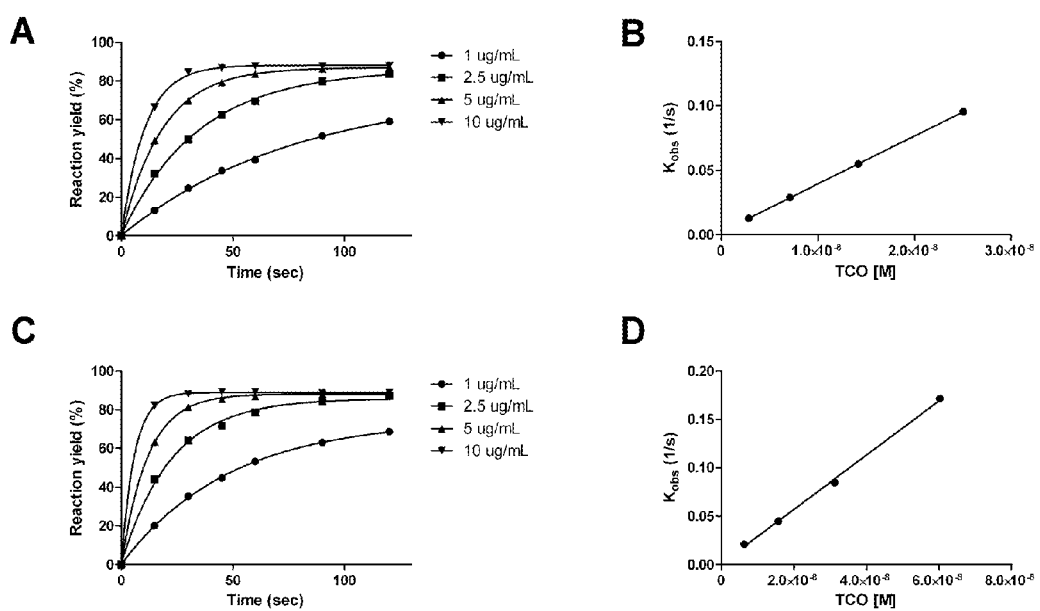
FIG. 9 depicts the results of the kinetics measurements described in Example 3. Time dependent reaction yields between $^{177}$Lu-DOTA-tetrazine 8 (0.67 nM) and (A) CC49-TCO-6 or (C) CC49-TCO-7 (4 different mAb concentrations) and plots of $K_{obs}$ vs. (B) TCO-6 or (D) TCO-7 concentration.

Tetrazine-DOTA 8 (FIG. 5) was radiolabeled with carrier-added $^{177}$Lu at a specific activity of 8 MBq/μg. $^{177}$Lu-DOTA-tetrazine (0.67 nM) was reacted with increasing concentrations of CC49 modified with 0.4 or 0.7 eq. of endo and exo TCO (6 and 7) in 1 mL PBS, pH 7.4, at 37° C. At selected times (15, 30, 45, 60, 90 and 120 sec) a 20 μL sample was withdrawn and the reaction was quenched with tetrazine derivative 9 (3 μL, 1 mg/mL in DMF). The samples were then added with non-reducing sample buffer, boiled for 10 min and analyzed by SDS-PAGE. After gel electrophoresis, the radioactivity distribution in each lane was assessed with phosphor imager. The reaction yields between $^{177}$Lu-DOTA-tetrazine and the CC49-TCO constructs were estimated from the intensity of the radioactive mAb band with respect to the total radioactivity in the lane. The time-dependent reaction yields were fitted to a pseudo-first order association curve and a rate constant ($K_{obs}$) was determined from the fit (FIGS. 9, A and C). Then the $K_{obs}$ values were plotted vs. the molar concentration of TCO and fitted using linear regression (FIGS. 9, B and D). Based on $K_{obs}$[CC49-TCO]($k_2$), the second order rate constant is the slope of the line, and was found to be 3.72±0.01×10$^6$ M$^{-1}$s$^{-1}$ and 2.80±0.08×10$^6$ M$^{-1}$s$^{-1}$ for the endo and exo TCO isomers, respectively.

All calculations were performed with GraphPad Prism version 5.01.

Example 4

In Vivo Stability of mAb Conjugated with endo- and exo-E-2,5-dioxopyrrolidin-1-yl bicyclo[6.1.0]non-4-ene-9-carboxylate (6 and 7)

The mAb CC49 functionalized with 5.2 and 8.4 mol eq. of 6 and 7, respectively, were radio labeled with $^{125}$I with the Bolton-Hunter procedure according to the manufacturer instruction. Briefly, ca. 5 MBq sodium [$^{125}$I]iodide was diluted with 50 μL PBS and added with 1 μL Bolton-Hunter reagent (SHPP, Pierce) solution in DMSO (0.1 μg/μL) and 25 μL chloramine-T (Sigma-Aldrich) solution in PBS (4 mg/mL). The solution was mixed for 10-20 sec, then 5 μL DMF and 100 μL toluene were added. After vortexing, the organic phase containing $^{125}$I-SHPP was transferred into a glass vial and dried at room temperature under a gentle stream of N$_2$. 300 μg CC49-TCO in PBS were then added to the $^{125}$I-SHPP coated glass vial and the pH was adjusted to 9 with 1M sodium carbonate buffer pH 9.6. The vial was incubated at room temperature under gentle agitation for ca. 60 min then the $^{125}$I-mAb labeling yield was evaluated with radio-ITLC (78-85%). The crude $^{125}$I-mAb was purified through Zeba Desalting spin columns (40 kDa MW cut-off, Pierce) pre-equilibrated with saline solution. The radiochemical purity of the $^{125}$I-labeled CC49-TCO was greater than 98%, as determined by radio-ITLC, radio-HPLC and SDS-PAGE analysis. The specific activity of the mAb was adjusted to 8-9 kBq/μg by adding unlabeled CC49-TCO.

Nude female Balb/C mice (20-25 g body weight, Charles River Laboratories, n=3) were injected 300 μg $^{125}$I-CC49-TCO constructs. At selected time points (1, 6, 24 and 48 h post injection) blood samples were withdrawn from the vena saphena and collected in vials containing heparin. At the end of the experiment, the mice were anesthetized and sacrificed by cervical dislocation. Stomachs and thyroids were removed, blotted dry and counted in a gamma-counter (Wizard 3, Perkin-Elmer) along with standards to determine the percent injected dose (% ID) per organ. The low $^{125}$I uptake in these organs (see table) confirmed that the radiolabeled mAb retains the label in vivo.

Figure 10:
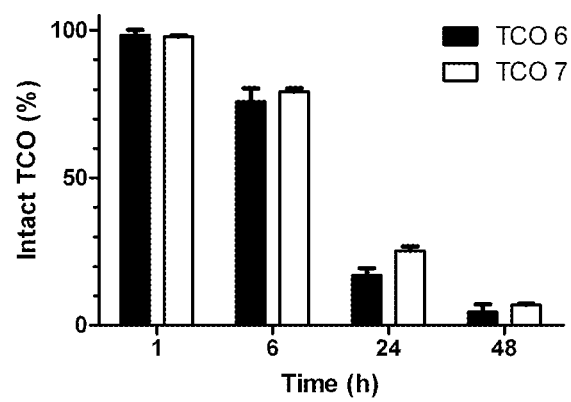
FIG. 10 depicts the in vivo stability of TCO 6 and 7 conjugated to CC49, as described in Example 4. Bars represent the mean and error bars represent one standard deviation (n=3).

Shortly after withdrawal, the blood samples were then added with an excess of carrier-added $^{177}$Lu-DOTA-tetrazine 8 (FIG. 5) radiolabeled at exactly a 0.1 MBq/μg specific activity. The mixtures were incubated for 10 min at 37° C. and then centrifuged for 5 min at 400×g to separate blood cells. This procedure was repeated twice then 20 μL supernatant was withdrawn and diluted with 30 μL PBS. The retro Diels-Alder reaction product was separated from the unreacted $^{177}$Lu-tetrazine with a Zeba desalting spin column (40 kDa MW cut-off, 30 μL sample loaded). The radioactivity contained in the eluates was measured in a gamma-counter with a dual-isotope protocol (10-80 keV window for $^{125}$I and 155-380 keV window for $^{177}$Lu). A serum sample containing $^{177}$Lu-tetrazine alone was used to correct for $^{177}$Lu "leakage" from the Zeba column. The $^{125}$I counts were corrected for radioactive decay then the $^{177}$Lu/$^{125}$I ratio was calculated. The decrease in the $^{177}$Lu/$^{125}$I ratio ex vivo was caused by the deactivation of the TCO groups in vivo. FIG. 10 shows the change of $^{177}$Lu/$^{125}$I ratio with time as % intact TCO 6 and 7 (normalized to 100% at t=0). Both TCOs are still ca. 75-80% intact at 6 hours post-injection and 17-25% intact at 24 hours post injection. Two days post injection the deactivation of TCO 6 and 7 was complete.

Uptake of $^{125}$I in the stomachs and thyroids of mice injected with radiolabeled CC49 functionalized with TCO 6 and 7. Data presented as % ID±SD

|  | TCO 6 | TCO 7 |
|---|---|---|
| thyroid | 0.67 ± 0.26 | 0.40 ± 0.13 |
| stomach | 0.26 ± 0.07 | 0.28 ± 0.05 |

Example 5

Synthesis of (E-major)-2,5-dioxopyrrolidin-1-yl 4-((cyclooct-4-enyloxy)methyl)benzoate (12)

Figure 11:
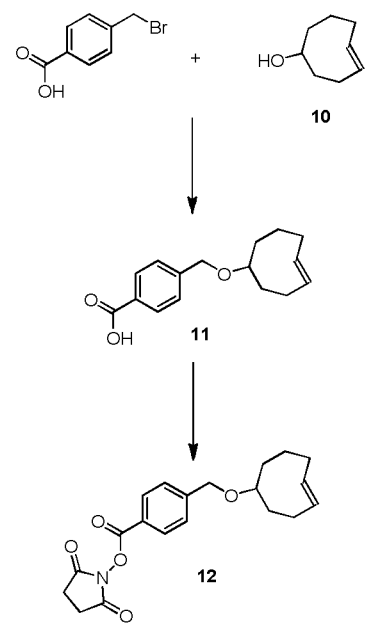
FIG. 11 depicts the synthesis of (E-major)-2,5-dioxopyrrolidin-1-yl 4-((cyclooct-4-enyloxy)methyl)benzoate 12, described in Example 5.

The synthesis of (E-major)-2,5-dioxopyrrolidin-1-yl 4-((cyclooct-4-enyloxy)methyl)benzoate (12) is depicted in FIG. 11. (E)-Cyclooct-4-enol (10, major isomer containing approximately 13% of the Z-isomer) was synthesized according to a literature procedure (M. Royzen, G. P. A. Yap, J. M. Fox, J Am Chem Soc 2008, 130, 3760). A 60% sodium hydride dispersion (1.8 g, 45 mmol) was added to an ice-bath-cooled solution of 10 (1.70 g, 13.5 mmol) in 60 mL DMF. After stirring for 4 h at room temperature, 4-bromomethylbenzoic acid (3.85 g, 17.9 mmol) was added in portions and the suspension was stirred overnight at room temperature. The mixture was poured into water (100 mL), tert-butyl methyl ether (100 mL) was added followed by 37% hydrochloric acid (5 mL). After separation, the aqueous layer was extracted with tert-butyl methyl ether (2×100 mL). The combined organic layers were washed with water (25 mL), dried over MgSO$_4$ and evaporated. The residue was passed through a thin silica layer with 4:1 hexane/ethyl acetate. The residue obtained after evaporation was dissolved in heptane (50 mL) at 70° C. and then cooled, affording 11. The product was dissolved in dichloromethane (40 mL), N-hydroxysuccinimide (0.57 g, 4.9 mmol) was added, the mixture was cooled in an ice-bath, followed by addition of N,N'-dicyclohexylcarbodiimide (1.03 g, 4.99 mmol). After 30 min the ice-bath was removed and the reaction mixture was stirred at room temperature for 18 h. After filtration and evaporation, the residue was purified by column chromatography on silica using a gradient of ethyl acetate in heptane (0-15%). Next, the residue was dissolved in tert-butyl methyl ether (20 mL) and poured into heptane (50 mL), yielding 12 (1.42 g, 29%) as a white solid. $^1$H NMR (300 MHz, CDCl$_3$): δ=8.10 (d, J=8.5 Hz, 2H), 7.45 (d, J=8.5 Hz, 2H), 5.60 (m, 1H), 5.34 (m, 1H), 4.54 (d, J=13.4 Hz, 1H), 4.47 (d, J=13.4 Hz, 1H), 3.09 (m, 1H), 2.91 (s, 4H), 2.43-1.40 (m, 10H); $^{13}$C NMR (75 MHz, CDCl$_3$): δ=169.0 (q), 161.5 (q), 146.7 (q), 135.1 (t), 132.1 (t), 130.4 (t), 127.0 (t), 123.7 (q), 85.3 (t), 68.0 (s), 40.5 (s), 37.7 (s), 34.2 (s), 32.7 (s), 31.4 (s), 25.4 (s); HRMS (ESI, m/z): Calculated for C$_{20}$H$_{23}$NO$_5$Na$^+$ ([M-Na]$^+$): 380.1474. Found: 380.1472.

Example 6

Synthesis of 2,5-dioxopyrrolidin-1-yl 41,45-dioxo-45-((6-(6-(pyridin-2-yl)-1,2,4,5-tetrazin-3-yl)pyridin-3-yl)amino)-4,7,10,13,16,19,22,25,28,31,34,37-dodecaoxa-40-azapentatetracontan-1-oate (16)

Figure 12:
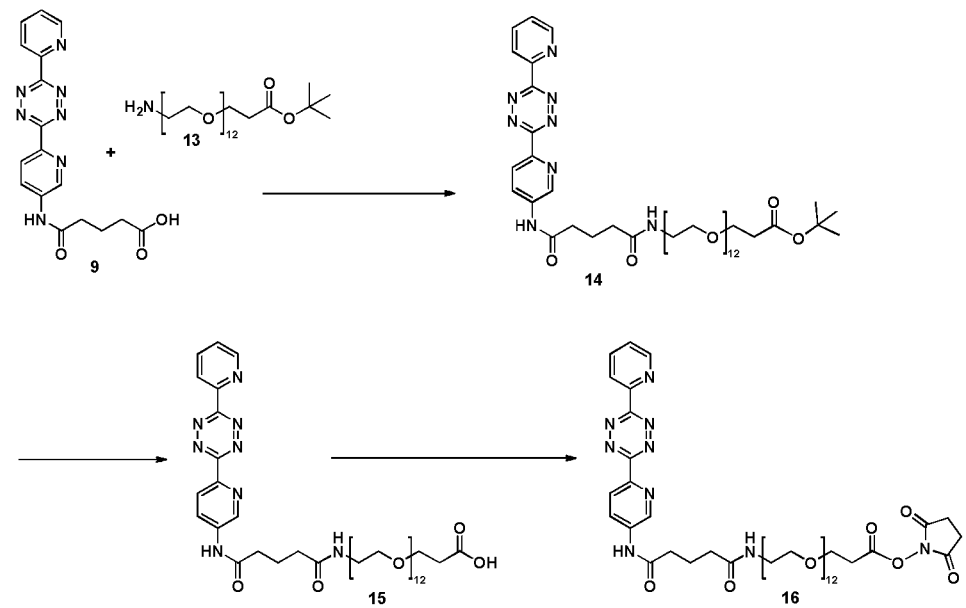
FIG. 12 depicts the synthesis of 2,5-dioxopyrrolidin-1-yl 41,45-dioxo-45-((6-(6-(pyridin-2-yl)-1,2,4,5-tetrazin-3-yl) pyridin-3-yl)amino)-4,7,10,13,16,19,22,25,28,31,34,37-dodecaoxa-40-azapentatetracontan-1-oate 16, described in Example 6.

The synthesis of 16 is outlined in FIG. 12, starting from 5-oxo-5-(6-(6-(pyridin-2-yl)-1,2,4,5-tetrazin-3-yl)pyridin-3-ylamino)pentanoic acid (9), which is made according to Rossin et al. Angewandte Chemie International Edition 2010, 49(19), 3375-8.

Tert-butyl 41,45-dioxo-45-((6-(6-(pyridin-2-yl)-1,2,4,5-tetrazin-3-yl)pyridin-3-yl)amino)-4,7,10,13,16,19,22,25,28,31,34,37-dodecaoxa-40-azapentatetracontan-1-oate (14)

Tert-butyl 1-amino-3,6,9,12,15,18,21,24,27,30,33,36-dodecaoxanonatriacontan-39-oate 13 (123 mg, 0.182 mmol; IRIS Biotech GmbH) was added into a dried reaction vial and co-evaporated twice with toluene. The vial was then put under nitrogen and extra dry DMF (2 ml) was added giving a colorless solution. 9 (100 mg, 0.274 mmol) and (benzotriazol-1-yloxy)tris(dimethylamino)phosphonium hexafluorophosphate (BOP; 267 mg, 0.603 mmol) dissolved in extra dry DMF (1 mL) were added sequentially to the reaction mixture under nitrogen atmosphere giving a red suspension. Finally, DIPEA (0.5 mL, 2.74 mmol) was added dropwise to the reaction mixture and the resulting solution was stirred overnight. The reaction mixture was evaporated to dryness, dissolved DCM (2 ml), and purified by flash column chromatography on silica gel using a gradient of 1-10% MeOH in DCM. The relevant fractions were combined and evaporated in vacuo yielding 14 (167 mg, 0.164 mmol, 90%) as a dark pink solid.

$^1$H NMR (300 MHz, CDCl$_3$): δ=10.58 (s, 1H), 9.05 (d, J=2.4 Hz, 1H), 8.93 (ddd, J$_1$=0.9 Hz, J$_2$=1.7 Hz, J$_3$=4.7 Hz, 1H), 8.62 (d, J=8.8 Hz, 1H), 8.59 (d, J=8.6 Hz, 1H), 8.43 (dd, J$_1$=2.4 Hz, J$_2$=8.8 Hz, 1H), 8.15 (td, J$_1$=1.8 Hz, J$_2$=7.8 Hz, 1H), 7.93 (t, J=5.5 Hz, 1H), 7.73 (ddd, J$_1$=1.1 Hz, J$_2$=4.7 Hz, J$_3$=7.8 Hz, 1H), 3.57 (t, J=6.2 Hz, 2H), 3.53-3.47 (broad s, 46H), 3.25-3.16 (m, 2H), 3.41 (t, J=6.2 Hz, 2H), 2.44 (t, J=7.3 Hz, 2H), 2.17 (t, J=7.3 Hz, 2H), 1.85 (q, J=7.3 Hz, 2H), 1.38 (s, 9H); $^{13}$C NMR (75 MHz, CDCl$_3$): δ=172.1 (q), 171.7 (q), 170.4 (q), 163.0 (q), 162.8 (q), 150.6 (t), 150.2 (q), 143.8 (q), 141.3 (t), 138.5 (q), 137.8 (t), 126.5 (t), 126.1 (t), 124.8 (t), 124.2 (t), 79.7 (q), 69.8 (s), 69.7 (s), 69.6 (s), 69.5 (s), 69.1 (s), 66.2 (s), 38.5 (s), 35.8 (s), 35.7 (s), 34.4 (s) 27.7 (p), 20.9 (s).

41,45-dioxo-45-((6-(6-(pyridin-2-yl)-1,2,4,5-tetrazin-3-yl)pyridin-3-yl)amino)-4,7,10,13,16,19,22,25,28,31,34,37-dodecaoxa-40-azapentatetracontan-1-oic acid (15)

To a stirred solution of 14 (160 mg, 0.157 mmol) in anhydrous DCM (2 mL) under nitrogen atmosphere was added TFA (2 mL). The reaction mixture was stirred for 2 hours at room temperature and evaporated to dryness. The residue was redissolved in dry DCM (2 ml) and again treated with TFA (2 mL) for 2 hours. This process was repeated once more. Finally, the reaction mixture was evaporated to dryness and co-evaporated twice with DCM furnishing the deprotected product 15 in quantitative yield.

$^1$H NMR (300 MHz, CDCl$_3$): δ=10.57 (s, 1H), 9.05 (broad s, 1H), 8.94 (broad s, 1H), 8.63 (d, J=8.4 Hz, 1H), 8.60 (d, J=7.2 Hz, 1H), 8.43 (dd, J$_1$=2.4 Hz, J$_2$=8.8 Hz, 1H), 8.16 (td, J$_1$=1.7 Hz, J$_2$=7.8 Hz, 1H), 7.93 (t, J=5.5 Hz, 1H), 7.74 (dd, J$_1$=4.7 Hz, J$_3$=6.8 Hz, 1H), 3.58 (t, J=6.4 Hz, 2H), 3.53-3.46 (broad s, 46H), 3.41 (t, J=6.0 Hz, 2H), 3.25-3.17 (m, 2H), 2.44 (t, J=7.3 Hz, 2H), 2.17 (t, J=7.3 Hz, 2H), 1.85 (q, J=7.3 Hz, 2H).

2,5-Dioxopyrrolidin-1-yl 41,45-dioxo-45-((6-(6-(pyridin-2-yl)-1,2,4,5-tetrazin-3-yl)pyridin-3-yl) amino)-4,7,10,13,16,19,22,25,28,31,34,37-dodecaoxa-40-azapentatetracontan-1-oate (16)

To a stirred solution of 15 (150 mg, 0.155 mmol) in anhydrous DCM (3 ml) under N$_2$-atmosphere at 0° C. were sequentially added di-(N-succinimidyl) carbonate (47.8 mg, 0.187 mmol), pyridine (15 μL), and triethylamine (0.25 mL). The mixture was stirred for 2 hours while warming up to room temperature, then evaporated to dryness, redissolved in DCM (20 ml), and washed with H$_2$O (3×10 mL). The organic layer was dried over MgSO$_4$, filtered and evaporated in vacuo yielding 16 (94 mg, 0.089 mmol, 57%) as a dark pink solid.

$^1$H NMR (300 MHz, CDCl$_3$): δ=9.67 (s, 1H), 9.01-8.97 (m, 2H), 8.77-8.71 (m, 2H), 8.64 (dd, J$_1$=2.4 Hz, J$_2$=8.8 Hz, 1H), 8.02 (td, J$_1$=1.7 Hz, J$_2$=7.7 Hz, 1H), 7.58 (ddd, J$_1$=1.1 Hz, J$_2$=4.7 Hz, J$_3$=7.5 Hz, 1H), 6.60 (t, J=5.4 Hz, 1H), 3.84 (t, J=6.4 Hz, 2H), 3.70-3.55 (broad s, 46H), 3.52-3.43 (m, 2H), 2.90 (t, J=6.5 Hz, 2H), 2.85 (s, 4H), 2.58 (t, J=6.8 Hz, 2H), 2.37 (t, J=6.8 Hz, 2H), 2.09 (q, J=6.8 Hz, 2H); $^{13}$C NMR (75 MHz, CDCl$_3$): δ=172.9 (q), 172.5 (q), 168.9 (q), 166.7 (q), 163.6 (q), 163.4 (q), 151.0 (t), 150.3 (q), 144.0 (q), 142.0 (t), 138.6 (q), 137.4 (t), 126.5 (t), 126.4 (t), 125.1 (t), 124.3 (t), 70.7 (s), 70.5 (s), 70.2 (s), 69.6 (s), 65.7 (s) 39.3 (s), 35.9 (s), 35.0 (s), 32.1 (s) 25.6 (s), 21.3 (s).

Example 7

Figure 13:
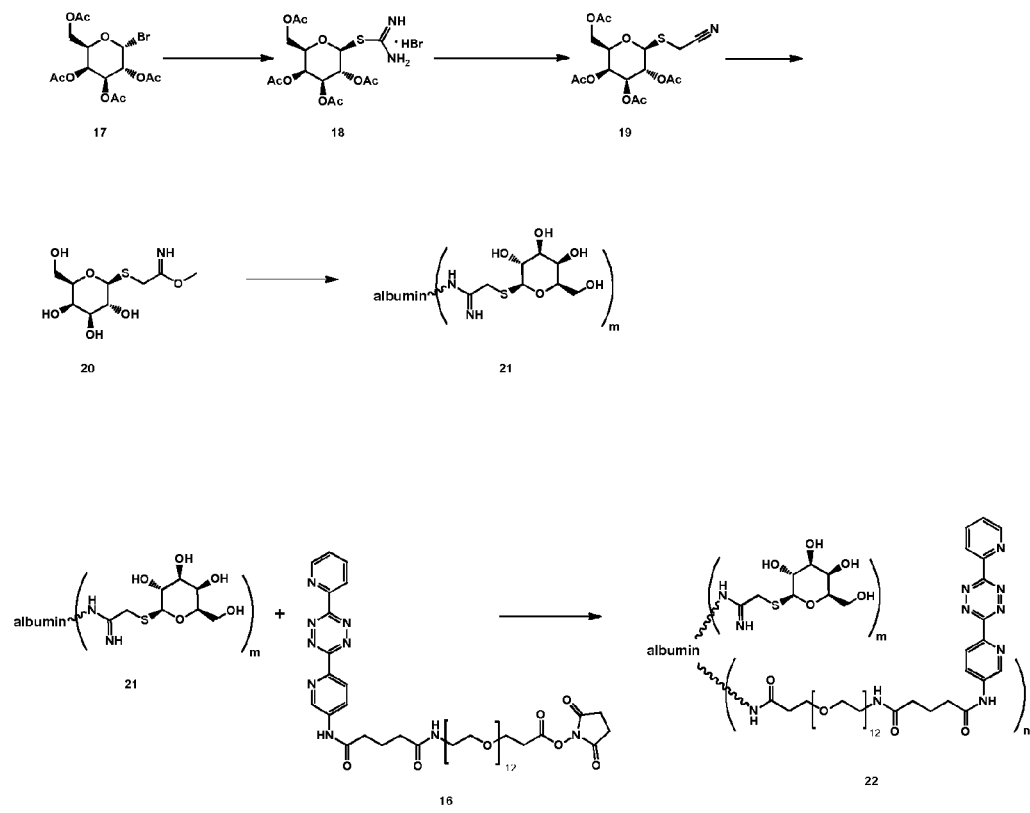
FIG. 13 depicts the synthesis of galactose-albumin-tetrazine 22, described in Example 7.

Synthesis of a Clearing Agent (Galactose-Albumin-Tetrazine) for TCO-Functionalized mAbs A clearing agent comprising a protein scaffold (mouse serum albumin, MSA) functionalized with galactose and tetrazine moieties was synthesized as outlined in FIG. 13. After intravenous injection, the tetrazine groups on the clearing agent react with circulating mAb-TCO via the retro Diels-Alder reaction while the galactose moieties interact with the Ashwell receptor on hepatocytes (ref L. J. Theodore, D. B. Axworthy, and J. M. Reno, patent US 2003/0129191) thus driving the mAb-clearing agent construct to the liver.

The clearing agent was prepared by 2-step sequential covalent modification of MSA, first with galactoses, then with tetrazines. Galactose modification was achieved using the amine-reactive 2-imino-2-methoxyethyl-1-thio-β-D-galactopyranoside (20), which conjugates to lysines on albumin.

Synthesis of Galactose-Albumin (21)

The galactose coupling agent 2-imino-2-methoxyethyl-1-thio-β-D-galactopyranoside (20) was prepared starting from 2,3,4,6-tetra-O-acetyl-α-D-galactopyranosyl bromide (17) in 3 steps via the intermediates 2-S-(2,3,4,6-tetra-O-acetyl-β-D-galactopyranosyl)-2-thiouronium bromide (18) and cyanomethyl 2,3,4,6-tetra-O-acetyl-1-thio-β-D-galactopyranoside (19) as shown in FIG. 13.

2-S-(2,3,4,6-tetra-O-acetyl-β-D-galactopyranosyl)-2-thiouronium bromide (18)

2,3,4,6-tetra-O-acetyl-α-D-galactopyranosyl bromide (17; 15.00 g, 36.48 mmol) and thiourea (3.05 g, 40.07 mmol) were dissolved in acetone (75 mL). The solution was heated to reflux for 2 hours, and subsequently filtered and cooled to 20° C. Addition of pentane (75 mL) resulted in the precipitation of the product as a white, crystalline solid (16.11 g, 91%). $^1$H-NMR (400 MHz, [D$_6$]DMSO): δ=1.95 (s, 3H, CH$_3$), 2.01 (s, 3H, CH$_3$), 2.08 (s, 3H, CH$_3$), 2.14 (s, 3H, CH$_3$), 4.09 (m, 2H, H$_6$, H$_{6'}$), 4.45 (t, J=6.4 Hz, 1H, H$_5$), 5.11 (t, J$_{2,3}$=10 Hz, 1H, H$_2$), 5.22 (dd, J$_{2,3}$=9.9 Hz, J$_{3,4}$=3.2 Hz, 1H, H$_3$), 5.39 (d, J=3.2 Hz, 1H, H$_4$), 5.71 (d, J$_{1,2}$=10 Hz, 1H, H$_1$), 9.11 (br, 2H, NH$_2$), 9.35 (br, 2H, NH$_2$).

Cyanomethyl 2,3,4,6-tetra-O-acetyl-1-thio-β-D-galactopyranoside (19)

2-S-(2,3,4,6-Tetra-O-acetyl-(3-D-galactopyranosyl)-2-thiouronium bromide (18; 16.11 g, 31.07 mmol), sodium metabisulphite (11.81 g, 62.14 mmol), potassium carbonate (4.72 g, 34.18 mmol), and chloroacetonitrile (8.21 g, 108.7 mmol) were dissolved in acetone/water (50:50 v/v, 200 mL), and stirred for 1 hour at room temperature. The reaction mixture was poured in ice-water (300 mL), and stirred for an additional 2 hours. The white precipitate was collected by filtration and recrystallized from hot methanol (30 mL). The product was filtered off as a white crystalline solid (9.61 g, 77%). M.p.=97° C. (Lit: 95-97° C.). $^1$H-NMR (400 MHz, CDCl$_3$): δ=2.00 (s, 3H, CH$_3$), 2.07 (s, 3H, CH$_3$), 2.09 (s, 3H, CH$_3$), 2.17 (s, 3H, CH$_3$), 3.35 (d, J=17 Hz, 1H, S—CH), 3.64 (d, J=17 Hz, 1H, S—CH'), 4.01 (t, J=6.9 Hz, 1H, H$_5$), 4.16 (m, 2H, H$_6$, H$_{6'}$), 4.7 (d, J$_{1,2}$=10 Hz, 1H, H$_1$), 5.11 (dd, J$_{3,4}$=3.2 Hz, J$_{2,3}$=10 Hz, 1H, H$_3$), 5.24 (t, J=10 Hz, 1H, H$_2$), 5.47 (d, J=2.4 Hz, 1H, H$_4$). FT-IR (ATR): v=2249 (CN, w), 1739 (C=O, s).

2-Imino-2-methoxyethyl-1-thio-β-D-galactopyranoside (20)

Cyanomethyl 2,3,4,6-tetra-O-acetyl-1-thio-β-D-galactopyranoside (19; 2.02 g, 5.00 mmol) was dissolved in anhydrous MeOH (50 mL) and a methanolic solution of sodium methoxide (25 w %, 115 μL, 0.50 mmol) was added. The reaction mixture was stirred at room temperature for 24 hours, and subsequently concentrated to a volume of 15 mL. The product was allowed to crystallize at room temperature and then at −18° C. Filtration and drying gave white crystals (1.11 g; 83%). M.p.=129° C. $^1$H-NMR (400 MHz, CD$_3$OD): δ=3.44 (dd, J$_{2,3}$=10 Hz, J$_{3,4}$=4.2 Hz, 1H, H$_3$), 3.52 (dd, J$_{2,3}$=10 Hz, J$_{1,2}$=9.0 Hz, 1H, H$_2$), 3.54 (m, 1H, H$_5$), 3.73 (—OCH$_3$), 3.78 (m, 2H, H$_6$, H$_{6'}$), 3.87 (dd, J$_{3,4}$=4.0 Hz, J$_{4,5}$=1.5 Hz, 1H, H$_4$), 4.27 (d, J$_{1,2}$=9.6 Hz, 1H, H$_1$). FT-IR (ATR): v=3287 (N—H, s), 1650 (C=NH, s).

Albumin-Coupling:

To a solution of MSA (20 mg, 0.303 μmol) dissolved in a 10:1 mixture of PBS pH 7.4/0.5M borate buffer pH 8.5 (900 μL) was added a freshly-prepared 18.2 mg/ml stock solution of 2-imino-2-methoxyethyl-1-thio-β-D-galactopyranoside (20) in the same buffer mixture (200 μL), resulting in a 45-fold molar excess of galactose coupling agent (20) relative to MSA. The reaction mixture was shaken (1000 rpm) at room temperature for 2 hours, then desalted using a Zeba desalting spin cartridge (7 kDa MWCO, Pierce), which was previously equilibrated with water. After lyophilization, galactose-albumin (compound 21) was obtained as a white fluffy solid (15.3 mg, 72%). The galactose modification grade was subsequently determined by MALDI-TOF analysis. MSA: $MH^+$=65941. Galactose-MSA: $MH^+$=69823, which corresponds to a mean of 16.4 galactoses/MSA (mass of added galactose fragment is 236 Da). Variation among different batches is about 16-18 galactoses/MSA). The stability of a 10 mg/ml solution of galactose-albumin in water at 4° C. was assessed by repeated MALDI-TOF analysis every 2 weeks for a total of 5 months. The conjugate proved to be stable.

Synthesis of Galactose-Albumin-Tetrazine (22):

A solution of galactose-functionalized mouse serum albumin (21, 1 mg) in PBS was mixed with a 10 mg/mL solution of tetrazine-NHS (16) in DMF (30 µL, 20 equiv. with respect to galactose-albumin) and 1M carbonate buffer pH 9.6 (7.5 µL) was added. The solution (250 µL total) was incubated at 37° C. for 30 min and then transferred into an Ultra-15 centrifugal filter unit (30 kDa MW cut-off). Product 22 was extensively washed with water then freeze-dried overnight to yield a pink fluffy powder. The tetrazine modification grade was determined by MALDI-TOF analysis. Galactose-albumin-tetrazine: $MH^+$=79010, which corresponds to a mean of 9.7 tetrazines/galactose(16.4)-MSA (mass of added tetrazine fragment is 948 Da; $MH^+$ (galactose(16.4)-MSA) =69823). UV-Vis measurements on nanodrop confirmed the presence of 9-10 tetrazines per molecule (measured value: 8.9 tetrazines/galactose(16.4)-MSA.

Example 8

Synthesis of (E)-2,5-dioxopyrrolidin-1-yl 2-(10-oxo-9-azabicyclo[6.2.0]dec-4-en-9-yl)acetate (26)

Figure 14:
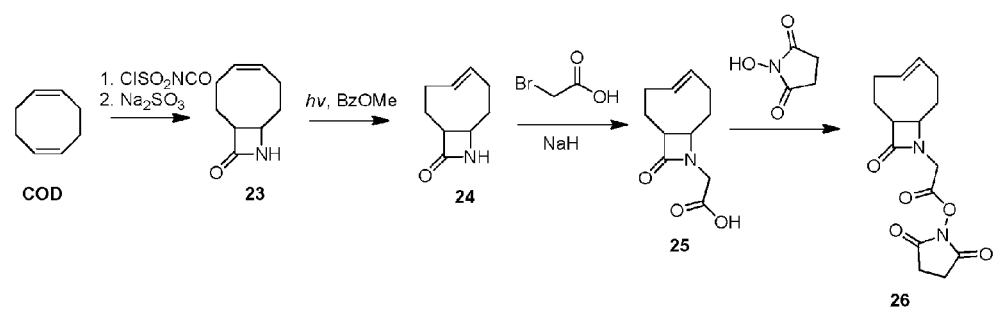
FIG. 14 depicts the synthesis of (E)-2,5-dioxopyrrolidin-1-yl 2-(10-oxo-9-azabicyclo[6.2.0]dec-4-en-9-yl)acetate (26), described in Example 8.

The synthesis of 26 is outlined in FIG. 14.

(Z)-9-azabicyclo[6.2.0]dec-4-en-10-one (23)

This compound was prepared via a literature method (Tanaka, M.; Oba, M.; Ichiki, T.; Suemune, H. Chem. Pharm. Bull. 2001, 49, 1178-1181). To a solution of cyclooctadiene (108 mL, 879 mmol) in toluene (200 mL) was added chlorosulfonyl isocyanate (18 g, 127 mmol, 14%). The solution was stirred at room temperature overnight. Analysis by NMR showed no conversion. The reaction was continued at 30° C. overnight and at 60° C. overnight. The mixture was diluted with diethyl ether (150 mL). A solution of sodium sulfate (50 g) in water (300 mL) was slowly added under vigorous stirring. The mixture was brought to pH 8 with 5% aqueous KOH and stirred overnight. The layers were separated and the aqueous layer was extracted with TBME (2×150 mL) and dichloromethane (2×150 mL). The combined organic layers were dried over sodium sulfate, filtered and evaporated in vacuo to give 7.79 g yellow oil. The crude product was purified by column chromatography (silica, dichloromethane/ethyl acetate 50% to methanol 5%) to give lactam 23 (2.68 g, 17.7 mmol, 2%) as a white solid.

(E)-9-azabicyclo[6.2.0]dec-4-en-10-one (24)

A solution of lactam 23 (2.68 g, 17.7 mmol) and methyl benzoate (2.41 g, 17.7 mmol, 1.0 eq) in diethyl ether (200 mL) was irradiated in a reactor for 6 d, while flowing the mixture over a silver nitrate/silica column (30.0 g, 0.59 mmol/g). The column was washed with TBME (400 mL) and TBME/methanol 9/1 (500 mL). The column was treated with ammonia and extracted with dichloromethane (3×150 mL). The combined dichloromethane layers were dried over sodium sulfate, filtered and evaporated in vacuo at 45° C. to give trans-cyclooctene 24 (two isomers, 1.72 g, 11.4 mmol, 64.3%) as a grey solid.

$^1$H-NMR (CDCl$_3$): δ 1.4-2.4 (m, 8H), 3.0-3.1 (m) and 3.1-3.2 (m) (1H), 3.55-3.6 (m) and 3.75-3.8 (m) (1H), 5.4-5.7 (m, 2H), 6.1-6.4 (bd, 1H). $^{13}$C-NMR: δ 27.2, 27.3, 28.5, 31.3, 32.9, 33.2, 34.9, 40.4, 54.1, 54.5, 56.2, 57.0, 134.2, 134.4, 134.8, 135.1, 171.1, 171.2.

(E)-2-(10-oxo-9-azabicyclo[6.2.0]dec-4-en-9-yl) acetic acid (25)

A suspension of sodium hydride (60% dispersion in oil, 330 mg, 8.27 mmol, 2.5 eq) in 17 mL dry THF was cooled in ice. A solution of lactam 24 (500 mg, 3.31 mmol, 1.0 eq) and bromoacetic acid (551 mg, 3.97 mmol, 1.2 eq) in dry THF (11 mL) was added to the suspension. The reaction mixture was stirred for 20 min. DMF (1.2 mL, dry) was added dropwise. The mixture was stirred at room temperature over the weekend. The mixture was concentrated in vacuo at 40° C. TBME (25 mL), ice and ice water (ca 25 mL) were added. The layers were separated and the aqueous layer was washed with TBME (15 mL). The combined TBME layers were extracted with water (15 mL). The combined aqueous layers were cooled in ice, acidified with citric acid (1.41 g) to pH 1-2 and extracted with TBME (3×25 mL). The combined organic layers were dried over sodium sulfate, filtered and evaporated in vacuo at 40° C. to give acid 25 (2 isomers, 360 mg, 1.72 mmol, 52.0%) as a white solid.

$^1$H-NMR (CDCl$_3$): δ 1.25-1.7 (m, 2H), 1.8-2.3 (m, 4H), 2.3-2.5 (m, 2H), 3.15-3.25 (m) and 3.25-3.35 (m) (1H), 3.65-3.95 (t+m, 2H), 4.1 (t, 1H), 5.6 (m, 3H). $^{13}$C-NMR: δ 27.0, 27.6, 28.5, 31.0, 31.5, 33.0, 33.2, 36.9, 41.4, 41.6 (all CH$_2$ signals), 54.4, 56.8, 58.4, 60.5 (all CH signals), 134.0, 134.5, 135.0, 135.2 (all CH signals), 171.4, 171.6, 171.7 (all C=O signals).

(E)-2,5-dioxopyrrolidin-1-yl 2-(10-oxo-9-azabicyclo [6.2.0]dec-4-en-9-yl)acetate (26)

A solution of acid 25 (0.21 g, 1.0 mmol), N-hydroxysuccinimide (0.14 g, 1.2 mmol, 2.25 eq) and EDCI (215 mg, 1.1 mmol, 1.1 eq) in dichloromethane (10 mL) was stirred at room temperature overnight in a flask, covered with aluminium foil. The solution was decanted and diluted with dichloromethane (10 mL). The solution was washed with water (2×5 mL) and brine (2×5 mL), dried over sodium sulfate, filtered and evaporated to give a brown oil (0.24 g). The oil was dissolved in dichloromethane (1 mL) and precipitated in pentane (20 mL). The residue was washed with pentane and dried in vacuo to give 26 (2 isomers, 0.16 g, 0.52 mmol, 52%) as an off-white solid.

$^1$H-NMR (CDCl$_3$): δ 1.25-1.7 (m, 2H), 1.8-2.3 (m, 4H), 2.35-2.5 (m, 2H), 2.85 (m, 4H), 3.15-3.25 (m) and 3.25-3.35 (m) (1H), 3.75-3.85 (m) and 3.85-3.95 (m) (1H), 4.0-4.1 (dd, 1H), 4.4-4.6 (dd, 1H), 5.45-5.65 (m, 2H). $^{13}$C-NMR: δ 26.0, 27.0, 27.5, 28.5, 31.0, 31.5, 33.0, 33.5, 37.0, 39.5, 39.5, 55.0, 57.5, 58.5, 60.5, 134.0, 134.5, 135.0, 135.5, 164, 169.5, 170, 170.5.

Example 9

Synthesis of (E)-1,2,3,4,4a,5,6,9,10,10a-decahydro-1,4-methanobenzo[8]annulen-11-ol (32)

Figure 15:
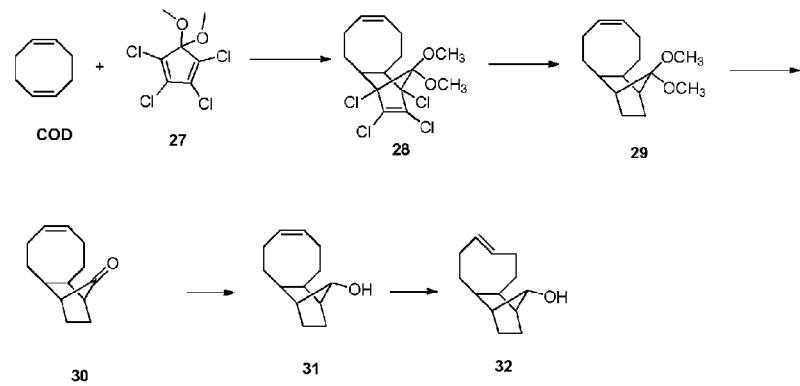
FIG. 15 depicts the synthesis of (E)-1,2,3,4,4a,5,6,9,10, 10a-decahydro-1,4-methanobenzo[8]annulen-11-ol (32), described in Example 9.

The synthesis of 32 is outlined in FIG. 15.

(4a,10a,Z)-1,2,3,4-tetrachloro-11,11-dimethoxy-1,4,4a,5,6,9,10,10a-octahydro-1,4-methanobenzo[8]annulene (28)

(see Tetrahedron 1981, 37, 4479-4494). A mixture of 5,5-dimethoxy-,1,2,3,4-tetrachlorocyclopentadiene 27 (6.7 mL, 10 g, 37.9 mmol) and 1,5 cyclooctadiene (37.3 mL, 32.8 g, 303 mmol, 8.0 eq) was heated to reflux temperature for 10 h. After cooling down to 50° C. a white precipitate was formed. The mixture was concentrated in vacuo. The solid was filtered off and washed with pentane. The combined filtrates were concentrated in vacuo and codistilled with toluene (2×) to give adduct 28 (11.4 g, 30.6 mmol, 80.7%) as a yellow, viscous oil.

$^1$H-NMR (CDCl$_3$): δ 1.35-1.5 (m, 2H), 1.95-2.1 (m, 4H), 2.3-2.45 (m, 2H), 2.65-2.75 (m, 2H), 3.55 (s, 3H), 3.6 (s, 3H), 5.7-5.8 (m, 2H).

(4a,10a,Z)-11,11-dimethoxy-1,2,3,4,4a,5,6,9,10,10a-decahydro-1,4-methanobenzo[8]annulene (29)

A mixture of lithium (4.16 g, 0.60 mmol, 28.7 eq) in dry tetrahydrofuran (130 mL) was stirred at reflux temperature under a nitrogen atmosphere. A solution of adduct 28 (7.78 g, 20.9 mmol, 1.0 eq) and tert-butanol (22 mL, 17 g, 0.23 mol, 11 eq) in tetrahydrofuran (13 mL) was added dropwise. Gas evolved during the addition and the reaction mixture turned to black. The mixture was stirred at reflux temperature over the weekend. The solids were filtered off over Celite and washed with tetrahydrofuran. The combined filtrates were concentrated to give a brown solid. The solid was mixed with ice (25 mL) and extracted with TBME (4×100 mL). The combined organic layers were dried over sodium sulfate, filtered and evaporated in vacuo to give crude 29 (4.23 g) as a brown oil. Purification by ISCO gave compound 29 (1.21 g, 5.12 mmol, 24.5%) as a slightly yellowish oil.

$^1$H-NMR (CDCl$_3$): δ 1.5 (s) and 1.5-1.65 (m) (6H), 1.7-1.9 (m, 4H), 1.95-2.1 (m, 2H), 2.25-2.4 (m, 4H), 3.25 (s, 3H), 3.3 (s, 3H), 5.8 (m, 2H). $^{13}$C-NMR: δ 16 (CH$_2$), (CH$_2$), 28 (CH$_2$), 37 (CH), 46 (CH), 130 (CH).

(4a,10a,Z)-1,2,3,4,4a,5,6,9,10,10a-decahydro-1,4-methanobenzo[8]annulen-11-one (30)

A solution of compound 29 (1.21 g, 5.12 mmol) in diethyl ether (3 mL) was mixed with aqueous sulfuric acid (2 M, 12 mL). The mixture was stirred vigorously for 5 days and extracted with diethyl ether (2×20 mL). The combined organic layers were dried over sodium sulfate, filtered and evaporated in vacuo to give ketone 30 (731 mg, 3.84 mmol, 75.0%) as a yellowish oil.

$^1$H-NMR (CDCl$_3$): δ 1.6-1.75 (m, 4H), 1.75-1.9 (m, 4H), 1.95-2.1 (m, 4H), 2.25-2.45 (m, 4H), 5.75 (m, 2H). $^{13}$C-NMR: δ 16 (CH$_2$), 25 (CH$_2$), 28 (CH$_2$), 37 (CH), 46 (CH), 130 (CH).

(4a,10a,Z)-1,2,3,4,4a,5,6,9,10,10a-decahydro-1,4-methanobenzo[8]annulen-11-ol (31)

To a solution of ketone 30 (598 mg, 3.14 mmol) in dry diethyl ether (18 mL) was added lithium aluminium hydride. The mixture was stirred under a nitrogen atmosphere for 3 days and subsequently quenched by dropwise addition of water (5 mL). The layers were separated and the aqueous layer was extracted with diethyl ether (20 mL). The combined organic layers were dried over sodium sulfate, filtered and evaporated in vacuo to give alcohol 31 (499 mg, 2.59 mmol, 82.6%, 15-85 mixture of isomers) as a colorless oil.

$^1$H-NMR (CDCl$_3$): δ 1.3-2.2 (m, 16H), 4.05 (bs, 1H), 5.75 (m, 2H). $^{13}$C-NMR: δ 20 (CH$_2$), 26 (CH$_2$), 28 (CH$_2$), 39 (CH), 48 (CH), 80 (CH), 132 (CH).

(4a,10a,E)-1,2,3,4,4a,5,6,9,10,10a-decahydro-1,4-methanobenzo[8]annulen-11-ol (32)

A solution of Z-alkene 31 (530 mg, 2.76 mmol) and methyl benzoate (0.347 mL, 375 mg, 2.76 mmol, 1.0 eq) in diethyl ether/heptanes 1/2 (600 mL) was irradiated for 36 h, while the solution was continuously led over a column filled with silica/silver nitrate 9/1 (5 g, ca 1 eq), silica (0.5 cm, and sand (0.5 cm). The column was placed in the dark during irradiation. The silica was washed with dichloromethane (40 mL) and the crude product was extracted from the column with dichloromethane/water/25% ammonia 2/1/1 (3×40 mL). The combined aqueous layers were extracted with dichloromethane (30 mL). The combined organic layers were dried over sodium sulfate, filtered and evaporated in vacuo to give 0.32 g yellow oil. The crude product was partially purified by column chromatography (50 mL Silica, ethyl acetate/heptanes 1/9) to give a mixture of product and aliphatic impurities (38 mg), max 0.198 mmol, 7.2%) as an off-white solid. The product is probably a mixture of 2 E-isomers.

$^1$H-NMR (CDCl$_3$): δ 0.8-2.4 (m, 16H), 4.0-4.15 (m, 2H), 5.4-5.85 (m, 2H). $^{13}$C-NMR: δ 20-60 (numerous CH and CH$_2$ signals), 80 (CH), 134 (CH). The 80 and 134 signals each have a minor peak next to it, the ratio of major vs. minor being ca. 3/1.

Example 10

Synthesis of (E)-3,3a,4,5,9,9a-hexahydro-1H-cycloocta[d]imidazol-2(8H)-one (40)

Figure 16:
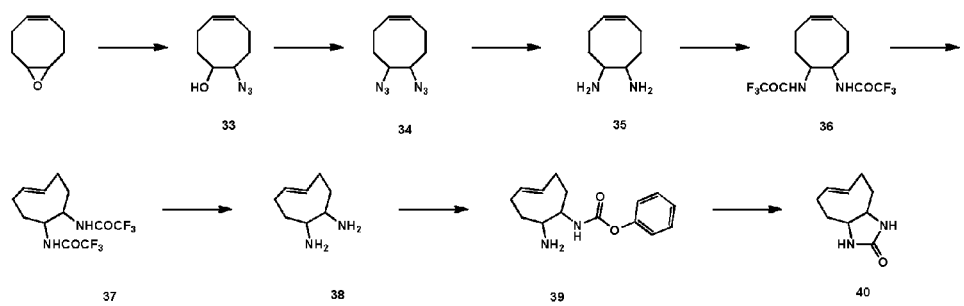
FIG. 16 depicts the synthesis (E)-3,3a,4,5,9,9a-hexahydro-1H-cycloocta[d]imidazol-2(8H)-one (40), described in Example 10.

The synthesis of 40 is outlined in FIG. 16.

Trans (Z)-8-azidocyclooct-4-enol (33)

Epoxycyclooctene was prepared by reaction of 1,5-cyclooctadiene with sodium perborate in acetic acid and dichloromethane, cf. Günes, Y.; Senocak, E.; Tosun, C.; Taskesenligil, Y., Org. Commun. 2009, 2:3, 79-83. The crude product was used as such. A solution of epoxycyclooctene (80.0 g, 0.645 mol) in 140 mL acetone was added over a 45 min period to a solution of sodium azide (80 g, 1.23 mol) in 200 mL water. The addition funnel was flushed with 20 mL acetone and the mixture was heated under reflux for 76 h. Most of the acetone was removed by rotary evaporation, 100 mL water was added to the residue and the mixture was extracted with 3×250 mL TBME. The organic layers were washed with 100 mL water, then dried and rotary evaporated to yield crude azidoalcohol 33 (mixed with the epoxide) which was used as such in the next step. $^1$H-NMR (CDCl$_3$, product signals): δ 1.6-2.6 (m, 8H), 3.65-3.8 (m, 2H), 5.5-5.65 (m, 2H).

Cis (Z)-5,6-diazidocyclooct-1-ene (34)

200 mL toluene was added to the residue and about 150 mL of solvent was removed by rotary evaporation. 300 mL toluene was added to the remainder (a ca. 1/1 mixture of the azido alcohol 33 and the starting epoxide) and the solution was cooled in ice. Triethylamine (86.1 g, 0.852 mol) was added, followed by the addition of methanesulfonyl chloride (93.8 g, 0.819 mol) in 100 mL toluene over a 1 h period and with mechanical stirring. The suspension was stirred for 2 days, then 200 mL water was added. The layers were separated and the organic layer was washed with 2×50 mL water. The successive aqueous layers were extracted with 250 mL toluene. Drying and rotary evaporation yielded a residue which was a mixture of the azido mesylate and the starting epoxide.

$^1$H-NMR (CDCl$_3$, product signals): δ 1.95-2.6 (m, 8H), 3.95 (dt, 1H), 4.8 (dt, 1H), 5.5-5.65 (m, 2H).

Half of the residue was warmed for 44 h at 75° C. with 100 mL DMF and sodium azide (20 g, 0.307 mol), then for 3 h at 85° C. The mixture was poured into 200 mL water and then extracted with 3×200 mL TBME. The organic layers were washed with 3×50 mL water, then dried and rotary evaporated to yield a residue which was a mixture of the diazide 34, epoxycyclooctene and impurities.

$^1$H-NMR (CDCl$_3$, product signals): δ 1.8 (m, 2H), 1.95-2.1 (m, 4H), 2.5-2.65 (m, 2H), 3.8 (dt, 2H), 5.6-5.7 (m, 2H).

Cis (Z)—N,N'-(cyclooct-5-ene-1,2-diyl)bis(2,2,2-trifluoroacetamide) (36)

The crude diazide 34 obtained above was dissolved in 150 mL THF and added over a 90 min period to lithium aluminium hydride (12.0 g, 0.315 mol) in 200 mL THF, cooling being done with cold water. The reaction mixture was heated under reflux for 8 h, then it was cooled and slowly quenched with 6 mL water and 12 mL 30% sodium hydroxide solution. Filtration, washing with THF and rotary evaporation yielded a residue which was dissolved in 150 mL dichloromethane, then cooled in ice. Trifluoroacetic anhydride (69.0 g, 0.328 mol) was added over a 30 min period. The solution was stirred for 4 h, then rotary evaporated. The residue was chromatographed on a 250 g silicagel column, elution being performed with heptane containing increasing amounts of ethyl acetate. The first fractions were the trifluoroacetate of cyclooct-2-en-1-ol. The fractions with the desired (Z)—N,N'-(cyclooct-5-ene-1,2-diyl)bis(2,2,2-trifluoroacetamide) were combined and recrystallized from a mixture of TBME and heptane to give 18.85 g of the product 36 (56.74 mmol, 18% based on epoxycyclooctene).

$^1$H-NMR of diamine 35 (CDCl$_3$, product signals): δ 1.65 (m, 2H), 1.8 (m, 2H), 2.0 (m, 2H), 2.4 (m, 2H), 3.0 (dt, 2H), 5.6 (m, 2H).

$^1$H-NMR of bisamide 36 (CDCl$_3$): δ 1.65 (m, 2H), 2.0 (m, 2H), 2.2 (m, 2H), 2.35 (m, 2H), 4.15 (dt, 2H), 5.9 (m, 2H), 7.5 (m, 2H). $^{13}$C-NMR: δ 23 (CH$_2$), 32 (CH$_2$), 54 (CH), 110-122 (q, CF$_3$), 132 (CH), 157-159 (q, C=O). $^{19}$F-NMR: δ-76.

Cis (E)-N,N'-(cyclooct-5-ene-1,2-diyl)bis(2,2,2-trifluoroacetamide) (37)

The crude trifluoroacetamide 36 obtained after evaporation of the reaction product from 3.50 g (25.0 mmol) (Z)-cyclooct-5-ene-1,2-diamine and trifluoroacetic anhydride (12.3 g, 58.6 mmol) was mixed with 4.0 g methyl benzoate and ca. 500 mL heptane-ether (ca. 2/1). The mixture was irradiated for 42 h while the solution was continuously flushed through a 41 g silver nitrate impregnated silicagel column (containing ca. 4.1 g silver nitrate). The column was flushed with 150 mL TBME, then with 150 mL TBME containing some methanol. The fractions were washed with 100 mL 15% ammonia, dried and rotary evaporated. The first fraction yielded a ½ mixture of the Z and E alkene, the second fraction yielded a small amount of the E alkene. The column was stirred with TBME and ammonia, then filtered and the layers were separated. The solid was treated once more with the aqueous layer and TBME, then filtered and the layers were separated. The organic layers were dried and rotary evaporated to yield 3.07 g of the E alkene 37 (9.25 mmol, 37% based on the amine).

$^1$H-NMR (CDCl$_3$): δ 1.6-1.9 (m, 4H), 2.1-2.5 (m, 4H), 3.8 (m, 1H), 4.1 (t, 1H), 5.4-5.55 (m, 1H), 5.65-5.8 (m, 1H), 6.4 (bs, 1H), 7.9 (bs, 1H).

Cis (E)-cyclooct-5-ene-1,2-diamine (38)

The amide 37 obtained above was mixed with 40 mL methanol, 5.0 g sodium hydroxide and 10 mL water. The mixture was warmed for 90 min at near reflux, then it was rotary evaporated and the residue was diluted with 30 mL water. Extraction with 3×50 mL dichloromethane, drying and rotary evaporation yielded the desired diamine 38, containing a small amount of solvent (1.38 g, ca. 100%).

$^1$H-NMR (CDCl$_3$): δ 1.4-2.5 (m, 8H), 2.8 (bs, 1H), 2.9 (d, 1H), 5.4-5.6 (m, 2H).

Cis (E)-phenyl (8-aminocyclooct-4-en-1-yl)carbamate (39)

Diphenylcarbonate (500 mg, 2.33 mmol) was added to a solution of the diamine 38 (300 mg, 2.14 mmol) in 10 mL dichloromethane and the solution was stirred for 4 d at RT. The solution was chromatographed on 25 g silica, eluting with dichloromethane with increasing amounts of methanol. The product fractions were combined and stirred with 15 mL TBME for 2 h. 15 mL heptane was added and the mixture was filtered. The solid was stirred with 15 mL TBME, then filtered. The combined filtrates were rotary evaporated and the residue was stirred overnight with heptane to give a solid. Filtration yielded the desired product 39.

$^1$H-NMR (CDCl$_3$): δ 1.5 (bs, 4H), 1.8-2.35 (m, 6H), 3.1 (bs, 1H), 3.6 (t, 1H), 5.5 (bd, 1H), 5.6 (m, 2H), 7.05-7.4 (m, 5H). $^{13}$C-NMR: δ 28.4 (CH$_2$), 33.0 (CH$_2$), 36.7 (CH$_2$), 40.7 (CH$_2$), 57.7 (CH), 58.4 (CH), 121.8 (CH), 125.4 (CH), 129.5 (CH), 133.2 (CH), 133.3 (CH), 151.3 (C), 154.0 (C).

Cis (E)-3,3a,4,5,9,9a-hexahydro-1H-cycloocta[d]imidazol-2(8H)-one (40)

Carbamate 39 was dissolved in DMSO, and stirred at 40° C. in the dark for 24 h, after which intramolecular cyclization to ureum 40 was complete. The product was used as such. $^1$H NMR (DMSO-d6): δ 1.4-2.3 (m, 8H), 3.38 (m, 1H), 3.62 (m, 1H), 5.51 (m, 2H), 6.07 (s, 1H), 6.12 (s, 1H). LCMS: m/z=167.1 (M+H$^+$).

Example 11

Synthesis of 2,2',2''-(10-(2-oxo-2-(6-oxo-6-(6-(6-(pyridin-2-yl)-1,2,4,5-tetrazin-3-yl)pyridin-3-ylamino)hexylamino)ethyl)-1,4,7,10-tetraazacyclododecane-1,4,7-triyl)triacetic acid (47) and 2,2',2''-(10-(2-oxo-2-(11-oxo-11-(6-(6-(pyridin-2-yl)-1,2,4,5-tetrazin-3-yl)pyridin-3-ylamino)undecylamino)ethyl)-1,4,7,10-tetraazacyclododecane-1,4,7-triyl)triacetic acid (48)

Figure 17:
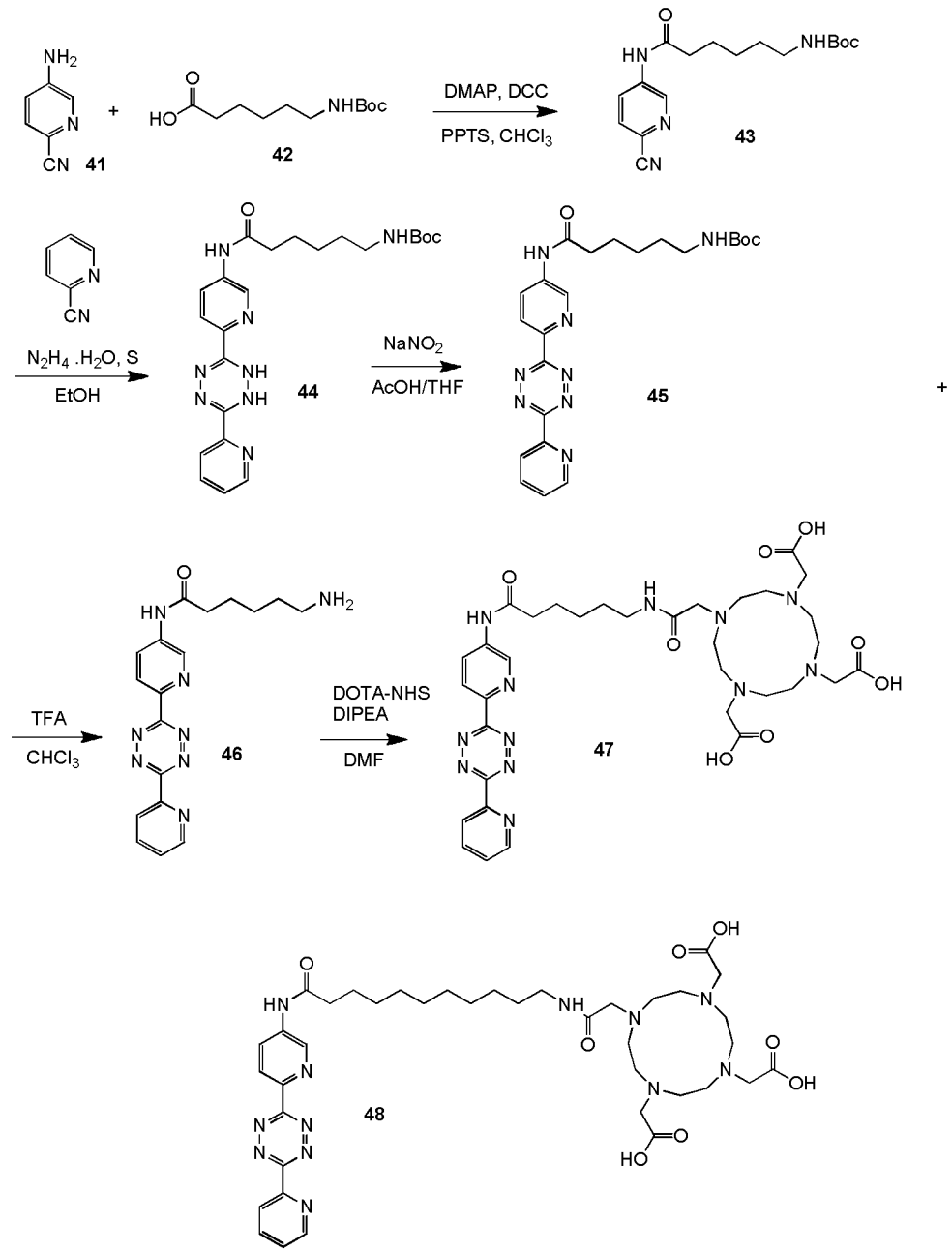
FIG. 17 depicts the synthesis of 2,2',2"-(10-(2-oxo-2-(6-oxo-6-(6-(6-(pyridin-2-yl)-1,2,4,5-tetrazin-3-yl)pyridin-3-ylamino)hexylamino)ethyl)-1,4,7,10-tetraazacyclododecane-1,4,7-triyl)triacetic acid (47) and 2,2',2"-(10-(2-oxo-2-

The synthesis of 47 and 48 is outlined in FIG. 17.

tert-butyl 6-(6-cyanopyridin-3-ylamino)-6-oxohexylcarbamate (43)

5-Amino-2-cyanopyridine 41 (1.02 g; 8.60 mmol), N-Boc-6-amino-hexanoic acid 42 (0.99 g; 4.30 mmol), DCC (1.77 g; 8.60 mmol), DMAP (1.05 g; 8.60 mmol), and PPTS (0.37 g; 1.47 mmol) were suspended in chloroform (15 mL). The mixture was stirred at room temperature for 18 hr, and then evaporated to dryness, and stirred in acetonitrile (20 mL). The precipitate was removed by filtration, and the filtrate was evaporated to dryness, dissolved in chloroform (20 mL), and washed with respectively aqueous citric acid (15 mL 0.5 M), aqueous potassium hydrogencarbonate (15 mL, 1 M), and water (15 mL). The organic phase was dried over sodium sulfate and evaporated to dryness. The crude product was purified by column chromatography (silica, hexane/ethylacetate=1:1) to yield the product 43 as a white solid (0.95 g; 61%). MS (ESI, m/z): Calcd for $C_{17}H_{25}N_4O_3^+$ ([M+H]$^+$): 333.19. Found: 333.17.

tert-butyl 6-oxo-6-(6-(6-(pyridin-2-yl)-1,2-dihydro-1,2,4,5-tetrazin-3-yl)pyridin-3-ylamino)hexylcarbamate (44)

Tert-butyl 6-(6-cyanopyridin-3-ylamino)-6-oxohexylcarbamate 43 (0.70 g; 2.1 mmol), 2-cyanopyridine (0.87 g; 8.4 mmol), hydrazine hydrate (1.25 g; 20 mmol) were dissolved in ethanol (2 mL), and sulfur (0.22 g; 7 mmol) was added. The mixture was stirred at 70° C. under an inert atmosphere of argon for 2 hr, and then at 50° C. for 16 hr. The orange suspension was diluted with chloroform (10 mL), and the resulting solution was washed with water (2 times 15 mL). The organic phase was dried over sodium sulfate and evaporated to dryness. The crude product was purified by column chromatography (silica, chloroform/acetone=4:1) to yield the product 44 as an orange solid (0.65 g; 66%). MS (ESI, m/z): Calcd for $C_{23}H_{31}N_8O_3^+$ ([M+H]$^+$): 467.25. Found: 467.33.

tert-butyl 6-oxo-6-(6-(6-(pyridin-2-yl)-1,2,4,5-tetrazin-3-yl)pyridin-3-ylamino) hexylcarbamate (45)

Tert-butyl 6-oxo-6-(6-(6-(pyridin-2-yl)-1,2-dihydro-1,2,4,5-tetrazin-3-yl)pyridin-3-ylamino)hexylcarbamate 44 (0.30 g; 0.64 mmol) was dissolved in THF (1.5 mL), and acetic acid (2 mL) was added. Sodium nitrite (0.25 g; 3.62 mmol) was dissolved in water (1 mL) and added dropwise. The red solution was poured in aqueous potassium hydrogencarbonate (50 mL; 1 M), and the product was extracted with chloroform (50 mL). The organic layer was washed with water (50 mL), and dried over sodium sulfate and evaporated to dryness, to yield the product 45 as a purple solid (0.25 g; 83%). MS (ESI, m/z): Calcd for $C_{23}H_{29}N_8O_3^+$ ([M+H]$^+$): 465.23. Found: 465.42.

6-amino-N-(6-(6-(pyridin-2-yl)-1,2,4,5-tetrazin-3-yl)pyridin-3-yl)hexanamide (46)

tert-butyl 6-oxo-6-(6-(6-(pyridin-2-yl)-1,2,4,5-tetrazin-3-yl)pyridin-3-ylamino) hexylcarbamate 45 (66 mg; 0.14 mmol) was dissolved in chloroform (6 mL), and TFA (6 mL) was added. The solution was stirred at room temperature for 2 hr, and subsequently evaporated to dryness, to yield the product 46 as its TFA salt (52 mg; 100%). MS (ESI, m/z): Calcd for $C_{18}H_{21}N_8O^+$ ([M+H]$^+$): 365.19. Found: 365.33.

2,2',2"-(10-(2-oxo-2-(6-oxo-6-(6-(6-(pyridin-2-yl)-1,2,4,5-tetrazin-3-yl)pyridin-3-ylamino)hexylamino)ethyl)-1,4,7,10-tetraazacyclododecane-1,4,7-triyl)triacetic acid (47)

6-Amino-N-(6-(6-(pyridin-2-yl)-1,2,4,5-tetrazin-3-yl)pyridin-3-yl)hexanamide 46 (52 mg; 0.14 mmol) was dissolved in DMF (2.5 mL), and DIPEA was added (320 mg; 2.0 mmol). N-hydroxysuccinimide activated DOTA (161 mg; 0.2 mmol) was added, and the mixture was stirred at room temperature for 5 hr. The solution was evaporated to dryness, and the crude product was dissolved in a mixture of acetonitrile and water, and purified by preparative RP-HPLC. After lyophilisation the pure product 47 was obtained as a pink fluffy solid (80 mg, 76% yield). $^1$H-NMR (30% acetonitrile-d$_3$ in D$_2$O): δ=8.90 (m, 2H, ArH), 8.68 (d, 1H, ArH), 8.60 (dd, 1H, ArH), 8.31 (m, 1H, ArH), 8.24 (t, 1H, ArH), 7.82 (t, 1H, ArH), 3.80 (br s, 6H, NCH$_2$COOH), 3.72 (br s, 2H, NCH$_2$CONH), 3.34-3.23 (br m, 18H, NCH$_2$CH$_2$N, CH$_2$NHCO), 2.49 (t, 2H, NHCOCH$_2$), 1.70 (m, 2H, NHCOCH$_2$CH$_2$), 1.59 (m, 2H, CH$_2$CH$_2$NHCO), 1.41 (m, 2H, CH$_2$CH$_2$CH$_2$NHCO) ppm. $^{13}$C-NMR (30% acetonitrile-d$_3$ in D$_2$O): δ=175.5, 171.5 (br), 162.6, 162.5, 150.1, 148.1, 142.9, 141.6, 139.6, 138.4, 128.0, 127.9, 125.4, 124.8, 55.4, 54.3 (br), 49.4 (br), 39.4, 36.5, 28.2, 25.9, 24.6 ppm. ESI-MS: m/z for $C_{34}H_{47}N_{12}O_8^+$ ([M+H]$^+$): 751.37; Obs. [M+H]$^+$ 751.58, [M+Na]$^+$ 773.50, [M+2H]$^{2+}$ 376.42, [M+3H]$^{3+}$ 251.33. FT-IR (ATR): υ=3263, 3094, 2941, 2862, 1667, 1637, 1582, 1540, 1460, 1431, 1395, 1324, 1296, 1272, 1251, 1226, 1198, 1128, 1087, 1060, 1020, 992, 977, 920, 860, 831, 798, 782, 742, 718, 679, 663 cm$^{-1}$.

2,2',2"-(10-(2-oxo-2-(11-oxo-11-(6-(6-(pyridin-2-yl)-1,2,4,5-tetrazin-3-yl)pyridin-3-ylamino)undecylamino)ethyl)-1,4,7,10-tetraazacyclododecane-1,4,7-triyl)triacetic acid (48)

A procedure was used comparable to the described synthesis of 2,2',2"-(10-(2-oxo-2-(6-oxo-6-(6-(6-(pyridin-2-yl)-1,2,4,5-tetrazin-3-yl)pyridin-3-ylamino) hexylamino)ethyl)-1,4,7,10-tetraazacyclododecane-1,4,7-triyl)triacetic acid (47).

After lyophilisation the pure product 48 was obtained as a pink fluffy solid (90 mg, 78% yield). $^1$H-NMR (DMSO-d$_6$): δ=10.65 (s, 1H, NH), 9.06 (d, 1H, ArH), 8.93 (d, 1H, ArH), 8.61 (t, 2H, ArH), 8.44 (dd, 1H, ArH), 8.16 (t, 2H, ArH, NH), 7.73 (dd, 1H, ArH), 3.51 (br s, 6H, NCH$_2$COOH), 3.28 (br s, 2H, NCH$_2$CONH), 3.06 (q, 2H, CH$_2$NHCO), 3.34-3.23 (br m, 16H, NCH$_2$CH$_2$N), 2.43 (t, 2H, NHCOCH$_2$), 1.64 (m, 2H, NHCOCH$_2$CH$_2$), 1.42 (m, 2H, CH$_2$CH$_2$NHCO), 1.38-1.22 (m, 12H, CH$_2$) ppm. $^{13}$C-NMR (DMSO-d$_6$): δ=173.0, 171.0 (br), 169.1 (br), 163.5, 163.2, 151.0, 150.6, 144.2, 141.7, 139.1, 138.2, 127.0, 126.5, 125.3, 124.6, 57.3 (br), 55.2 (br), 50.7, 39.0, 36.8, 29.5, 29.4, 29.3, 29.19, 29.17, 29.1, 26.9, 25.3 ppm. ESI-MS: m/z Calcd for $C_{39}H_{57}N_{12}O_8^+$ ([M+H]$^+$): 821.44; Obs. [M+Na]$^+$ 843.58, [M+H]$^+$ 821.58, [M+2H]$^{2+}$ 411.42, [M+3H]$^{3+}$ 274.67. FT-IR (ATR): υ=3261, 3067, 2925, 2851, 1633, 1583, 1541, 1458, 1433, 1394, 1324, 1298, 1270, 1249, 1228, 1200, 1165, 1128, 1088, 1059, 1016, 991, 920, 885, 860, 832, 798, 782, 764, 742, 719, 687, 661 cm$^{-1}$.

Example 12

Stability and Reactivity of Tetrazine Model Compounds
Hydrolytic Stability Tests of Tetrazines
10 μL of a solution of the specific tetrazine in DMSO (25 mM) was diluted with PBS buffer (3 mL) (or a mixture of PBS and acetonitrile in case the aqueous solubility was too low). This solution was filtered, and using UV spectroscopy, the decrease of the absorption band at 525 nm was monitored, and from this data the rate of hydrolysis and half-life time was determined.

Reactivity of Tetrazines Towards trans-cyclooct-4-ene-1-ol (Minor Isomer)

A competition experiment was performed to determine the reactivity ratio of a specific tetrazine and 3-(5-acetamido-2-pyridyl)-6-(2-pyridyl)-1,2,4,5-tetrazine (that was chosen as the reference tetrazine), in the inverse-electron demand Diels-Alder reaction with trans-cyclooct-4-ene-1-ol (minor isomer).

To acetonitrile (0.100 mL) was added 5 μL of a solution of the specific tetrazine in DMSO (25 mM) and 5 μL, of a solution of the reference tetrazine in DMSO (25 mM). This mixture was diluted with water (0.9 mL), and the absolute amounts of both tetrazines was determined by HPLC-MS/PDA analysis. Subsequently, a solution of trans-cyclooct-4-ene-1-ol (minor isomer) in DMSO (25 μL, 2.5 mM) was slowly added, and the mixture was stirred for 5 min. Again, the absolute amounts of both tetrazines was determined by HPLC-MS/PDA analysis, and conversions for both tetrazines was calculated. From these conversions, the reactivity ratio ($R=k_{2,TCO}/k_{2,Ref}$) of both tetrazines was calculated using the mathematical procedure from Ingold and Shaw (*J. Chem. Soc.*, 1927, 2918-2926). The table below demonstrates how the reactivity and stability profile of tetrazines can be tailored to certain specifications by the use of various substituents.

| tetrazine | stability in PBS at 20° C. $t_{1/2}$ (hours) | Reactivity ratio ($R = k_{2,TZ}/k_{2,Ref}$) |
|---|---|---|
| (2-pyridyl)-tetrazine-(2-pyridyl) | 44 | 1.17 |
| (2-pyridyl)-tetrazine-(2-pyridyl-5-NH2) | 340 | 0.4 |
| (2-pyridyl)-tetrazine-(2-pyridyl-5-NHAc) | 80 | 1 |
| (2-pyridyl)-tetrazine-(2-pyridyl-5-glutarimide) | 24 | 1.6 |
| (2-pyrimidyl)-tetrazine-(2-pyrimidyl) | 4.5 | 0.12 |
| (5-F-2-pyridyl)-tetrazine-(5-F-2-pyridyl) | 115 | 1.07 |
| (5-CF3-2-pyridyl)-tetrazine-(5-CF3-2-pyridyl) | 3.6* | 5.3* |
| (5-CF3-2-pyridyl)-tetrazine-(2-pyridyl-5-NHC(O)Pr) | 35* | 1.84* |
| (2-pyrimidyl)-tetrazine-(2-pyridyl-5-NHC(O)Pr) | 3.2 | 2.7 |

-continued
| tetrazine | stability in PBS at 20° C. $t_{1/2}$ (hours) | Reactivity ratio (R = $k_{2,TZ}/k_{2,Ref}$) |
|---|---|---|
| 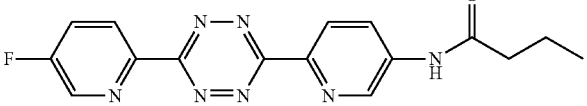 | 117 | 0.95 |
| 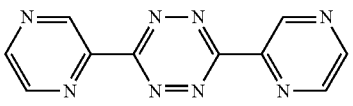 | 0.68 | 1.5 |
| 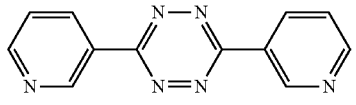 [SMILES: c1cncc(-c2nnc(-c3cccnc3)nn2)c1] | >150 | 0.19 |
| 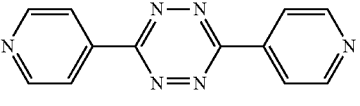 | 2.4 | 0.83 |
| 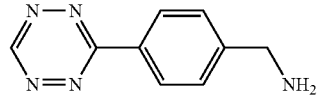 | 183 | 0.77 |
| 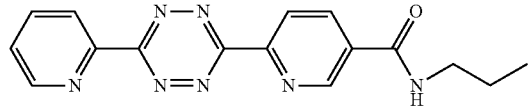 [SMILES: CCCNC(=O)c1ccc(-c2nnc(-c3ccccn3)nn2)nc1] | 4 | 1.76 |
| 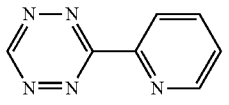 | 2.7 | 3.06 |
| 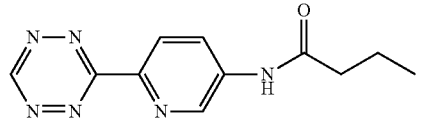 [SMILES: CCCC(=O)Nc1ccc(-c2nncnn2)nc1] | 10.3 | 2.8 |
| 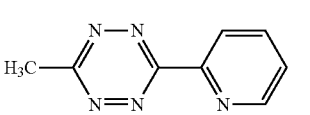 | 230 | 0.25 |
| 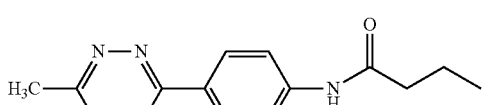 | 300 | 0.18 |
| 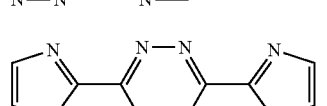 | n.d | 1.2 |
| 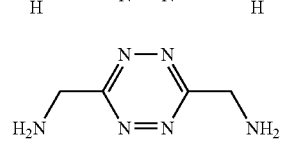 | 16 | n.d. |
*This value was determined in a 50/50 mixture of PBS and acetonitrile.

Example 13

Stability and Reactivity of TCO Model Compounds

Stability of Trans-Cyclooctene Derivatives

10 μL of a solution of the specific trans-cyclooctene derivative in dioxane (25 mM) was diluted with PBS buffer (3 mL), and this solution was stored at 20° C. in the dark. The faith of the TCO compound was monitored by HPLC-MS analysis, and an estimation of the half-life time was made.

Reactivity of Trans-Cyclooctene Derivatives Towards bis(2-pyridyl)-1,2,4,5-tetrazine A competition experiment was performed to determine the reactivity ratio of a specific trans-cyclooctene derivative and trans-cyclooct-4-ene-1-ol (minor isomer) (that was chosen as the reference trans-cyclooctene), in the inverse-electron demand Diels-Alder reaction with bis(2-pyridyl)-1,2,4,5-tetrazine.

To acetonitrile (0.05 mL) was added a solution of the specific trans-cyclooctene derivative in dioxane (5 μL 25 mM; $1.25 \times 10^{-7}$ mol) and a solution of the reference trans-cyclooctene in dioxane (5 μL 25 mM; $1.25 \times 10^{-7}$ mol). This mixture was diluted with water (0.45 mL). Subsequently, a solution of bis(2-pyridyl)-1,2,4,5-tetrazine ($6.25 \times 10^{-8}$ mol) in a mixture of acetonitrile (0.05 mL) and water (0.45 mL) was slowly added while stirring vigorously. After addition, the mixture was stirred for an additional 5 min. The conversion of both trans-cyclooctene derivatives was determined by HPLC-MS/PDA analysis, and from these conversions, the reactivity ratio ($R = k_{2,TCO}/k_{2,Ref}$) of the specific trans-cyclooctene derivative was calculated using the mathematical procedure from Ingold and Shaw (*J. Chem. Soc.*, 1927, 2918-2926). Below table demonstrates that the flattened TCO structures 4, 5, 25, and 40 exhibit an markedly increased reactivity towards tetrazines compared to the highly reactive minor isomer of trans-cyclooct-4-ene-1-ol.

| trans-cyclooctene derivative | stability in PBS at 20° C. $t_{1/2}$ (days) | Reactivity ratio (R = $k_{2,TCO}/k_{2,Ref}$) |
|---|---|---|
| endo isomer 4 | >3 days | 13.1 |
| exo isomer 5 | >3 days | 20.0 |
| 25 | ca. 1 day | 5.4 |
| 40 | >3 day | 7.3 |

Reaction of Trans-Cyclooctene β-Lactam Derivative with Various 1,2,4,5-tetrazines To demonstrate the wide applicability of the technology trans-cyclooctene β-lactam derivative 25 was reacted with a variety of 1,2,4,5-tetrazine derivatives.

Reaction with 3-(5-acetamido-2-pyridyl)-6-(2-pyridyl)-1,2,4,5-tetrazine

To a solution of 3-(5-acetamido-2-pyridyl)-6-(2-pyridyl)-1,2,4,5-tetrazine ($6.25 \times 10^{-8}$ mol) in water (1 mL) was added the trans-cyclooctene β-lactam derivative 25 ($6.25 \times 10^{-8}$ mol). An immediate discoloration of the tetrazine solution (from pink to colorless) indicated the quantitative reaction with the TCO. This was confirmed by HPLC-MS analysis: complete disappearance of the tetrazine signal and formation of the rDA adduct with m/z=475.33 (M+H$^+$).

Reaction with 3-(5-butyramido-2-pyridyl)-6-(2-pyrimidyl)-1,2,4,5-tetrazine

To a solution of 3-(5-butyramido-2-pyridyl)-6-(2-pyrimidyl)-1,2,4,5-tetrazine ($6.25 \times 10^{-8}$ mol) in water (1 mL) was added the trans-cyclooctene β-lactam derivative 25 ($6.25 \times 10^{-8}$ mol). An immediate discoloration of the tetrazine solution (from pink to colorless) indicated the quantitative reaction with the TCO. This was confirmed by HPLC-MS analysis: complete disappearance of the tetrazine signal and formation of the rDA adduct with m/z=504.42 (M+H$^+$).

Reaction with (4-(1,2,4,5-tetrazin-3-yl)phenyl)methanamine

To a solution of (4-(1,2,4,5-tetrazin-3-yl)phenyl)methanamine ($6.25 \times 10^{-8}$ mol) in water (1 mL) was added the trans-cyclooctene β-lactam derivative 25 ($6.25 \times 10^{-8}$ mol). An immediate discoloration of the tetrazine solution (from pink to colorless) indicated the quantitative reaction with the TCO. This was confirmed by HPLC-MS analysis: complete disappearance of the tetrazine signal and formation of the rDA adduct with m/z=369.17 (M+H$^+$).

Reaction with (3-methyl-6-(2-pyridyl)-1,2,4,5-tetrazine

To a solution of (3-methyl-6-(2-pyridyl)-1,2,4,5-tetrazine ($6.25 \times 10^{-8}$ mol) in water (1 mL) was added the trans-cyclooctene β-lactam derivative 25 ($6.25 \times 10^{-8}$ mol). An immediate discoloration of the tetrazine solution (from pink to colorless) indicated the quantitative reaction with the TCO. This was confirmed by HPLC-MS analysis: complete disappearance of the tetrazine signal and formation of the rDA adduct with m/z=355.33 (M+H$^+$).

Reaction with 3,6-diphenyl-1,2,4,5-tetrazine

To a suspension of 3,6-diphenyl-1,2,4,5-tetrazine ($6.25*10^{-8}$ mol) in water (1 mL) was added the trans-cyclooctene β-lactam derivative 25 ($6.25*10^{-8}$ mol). Within 15 min, the pink, turbid mixture became clear and colorless, indicating the quantitative reaction with the TCO. This was confirmed by HPLC-MS analysis: complete disappearance of the tetrazine signal and formation of the rDA adduct with m/z=416.42 (M+H$^+$).

Example 14

Antibody modification with (E-major)-2,5-dioxopyrrolidin-1-yl 4-((cyclooct-4-enyloxy)methyl)benzoate (12), and (E)-2,5-dioxopyrrolidin-1-yl 2-(10-oxo-9-azabicyclo[6.2.0]dec-4-en-9-yl)acetate (26)

As described in Example 2. When 1 eq. TCO—NHS 12 was used, the conjugation procedure afforded 0.5 TCO per mAb molecule. When 10 eq. TCO—NHS 12 were used, the conjugation procedure afforded 6.6 TCO per mAb molecule. Conjugation with 3 or 20 molar eq. of 26 afforded an average of 0.6 and 3.5 TCOs per CC49 molecule.

Example 15

Measurements of Reaction Kinetics Between Tetrazine and mAb-Conjugated (E-major)-2,5-dioxopyrrolidin-1-yl 4-((cyclooct-4-enyloxy)methyl)benzoate (12), and (E)-2,5-dioxopyrrolidin-1-yl 2-(10-oxo-9-azabicyclo[6.2.0]dec-4-en-9-yl)acetate (26)

As described in Example 3, TCOs 12 and was found to have a $k_2$ of 32000±2300 M$^{-1}$s$^{-1}$ (FIGS. 18a-18b) and TCO 26 was found to have a $k_2$ of 374800+/−3370 M$^{-1}$s$^{-1}$ (FIGS. 19a-19b).

Example 16

In Vivo Stability of mAb Conjugated with (E-major)-2,5-dioxopyrrolidin-1-yl 4-((cyclooct-4-enyloxy)methyl)benzoate (12)

The mAb CC49 functionalized with 6.6 mol eq. of 12 was radio labeled with $^{125}$I with the Bolton-Hunter procedure according to the manufacturer instruction. Briefly, ca. 5 MBq sodium [$^{125}$I]iodide was diluted with 50 μL PBS and added with 1 μL Bolton-Hunter reagent (SHPP, Pierce) solution in DMSO (0.1 μg/μL) and 25 μL chloramine-T (Sigma-Aldrich) solution in PBS (4 mg/mL). The solution was mixed for 10-20 sec, then 5 μL DMF and 100 μL toluene were added. After vortexing, the organic phase containing $^{125}$I-SHPP was transferred into a glass vial and dried at room temperature under a gentle stream of N$_2$. 200 μg CC49-TCO in PBS were then added to the $^{125}$I-SHPP coated glass vial and the pH was adjusted to 9 with 1M sodium carbonate buffer pH 9.6. The vial was incubated at room temperature under gentle agitation for ca. 60 min then the $^{125}$I-mAb labeling yield was evaluated with radio-ITLC (79%). The crude $^{125}$I-mAb was purified through Zeba Desalting spin columns (40 kDa MW cut-off, Pierce) pre-equilibrated with saline solution. The radiochemical purity of the $^{125}$I-labeled CC49-TCO was greater than 98%, as determined by radio-ITLC, radio-HPLC and SDS-PAGE analysis. The specific activity of the mAb was adjusted to 1.4 kBq/μg by adding unlabeled CC49-TCO.

Nude female Balb/C mice (20-25 g body weight, Charles River Laboratories, n=3) were injected 300 μg $^{125}$I-CC49-TCO. At selected time points up to 96 h post injection blood samples were withdrawn from the vena saphena and collected in vials containing heparin. At the end of the experiment, the mice were anesthetized and sacrificed by cervical dislocation. Stomachs and thyroids were removed, blotted dry and counted in a gamma-counter (Wizard 3, Perkin-Elmer) along with standards to determine the percent injected dose (% ID) per organ. The low $^{125}$I uptake in stomachs (0.19±0.04% ID) and thyroids (0.57±0.10% ID) confirmed that the radio labeled mAb retains the label in vivo.

Shortly after withdrawal, the blood samples were diluted to 100 μL with PBS then added with an excess of carrier-added $^{177}$Lu-DOTA-tetrazine 8 (FIG. 5) radio labeled at exactly a 0.1 MBq/μg specific activity. The mixtures were incubated for 20 min at 37° C. and then centrifuged for 5 min at 400×g to separate blood cells. 30 μL were purified by Zeba desalting spin column (40 kDa MW cut-off) to separate the retro Diels-Alder reaction product from the unreacted $^{177}$Lu-tetrazine. The radioactivity contained in the eluates was measured in a gamma-counter with a dual-isotope protocol (10-80 keV window for $^{125}$I and 155-380 keV window for $^{177}$Lu). A serum sample containing $^{177}$Lu-tetrazine alone was used to correct for $^{177}$Lu "leakage" from the Zeba column. The $^{125}$I counts were corrected for radioactive decay then the $^{177}$Lu/$^{125}$I ratio was calculated. The decrease in the $^{177}$Lu/$^{125}$I ratio ex vivo was caused by the deactivation of the TCO groups in vivo. FIG. 20 shows the change of $^{177}$Lu/$^{125}$I ratio with time as % intact TCO 12 (normalized to 100% at t=0). Linear regression of the data showed a 6.2 days half-life for TCO 12 in vivo.

Example 17

Tumor Pretargeting with CC49 Conjugated with exo-E-2,5-dioxopyrrolidin-1-yl bicyclo[6.1.0]non-4-ene-9-carboxylate (7) and (E-major)-2,5-dioxopyrrolidin-1-yl 4-((cyclooct-4-enyloxy)methyl)benzoate (12)

The CC49 construct carrying the exo-TCO 7 ($k_2$=2.8±0.1×10$^6$ M$^{-1}$s$^{-1}$) was chosen for in vivo evaluation due to the slightly higher stability in vivo with respect to the endo isomer 6. Therefore the tumor targeting capability and in vivo reactivity of this compound were evaluated side-by-side with those of the more stable but less reactive CC49-TCO 12.

The human colon cancer cell line LS174T was obtained from the ATCC and maintained in Eagle's minimal essential medium (Sigma) supplemented with 10% heat inactivated fetal calf serum (Gibco), penicillin (100 U/mL), streptomycin (100 μg/mL) and 2 mm Glutamax. Nude female Balb/C mice (20-25 g body weight, Charles River Laboratories) were inoculated subcutaneously with 5×10$^6$ cells in 100 μL sterile PBS. When the tumors reached approximately 100 mm$^3$ size, the mice were injected $^{125}$I-CC49 functionalized with either TCO 7 (8.4 per mAb) or TCO 12 (6.6 per mAb). Twenty-four hours post-mAb injection the mice received one dose of clearing agent (22, 160 μg/100 μL per mouse) followed 2 h later by $^{177}$Lu-DOTA-tetrazine 8 (1 eq. with respect to the mAb, ca. 0.5 MBq). Three hours post-tetrazine injection the mice were anesthetized and sacrificed by cervical dislocation, blood was withdrawn by heart puncture, organs and tissues of interest were harvested and blotted dry. All collected samples were weighed and added with 1 mL PBS. The sample radioactivity was measured in a gamma-counter (with a dual-isotope protocol) along with standards to determine the percent injected dose per gram tissue (% ID/g). FIG. 21 shows the biodistribution of the two $^{125}$I-labeled CC49-TCO constructs and FIG. 22 shows the biodistribution of $^{177}$Lu-tetrazine in the tumor-bearing mice pre-treated with the two CC49-TCO constructs.

CC49 functionalized with TCO 7 was retained in blood significantly longer than that of the corresponding construct carrying TCO 12 and, as a result, the tumor uptake was also significantly higher (34.85+/−5.86 vs. 18.71+/−; P<0.05). Despite higher tumor uptake of $^{125}$I-CC49 conjugated with TCO 7 compared to $^{125}$I-CC49-TCO(12), the $^{177}$Lu-tetrazine tumor uptake in the two groups of mice was similar. This was due to the lower stability of TCO 7 with respect to TCO 12. In fact, considering 18.7% residual intact TCO 7 and 90.2% residual TCO 12 at the time of tetrazine injection, the local concentration of TCO 7 on the tumor was lower than that of TCO 12 (see table). Despite this, however, the reaction yield (based on amount intact TCO) on the tumor of the mice pre-treated with CC49-TCO(7) was higher than that in the mice pre-treated with CC49-TCO(12). Therefore, these finding suggest that the higher reactivity in vitro translates in a higher reactivity in vivo for TCO 7 with respect to TCO 12, and that highly reactive TCO moieties such as 7 can be successfully used in pretargeting applications with a short to medium interval between antibody and probe administration. For long pretargeting intervals, a derivative of for example TCO 40 may be suitable.

TCO concentration and retro Diels-Alder reaction yields in blood and tumor of mice pre-treated with CC49-TCO(7) and CC49-TCO(12)

|  | [TCO] (×10⁻¹⁰ moles/g) | | Reaction yield in vivo (%) | |
| --- | --- | --- | --- | --- |
|  | tumor | blood | tumor | blood |
| TCO 7 | 3.6 ± 0.6 | 0.39 ± 0.04 | 12.3 ± 1.6 | 2.7 ± 1.0 |
| TCO 12 | 7.4 ± 2.7 | 0.41 ± 0.28 | 5.6 ± 1.3 | 5.8 ± 1.0 |

Example 18

Molecular Modelling of Partial Flattening of the TCO Ring as a Result of the Presence of Two Exocyclic Bonds Fixed in the Same Plane Below example demonstrates that the partial flattening of the TCO ring is the intrinsic result of the presence of two exocyclic bonds fixed in the same plane, and refers at any rate to the part opposite the endocyclic double bond, i.e. carbon atoms 5 and 6. This holds irrespective of where the two exocyclic bonds are positioned.

Molecules were drawn with ChemBioOffice version 12.02 followed by energy minimization using MM2. The structure was further optimized using CS MOPAC PRO version 8.03. The root mean square (RMS) Deviation (in Angstrom) from the least squares plane fitted to the selected atoms was computed in ChemBioOffice version 12.02. This plane is positioned such that the mean distance of the four atoms 4, 5, 6 and 7 to this plane is minimized.

Reference is made to FIG. 23. This figure shows the basic compound of which the plane of the E olefinic moiety is aligned with the Z-X plane. The 8 membered ring is approximately aligned with the X-Y plane. In order to increase reactivity of the olefinic bond, flattening of the system in the X-Y plane can be done. Introduction of strongly donating/accepting/conjugating groups on the carbon atoms next to the olefinic group is not preferred because in those cases electronic effects play a major role, however, other flattening elements (eg fused cyclobutyl) may be used on those positions. The position of two exocyclic bonds fixed in the same plane may be from C3 to C8 and will introduce flattening in the part of the molecule formed from the tetramethylene chain ($C^4$, $C^5$, $C^6$, and $C^7$), resulting in increased reactivity of the TCO. Such a flattening can be measured as a decrease of the RMS Deviation from the least squares plane A fitted to the four tetramethylene carbon atoms ($C^4$, $C^5$, $C^6$, and $C^7$). From the table it is apparent that substitutions by various rings and amide bonds onto the cyclooctene ring decrease the value of 0.430 Å of the unsubstituted basic compound (first entry in the table) in all cases.

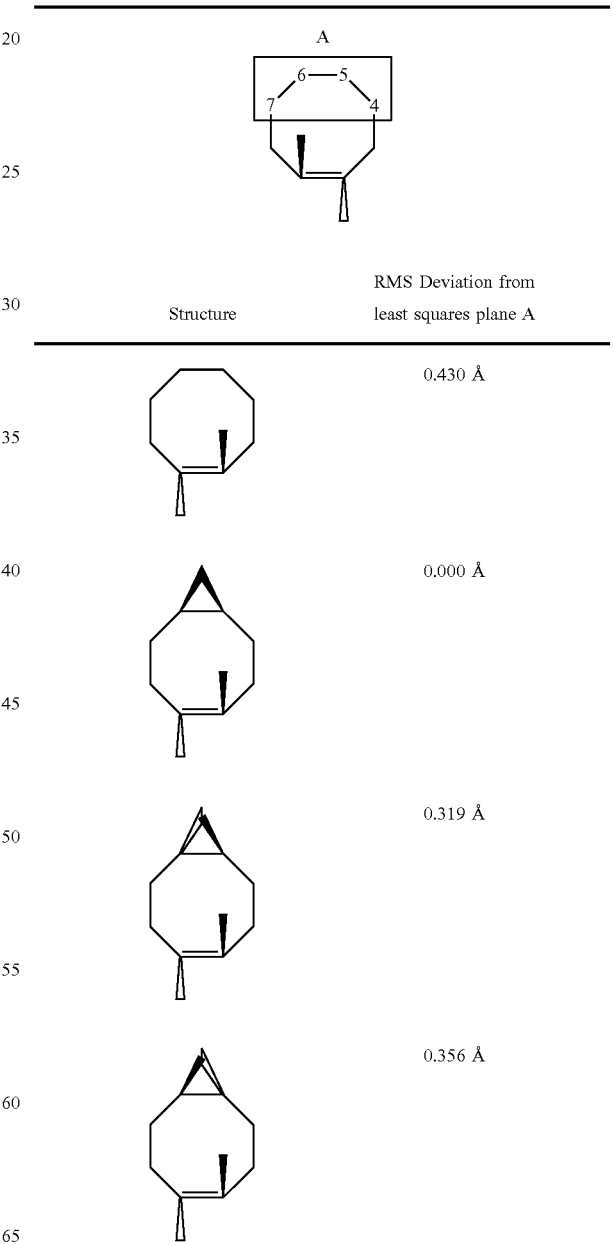

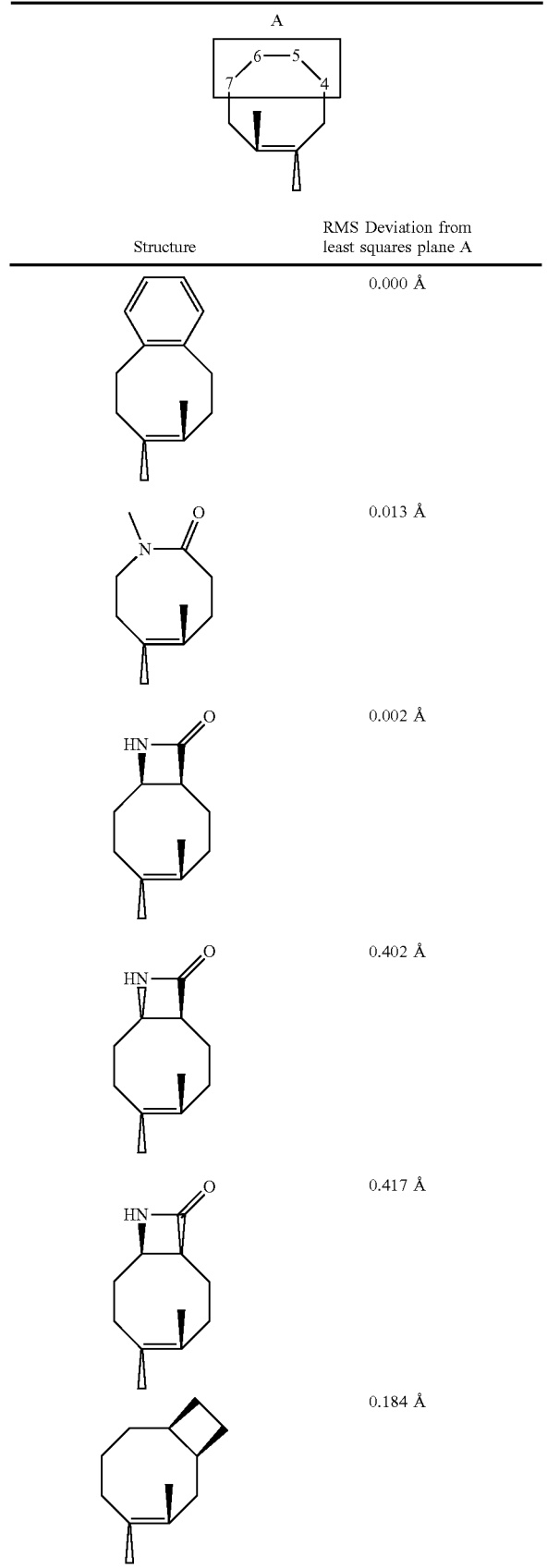
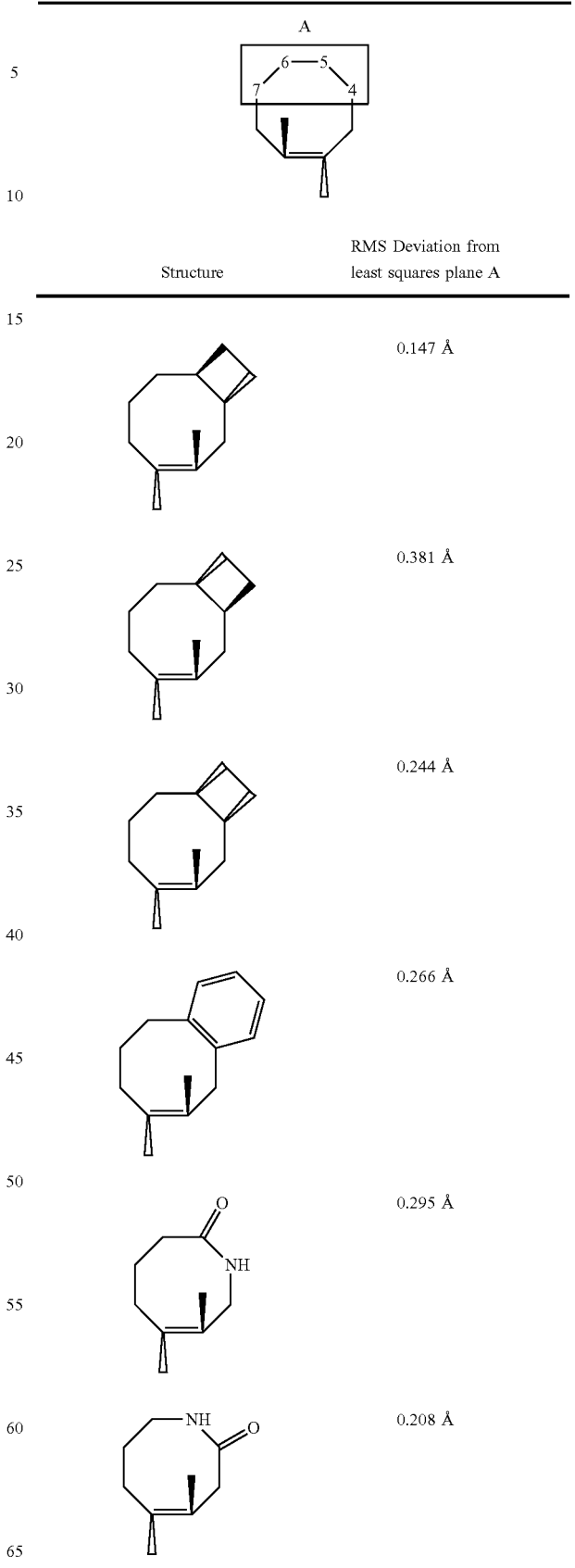

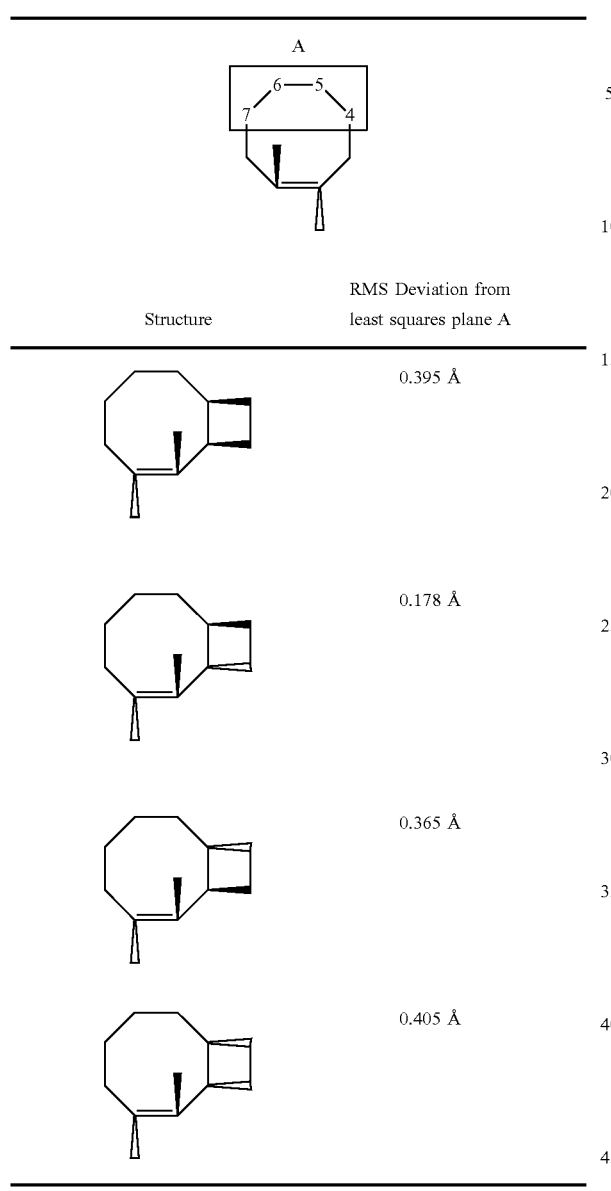

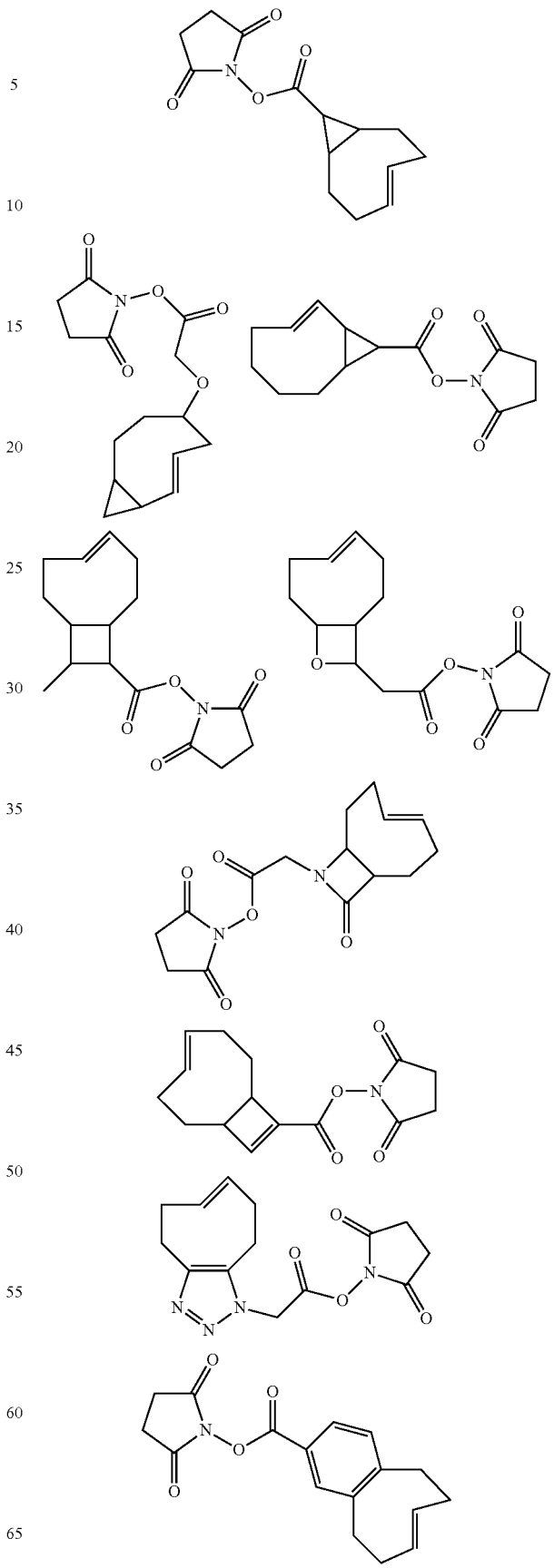

The invention claimed is:

1. A kit for targeted medical imaging and/or therapeutics, comprising at least one pre-targeting probe and at least one effector probe, wherein the pre-targeting probe comprises a primary targeting moiety and a first bio-orthogonal reactive group, and wherein the effector probe comprises an effector moiety, such as a label or a pharmaceutically active compound, and a second bio-orthogonal reactive group, wherein either of the first and second bio-orthogonal reactive groups is a dienophile and the other of the first and second bio-orthogonal reactive groups is a diene, wherein the dienophile is a trans-cyclooctene moiety comprising at least two exocyclic bonds fixed in the same plane, and comprising at least one linkage, either directly or by way of a spacer, to the pre-targeting probe or the effector probe, wherein the dienophile is a compound selected from the following structures, said structures showing N-hydroxy succinimide ester groups:

-continued

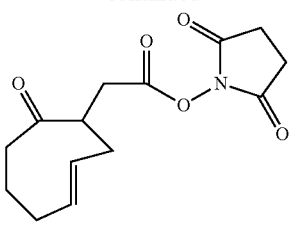

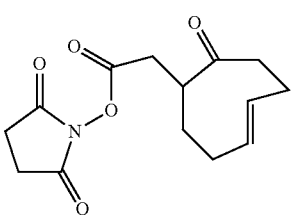

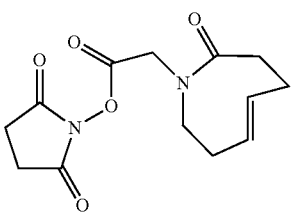

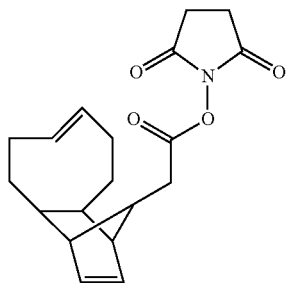

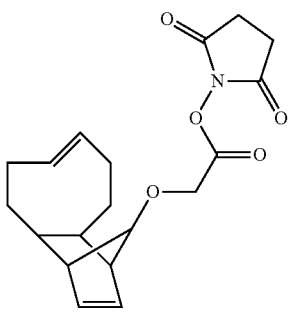

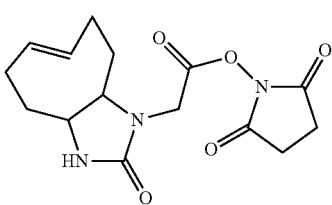

-continued

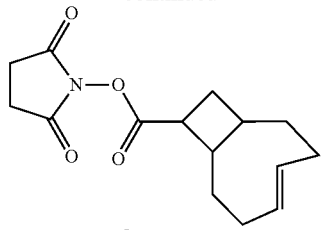

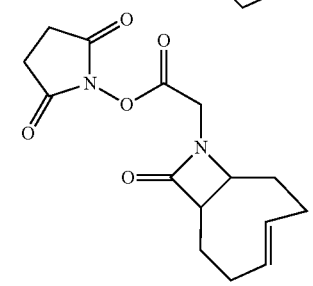

said compound further comprising the at least one linkage which links the dienophile, either directly or by way of a spacer, to the pre-targeting probe or the effector probe, said linkage being in the position of said N-hydroxy succinimide ester groups.

2. A compound comprised in a kit for targeted medical imaging and/or therapeutics, comprising at least one pre-targeting probe and at least one effector probe, wherein the pre-targeting probe comprises a primary targeting moiety and a first bio-orthogonal reactive group, and wherein the effector probe comprises an effector moiety, such as a label or a pharmaceutically active compound, and a second bio-orthogonal reactive group, wherein either of the first and second bio-orthogonal reactive groups is a dienophile and the other of the first and second bio-orthogonal reactive groups is a diene, wherein the dienophile is a trans-cyclooctene moiety comprising at least two exocyclic bonds fixed in the same plane, and comprising at least one linkage, either directly or by way of a spacer, to the pre-targeting probe or the effector probe, the compound being selected from the following structures, said structures showing N-hydroxy succinimide ester groups:

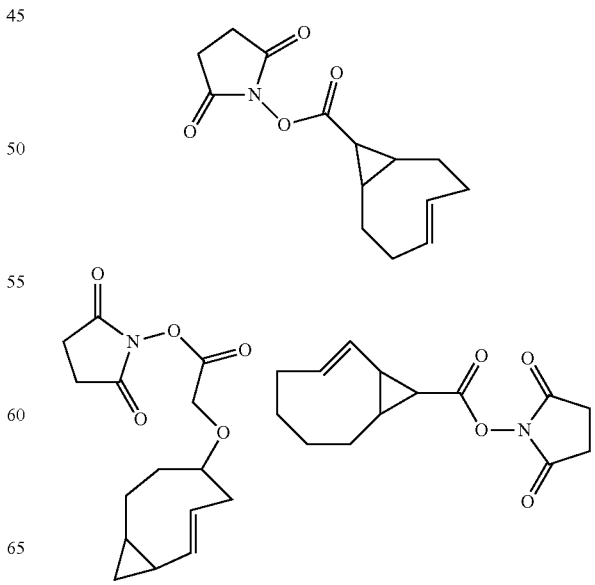

61
-continued

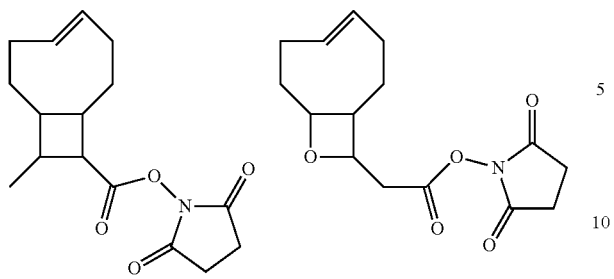

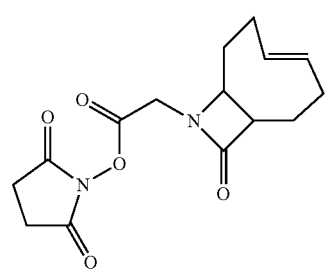

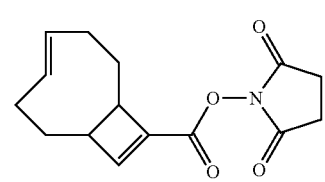

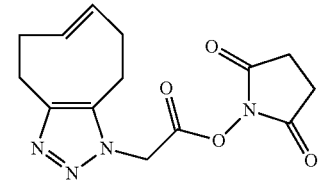

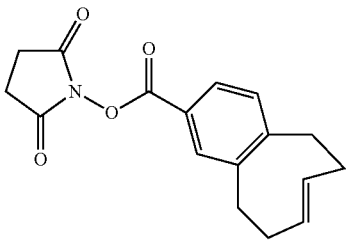

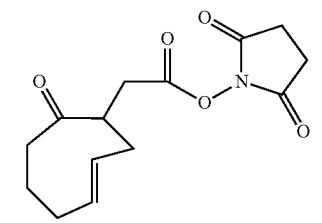

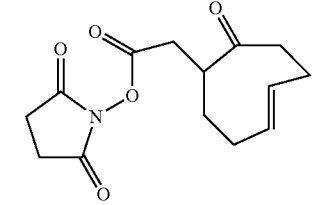

62
-continued

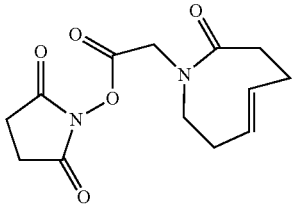

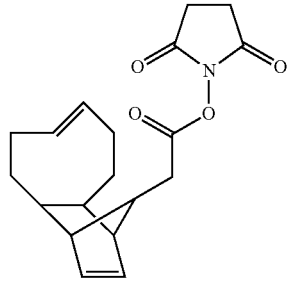

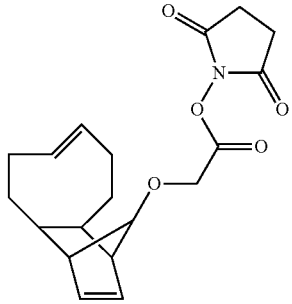

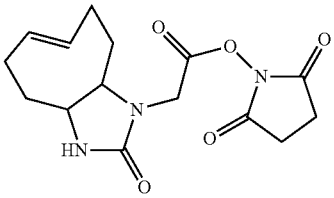

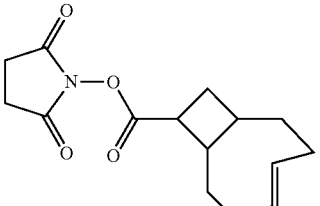

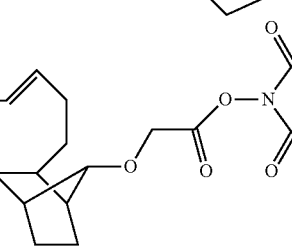

said compound further comprising the at least one linkage which links the dienophile, either directly or by way of a spacer, to the pre-targeting probe or the effector probe, said linkage being in the position of said N-hydroxy succinimide ester groups.

3. A kit for targeted medical imaging and/or therapeutics, comprising at least one pre-targeting probe and at least one effector probe, wherein the pre-targeting probe comprises a primary targeting moiety and a first bio-orthogonal reactive group, and wherein the effector probe comprises an effector moiety, such as a label or a pharmaceutically active compound, and a second bio-orthogonal reactive group, wherein either of the first and second bio-orthogonal reactive groups is a dienophile and the other of the first and second bio-orthogonal reactive groups is a diene, wherein the dienophile is a trans-cyclooctene moiety comprising at least two exocyclic bonds fixed in the same plane, and comprising at least one linkage which links the dienophile, either directly or by way of a spacer, to the pre-targeting probe or the effector probe, or comprising at least one linkage which links the diene, either directly or by way of a spacer, to the pre-targeting probe or the effector probe; and wherein the at least two exocyclic bonds are part of a substantially flat fused ring structure.

4. A kit for targeted medical imaging and/or therapeutics, comprising at least one pre-targeting probe and at least one effector probe, wherein the pre-targeting probe comprises a primary targeting moiety and a first bio-orthogonal reactive group, and wherein the effector probe comprises an effector moiety, such as a label or a pharmaceutically active compound, and a second bio-orthogonal reactive group, wherein either of the first and second bio-orthogonal reactive groups is a dienophile and the other of the first and second bio-orthogonal reactive groups is a diene, wherein the dienophile is a trans-cyclooctene moiety comprising at least two exocyclic bonds fixed in the same plane, and comprising at least one linkage which links the dienophile, either directly or by way of a spacer, to the pre-targeting probe or the effector probe, or comprising at least one linkage which links the diene, either directly or by way of a spacer, to the pre-targeting probe or the effector probe; and wherein the at least two exocyclic bonds are part of a substantially flat fused ring structure and at least two exocyclic bonds are part of a fused aromatic ring.

* * * * *